US012617747B2

(12) United States Patent
Barr et al.

(10) Patent No.: US 12,617,747 B2
(45) Date of Patent: May 5, 2026

(54) CANNABINOID ANALOGS AND METHODS FOR THEIR PREPARATION

(71) Applicant: InMed Pharmaceuticals Inc., Vancouver (CA)

(72) Inventors: Philip J. Barr, Oakland, CA (US); Charles K. Marlowe, Emerald Hills, CA (US); Jianping Sun, Redwood City, CA (US); James T. Kealey, Sebastopol, CA (US)

(73) Assignee: INMED PHARMACEUTICALS INC., Vancouver (CA)

( * ) Notice: Subject to any disclaimer, the term of this patent is extended or adjusted under 35 U.S.C. 154(b) by 1053 days.

(21) Appl. No.: 17/289,868

(22) PCT Filed: Oct. 31, 2019

(86) PCT No.: PCT/US2019/059237
§ 371 (c)(1),
(2) Date: Apr. 29, 2021

(87) PCT Pub. No.: WO2020/092823
PCT Pub. Date: May 7, 2020

(65) Prior Publication Data

US 2021/0403408 A1 Dec. 30, 2021

Related U.S. Application Data

(60) Provisional application No. 62/753,708, filed on Oct. 31, 2018, provisional application No. 62/767,447, filed on Nov. 14, 2018.

(51) Int. Cl.

| | |
|---|---|
| ***C07C 65/19*** | (2006.01) |
| ***C07B 59/00*** | (2006.01) |

(Continued)

(52) U.S. Cl.
CPC ............ *C07C 65/19* (2013.01); *C07B 59/001* (2013.01); *C07C 39/08* (2013.01); *C07C 39/373* (2013.01);
(Continued)

(58) Field of Classification Search
CPC ......... C07C 65/19; C07C 39/08; C07C 65/03; C07D 311/58; C07D 311/80; C07D 311/78
See application file for complete search history.

(56) References Cited

U.S. PATENT DOCUMENTS

| | | | |
|---|---|---|---|
| 3,919,322 A | 11/1975 | Brossi et al. | |
| 4,315,862 A | 2/1982 | Elsohly et al. | |

(Continued)

FOREIGN PATENT DOCUMENTS

| | | | | |
|---|---|---|---|---|
| AR | 106951 | * | 3/2018 | ........... A61K 31/352 |
| EP | 0304842 A2 | | 3/1989 | |

(Continued)

OTHER PUBLICATIONS

Abdulkhani, A., et al., Evaluation of antibacterial activity of cellulose nanofibers/polylactic acid composites coated with ethanolic extract of propolis, Polymer composites, 38(1), pp. 13-19 (Year: 2017).*

(Continued)

*Primary Examiner* — Yate' K Cutliff
(74) *Attorney, Agent, or Firm* — Michael J. Adams

(57) ABSTRACT

Provided herein are cannabinoid analogs, including halogenated cannabinoid analogs, hydroxylated cannabinoid analogs, deuterated cannabinoid analogs, and tritiated cannabinoid analogs. The cannabinoid analogs can be prepared by partial or total expression in modified host cells, such as (Continued)

recombinantly modified yeast cells, optionally in combination with chemical synthetic steps.

16 Claims, 1 Drawing Sheet

Specification includes a Sequence Listing.

(51) Int. Cl.

| | |
|---|---|
| ***C07C 39/08*** | (2006.01) |
| ***C07C 39/373*** | (2006.01) |
| ***C07C 65/00*** | (2006.01) |
| ***C07C 65/03*** | (2006.01) |
| ***C07D 311/58*** | (2006.01) |
| ***C07D 311/80*** | (2006.01) |
| ***C12N 9/10*** | (2006.01) |
| *C07C 63/04* | (2006.01) |

(52) U.S. Cl.

CPC .............. *C07C 65/00* (2013.01); *C07C 65/03* (2013.01); *C07D 311/58* (2013.01); *C12N 9/1014* (2013.01); *C12N 9/1029* (2013.01); *C12N 9/1085* (2013.01); *C12Y 203/01206* (2015.07); *C12Y 205/01102* (2015.07); *C12Y 404/01026* (2015.07); *C07C 63/04* (2013.01)

(56) References Cited

U.S. PATENT DOCUMENTS

| | | | | |
|---|---|---|---|---|
| 4,837,228 | A | 6/1989 | Elsohly et al. | |
| 5,919,651 | A | 7/1999 | Hitzeman et al. | |
| 6,033,883 | A | 3/2000 | Barr et al. | |
| 6,228,647 | B1 | 5/2001 | Voytas et al. | |
| 6,258,566 | B1 | 7/2001 | Barr et al. | |
| 7,078,233 | B2 | 7/2006 | Barr et al. | |
| 8,124,390 | B2 | 2/2012 | Kuzuyama et al. | |
| 8,236,552 | B2 | 8/2012 | Millis et al. | |
| 8,884,100 | B2 | 11/2014 | Page et al. | |
| 9,376,367 | B2 | 6/2016 | Herkenroth et al. | |
| 9,546,362 | B2 | 1/2017 | Page et al. | |
| 9,611,460 | B2 | 4/2017 | Page et al. | |
| 9,637,763 | B2 | 5/2017 | Barr | |
| 10,837,031 | B2 | 11/2020 | Barr et al. | |
| 11,399,611 | B2 * | 8/2022 | Philippe | A45D 7/06 |
| 11,414,366 | B2 * | 8/2022 | Nandy | C07C 39/225 |
| 2003/0158191 | A1 | 8/2003 | Travis | |
| 2003/0232101 | A1 * | 12/2003 | Travis | A61K 9/0034 424/776 |
| 2008/0031977 | A1 | 2/2008 | Musty et al. | |
| 2008/0275135 | A1 | 11/2008 | Mechoulam et al. | |
| 2010/0298579 | A1 | 11/2010 | Steup et al. | |
| 2014/0141476 | A1 | 5/2014 | Page et al. | |
| 2015/0299732 | A1 | 10/2015 | Millis et al. | |
| 2015/0336874 | A1 | 11/2015 | Koch et al. | |
| 2016/0010126 | A1 | 1/2016 | Poulos et al. | |
| 2016/0053220 | A1 | 2/2016 | Peet et al. | |
| 2016/0068869 | A1 | 3/2016 | Piotrowski et al. | |
| 2018/0263952 | A1 * | 9/2018 | Bíró | A61P 17/10 |
| 2018/0334692 | A1 | 11/2018 | Barr et al. | |
| 2021/0040512 | A1 | 2/2021 | Barr et al. | |
| 2022/0177858 | A1 | 6/2022 | Noble et al. | |
| 2023/0063862 | A1 * | 3/2023 | Marlowe | C07D 311/58 |

FOREIGN PATENT DOCUMENTS

| | | | | |
|---|---|---|---|---|
| EP | 3372590 | A1 | 9/2018 | |
| EP | 3666765 | A1 | 6/2020 | |
| WO | WO 2011006099 | A1 | 1/2011 | |
| WO | WO 2014177593 | A1 | 11/2014 | |
| WO | WO 2017051020 | A1 | 3/2017 | |
| WO | 2017161041 | | 9/2017 | |
| WO | WO 2017175064 | A1 | 10/2017 | |
| WO | WO 2018026263 | A1 | 2/2018 | |
| WO | WO 2018057385 | A2 | 3/2018 | |
| WO | WO 2018148848 | A1 | 8/2018 | |
| WO | WO-2018152334 | A1 * | 8/2018 | A23L 29/035 |
| WO | 2018/200888 | A1 | 11/2018 | |
| WO | 2019/071000 | A1 | 4/2019 | |
| WO | WO 2020214574 | A1 | 10/2020 | |
| WO | WO 2020214951 | A1 | 10/2020 | |
| WO | WO 2021133989 | A1 | 7/2021 | |

OTHER PUBLICATIONS

Hwangbo, K., et al., Inhibition of DNA Topoisomerase I and II of compounds from Reynoutria Japonica, Achieves of Pharmacal Research, vol. 35, No. 9, pp. 1583-1589 (Year: 2012).*

Hwangbo, K., et al., Inhibition of DNA Topoisomerase I and II of compounds from Reynoutria japonica, Archives of Pharmacal Research, vol. 35, No. 9, pp. 1583-1589 (Year: 2012).*

Qi, L., et al., delta-9-tetrahydrocannabinol Immunochemical Studies: Haptens, monocolonal antibodies, and a convenient synthesis of radiolabeled delta-9-tetrahydrocannabinol, Journal of Medicinal Chemistry, American Chemical Society, vol. 48, No. 23, pp. 7389-7399 (Year: 2005).*

Zanto, C., et al., Synthesis, radio-synthesis and in vitro evaluation of terminally fluorinated derivatives of HU-210 and HU-211 as novel candidates PET tracers, Organic & Biomolecular Chemistry, vol. 15, No. 9, pp. 2086-2096 (Year: 2017).*

Ahmed, S. A., et al., Minor oxygenated cannabinoids from high potency *Cannabis sativa* L., Phytochemistry (Elsevier), 117, pp. 194-199 (Year: 2015).*

Baek SH et al. (1985) "Boron trifluoride etherate on alumina—a modified Lewis acid reagent. An improved synthesis of cannabinol." *Tetrahedron Letters* 26(8): 1083-1086.

Black PN, et al. (May 16, 2006) "Yeast acyl-CoA synthetases at the crossroads of fatty acid metabolism and regulation." *BiochimBiophys Acta.* 1771(3):286-98.

Crombie L, et al. (Jan. 1, 1988) "Synthesis of Cannabinoids Carrying ω-Carboxy Substituents: The Cannabidiols, Cannabinol and Δ1- and Δ6-Tetrahydrocannabinols of this Series." *J. Chem Soc. Perkin Trans. I* 1998: 1255-1262.

Elsohly M, et al (2005) "Chemical constituents of marijuana: The complex mixture of natural cannabinoids." *Life Sciences* 78: 539-548.

Fellermeier M, et al. (May 8, 1998) "Prenylation of olivetolate by a hemp transferase yields cannabigerolic acid, the precursor of tetrahydrocannabinol." *FEBS Lett* 427: 283-285.

Flores-Sanchez I (Oct. 29, 2008) "Polyketide synthasesin *Cannabis sativa* L." Doctoral thesis, Leiden University.

Flores-Sanchez I, et al. (Apr. 8, 2008) "Secondary metabolism in cannabis." *Phytochem Rev* 7:615-639.

Flores-Sanchez I, et al. (Dec. 3, 2008) "PKS Activities and Biosynthesis of Cannabinoids and Flavonoidsin *Cannabis sativa* L. Plants." *Plant Cell Physiol.* 49(12):1767-1782.

Gagne S et al. (Jul. 31, 2012) "Identification of olivetolic acid cyclase from *Cannabis sativa* revealsa unique catalytic route to plant polyketides." *Proc. Nat. Acad. Sci. USA* 109: 12811-12816.

Hazekamp A et al. (2005) "Chromatographic and Spectroscopic Data of Cannabinoids from *Cannabis sativa* L." *Journal of Liquid Chromatography & Related Techniques* 28: 2361-2382,.

Kumano T, et al. (Sep. 1, 2008) "Chemoenzymatic syntheses of prenylated aromatic small moleculesusing *Streptomyces* prenyltransferaseswith relaxed substrate specificities." *Bioorg Med Chem* 16(17): 8117-8126.

Kuzuyama T, et al. (Jun. 16, 2005) "Structural basis for the promiscuous biosynthetic prenylation of aromatic natural products." *Nature* 435(7044): 983-987.

Li, M. et al. (Sep. 4, 2015) "De novo production of resveratrol from glucose or ethanol by engineered *Saccharomyces cerevisiae.*" Metabolic Engineering 32 (2015) 1-11.

Mechoulam R, et al. (1969) "Stereo selective synthesis of cannabinoid 1,5 dienes." *Tetrahedron Letters* 60:5349-5352.

(56) References Cited

OTHER PUBLICATIONS

Miyazawa T, et al. (Sep. 16, 2015) "Identification of Middle Chain Fatty Acyl-CoA Ligase Responsible for the Biosynthesis of 2-Alkylmalonyl-CoAs for Polyketide Extender Unit." *J. Biol. Chem* 290: 26994-27011.
Morimoto S, et al. (1999) "Biosynthesis of cannabinoidsin *Cannabis sativa* L." *Curr Top Phytochem*2: 103-113.
Morimoto S, et al. (Nov. 20, 1998) "Purification and characterization of cannabichromenic acid synthase from *Cannabis sativa." Phytochemistry* 49: 1525-1529.
Pamplaniyil, K., "Identification, isolation and functional characterization of prenyltransferases in *Cannabis sativa* L.", Jan. 1, 2018; Technischen Universität Dortmund; PhD dissertation; https://eldorado.tu-dortmund.de/handle/2003/36335; 141 pages.
PCT/US2019/059237, "International Search Report and Written Opinion", Mar. 31, 2020, 16 pages.
PubChem Compound Summary, PubChem CID: 66591394, Jan. 31, 2020, pp. 1-11, retrieved from the Intemet (pubchem.ncbi.nlm.nih.gov/compound/66591394, p. 2, formula).
Shockey J, et al. (Jun. 2003) "*Arabadopsis* Contains a Large Superfamily of Acyl-Activating Enzymes. Phylogenetic and Biochemical Analysis Reveals a New Class of Acyl-Coenzyme A Synthetases." *Plant Physiology* 132: 1065-1076.
Shoyama Y, et al. (1978) "Cannabis XI. Synthesis of cannabigerorcinic-carboxyl-$^{14}$C acid, cannabigerovarinic carboxyl-$^{14}$C acid, cannabidivarinic-carboxyl-$^{14}$C acid and dl-cannabichromevarinic-carboxyl-$^{14}$C acid." *Journal of Labelled Compounds and Radiopharmaceuticals.* 14(8):835-842.
Sirikantaramass, et al. (2017) "Chapter 8. Cannabinoids: Biosynthesis and Biotechnological Applications." *Cannabis sativa* L.—*Botany and Biotechnology*, S. Chandra et al. (eds.), Springer International Publishing AG, pp. 183-206.
Stout JM et al. (Jun. 1, 2012) "The hexanoyl-CoA precursor forcannabinoid biosynthesisis formed by an acyl-activating enzyme in *Cannabis sativa* trichomes." *The Plant Journal* 71:353-365.
Taura et al., "Purification and Characterization of Cannabidiolic-acid Synthase from *Cannabis sativa* L.", Journal of Biological Chemistry, vol. 271, No. 29, Jul. 19, 1996, pp. 17411-17416.
Taura F, et al. (Jun. 18, 2009) "Characterization of olivetol synthase, a polyketide synthase putatively involved in cannabinoid biosynthetic pathway." *FEBS Lett* 583:2061-2066.
Taura F, et al. (Jun. 26, 2007) "Cannabidiolic-acid synthase, the chemotype-determining enzyme in the fiber-type *Cannabis sativa." FEBS Lett* 581:2929-2934.
Van Bakel H et al. (Oct. 20, 2011) "The draft genome and transcriptome of *Cannabis sativa." Genome Biology* 12: R102.
Yang X, et al. (Jan. 18, 2016) "Structural basis for olivetolic acid formation by a polyketide cyclase from *Cannabis sativa." FEBS J.* 283:1088-1106.
Driessen, Robert Andre, "Deuterium Labeled Gannabinoids: synthesis and mass spectrometry Proefschrift Ter Verkrijging Van De Graad Van Doctor in De Wiskunde En Natuurwetenschappen Aan De Rijksuniversiteit Te Utrecht, Op Gezag Van De Rector Magnificus Prof. Dr. A. Verhoeff, Volgens Beslutt Van Het College Van Decanen in H", Utrecht, pp. 1-146 (1979).
Eisohly et al., "Synthesis and Antimicrobial Activities of Certain Cannabichromene and Cannabigerol Related Compounds", J. Pharmaceutical Sciences, vol. 71, No. 12 (1982).
Girard et al., "A simple and eficient synthesis of 5'-($^{2}H_{3}$)olivetol", Can. J. Chem. vol. 65, pp. 189-190 (1987).
Harvey, D. J. and Brown, N. K., "Comparative In Vitro Metabolism of the Cannabinoids", Pharmacology, Biochemistry and Behavior, vol. 40, pp. 533-540 (1991).
Lee, Yong Rok and Wang, Xue, "Concise Synthesis of Biologically Interesting (±)-Cannabichromene, (±)-Cannabichromenic Acid, and (±)-Daurichromenic Acid", Bull. Korean Chem. Soc., vol. 26, No. 12, pp. 1933-1936 (2005).
Lee Y R et al., "Efficient and general method for the synthesis of benzopyrans by ethylenediamine diacetate-catalyzed reactions of resorcinols with alfa, beta-unsaturated aldehydes. One step synthesis of biologically active (+/-)-confluentin and (+/-)-daurichromenic acid", Tetrahedron Letters, Elsevier, Amsterdam, NL, vol. 46, No. 44, pp. 7539-7543 (2005).
Roth et al. "Regioselective synthesis of isotopically labeled Δ9-tetrahydrocannabinolic acid A (THCA-A-D3) by reaction of Δ9-tetrahydrocannabinol-D3 with magnesium methyl carbonate", Forensic Science International 222, Issue 1-3, pp. 368-372 (2012).
Russo, B. & Marcu, Johan "Chapter Three, Cannabis Pharmacology: The Usual Suspects and a Few Promising Leads", Advances in Pharmacology, vol. 80, pp. 67-134 (2017).
Yun et al. "UPLC-Q-TOF/MS characterization, HPLC fingerprint analysis and species differentiation for quality control of Nigella glandulifera Freyn et Sint seeds and *Nigella sativa* L. seeds", Analytical Methods, 6(13), pp. 4845-4852 (2014).
Pitt C. G. et al, "The synthesis of deuterium, carbon-14, and carrier-free tritium labeled cannabinoids", Journal of Labelled Compounds., GB, vol. 11, No. 4, pp. 551-575, (1975).
Qi et al, "$\Delta^{9}$-Tetrahydrocannabinol Immunochemical Studies: Haptens, Monoclonal Antibodies, and a Convenient Synthesis of Radiolabeled Δ9 -Tetrahydrocannabinol", Journal of Medicinal Chemistry, US, vol. 48, No. 23, pp. 7389-7399 (2005).
Zanato et al, "Synthesis, radio-synthesis and in vitro evaluation of terminally fluorinated derivatives of HU-210 and HU-211 as novel candidate PET tracers", Organic & Biomolecular Chemistry, vol. 15, No. 9, pp. 2086-2096 (2017).
130414-07-2, STN Registry, published on Nov. 16, 1990.
134914-55-9, STN Registry, published on Jul. 19, 1991.
Caprioglio et al., "One-Pot Total Synthesis of Cannabinol via lodine-Mediated Deconstructive Annulation", Org. Lett. Vol.21, pp. 6122-6125 (2019).
Choudhary et al., "Isolation and characterization of phenolic compound from Rhodiola imbricata, a Trans-Himalayan food crop having antioxidant and anticancer potential", J. of Functional Foods, vol. 16, pp. 183-193 (2015).
Kumar et al., "UPLC-MS/MS quantitative analysis and structural fragmentation study of five Parmotrema lichens from the Eastern Ghats", Journal of Pharmaceutical and Biomedical Analysis, vol. 156, pp. 45-57 (2018).
Martin et al., "Pharmacological evaluation of iodo and nitro analogs of A8-THC and A9-THC", Pharmacology, Biochemistry and Behavior, vol. 46(2), pp. 295-301 (1993).
Taylor, Edward C. and Strojny, E.J., "The Synthesis of Some Model Compounds Related to Tetrahydrocannabinol", Journal of the American Chemical Society, vol. 82, pp. 5198-5202 (1960).

* cited by examiner

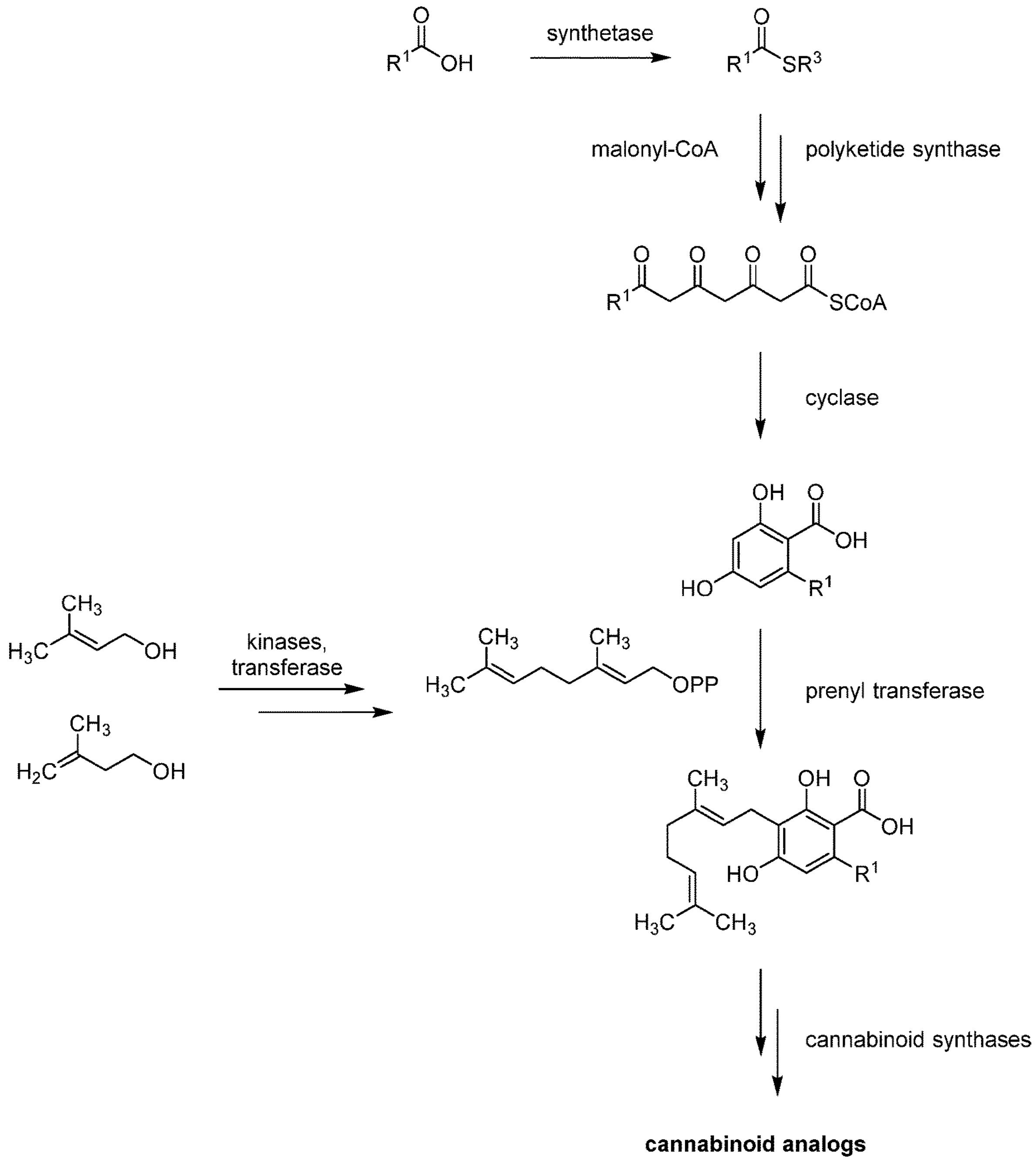
synthetase
malonyl-CoA
polyketide synthase
cyclase
kinases,
transferase
prenyl transferase
cannabinoid synthases
cannabinoid analogs

SEQUENCE LISTING

<160> NUMBER OF SEQ ID NOS: 10

<210> SEQ ID NO 1
<211> LENGTH: 579
<212> TYPE: PRT
<213> ORGANISM: Streptomyces sp.

<400> SEQUENCE: 1

Met Glu Leu Ala Leu Pro Ala Glu Leu Ala Pro Thr Leu Pro Glu Ala
1               5                   10                  15

Leu Arg Leu Arg Ser Glu Gln Gln Pro Asp Thr Val Ala Tyr Val Phe
            20                  25                  30

Leu Arg Asp Gly Glu Thr Pro Glu Glu Thr Leu Thr Tyr Gly Arg Leu
        35                  40                  45

Asp Arg Ala Ala Arg Ala Arg Ala Ala Ala Leu Glu Ala Ala Gly Leu
    50                  55                  60

Ala Gly Gly Thr Ala Val Leu Leu Tyr Pro Ser Gly Leu Glu Phe Val
65                  70                  75                  80

Ala Ala Leu Leu Gly Cys Met Tyr Ala Gly Thr Ala Gly Ala Pro Val
                85                  90                  95

Gln Val Pro Thr Arg Arg Arg Gly Met Glu Arg Ala Arg Arg Ile Ala
            100                 105                 110

Asp Asp Ala Gly Ala Lys Thr Ile Leu Thr Thr Thr Ala Val Lys Arg
        115                 120                 125

Glu Val Glu Glu His Phe Ala Asp Leu Leu Thr Gly Leu Thr Val Ile
    130                 135                 140

Asp Thr Glu Ser Leu Pro Asp Val Pro Asp Asp Ala Pro Ala Val Arg
145                 150                 155                 160

Leu Pro Gly Pro Asp Asp Val Ala Leu Leu Gln Tyr Thr Ser Gly Ser
                165                 170                 175

Thr Gly Asp Pro Lys Gly Val Glu Val Thr His Ala Asn Phe Arg Ala
            180                 185                 190

Asn Val Ala Glu Thr Val Glu Leu Trp Pro Val Arg Ser Asp Gly Thr
        195                 200                 205

Val Val Asn Trp Leu Pro Leu Phe His Asp Met Gly Leu Met Phe Gly
    210                 215                 220

Val Val Met Pro Leu Phe Thr Gly Val Pro Ala Tyr Leu Met Ala Pro
225                 230                 235                 240

Gln Ser Phe Ile Arg Arg Pro Ala Arg Trp Leu Glu Ala Ile Ser Arg
                245                 250                 255

Phe Arg Gly Thr His Ala Ala Ala Pro Ser Phe Ala Tyr Glu Leu Cys
            260                 265                 270

Val Arg Ser Val Ala Asp Thr Gly Leu Pro Ala Gly Leu Asp Leu Ser
        275                 280                 285

Ser Trp Arg Val Ala Val Asn Gly Ala Glu Pro Val Arg Trp Thr Ala
    290                 295                 300

Val Ala Asp Phe Thr Glu Ala Tyr Ala Pro Ala Gly Phe Arg Pro Gln
305                 310                 315                 320

Ala Met Cys Pro Gly Tyr Gly Leu Ala Glu Asn Thr Leu Lys Leu Ser
                325                 330                 335

Gly Ser Pro Glu Asp Arg Pro Pro Thr Leu Leu Arg Ala Asp Ala Ala
            340                 345                 350

Ala Leu Gln Asp Gly Arg Val Val Pro Leu Thr Gly Pro Gly Thr Asp
        355                 360                 365

Gly Val Arg Leu Val Gly Ser Gly Val Thr Val Pro Ser Ser Arg Val
    370                 375                 380

Ala Val Val Asp Pro Gly Thr Gly Thr Glu Gln Pro Ala Gly Arg Val
385                 390                 395                 400

Gly Glu Ile Trp Ile Asn Gly Pro Cys Val Ala Arg Gly Tyr His Gly

-continued

```
                405                 410                 415

Arg Pro Ala Glu Ser Ala Glu Ser Phe Gly Ala Arg Ile Ala Gly Gln
            420                 425                 430

Glu Ala Arg Gly Thr Trp Leu Arg Thr Gly Asp Leu Gly Phe Leu His
        435                 440                 445

Asp Gly Glu Val Phe Val Ala Gly Arg Leu Lys Asp Val Val Ile His
    450                 455                 460

Gln Gly Arg Asn Phe Tyr Pro Gln Asp Ile Glu Leu Ser Ala Glu Val
465                 470                 475                 480

Ser Asp Arg Ala Leu His Pro Asn Cys Ala Ala Ala Phe Ala Leu Asp
                485                 490                 495

Asp Gly Arg Thr Glu Arg Leu Val Leu Leu Val Glu Ala Asp Gly Arg
            500                 505                 510

Ala Leu Arg Asn Gly Gly Ala Asp Ala Leu Arg Ala Arg Val His Asp
        515                 520                 525

Ala Val Trp Asp Arg Gln Arg Leu Arg Ile Asp Glu Ile Val Leu Leu
    530                 535                 540

Arg Arg Gly Ala Leu Pro Lys Thr Ser Ser Gly Lys Val Gln Arg Arg
545                 550                 555                 560

Leu Ala Arg Ser Arg Tyr Leu Asp Gly Glu Phe Gly Pro Ala Pro Ala
                565                 570                 575

Arg Glu Ala


<210> SEQ ID NO 2
<211> LENGTH: 543
<212> TYPE: PRT
<213> ORGANISM: Cannabis sativa

<400> SEQUENCE: 2

Met Glu Lys Ser Gly Tyr Gly Arg Asp Gly Ile Tyr Arg Ser Leu Arg
1               5                   10                  15

Pro Pro Leu His Leu Pro Asn Asn Asn Asn Leu Ser Met Val Ser Phe
            20                  25                  30

Leu Phe Arg Asn Ser Ser Ser Tyr Pro Gln Lys Pro Ala Leu Ile Asp
        35                  40                  45

Ser Glu Thr Asn Gln Ile Leu Ser Phe Ser His Phe Lys Ser Thr Val
    50                  55                  60

Ile Lys Val Ser His Gly Phe Leu Asn Leu Gly Ile Lys Lys Asn Asp
65                  70                  75                  80

Val Val Leu Ile Tyr Ala Pro Asn Ser Ile His Phe Pro Val Cys Phe
                85                  90                  95

Leu Gly Ile Ile Ala Ser Gly Ala Ile Ala Thr Thr Ser Asn Pro Leu
            100                 105                 110

Tyr Thr Val Ser Glu Leu Ser Lys Gln Val Lys Asp Ser Asn Pro Lys
        115                 120                 125

Leu Ile Ile Thr Val Pro Gln Leu Leu Glu Lys Val Lys Gly Phe Asn
    130                 135                 140

Leu Pro Thr Ile Leu Ile Gly Pro Asp Ser Glu Gln Glu Ser Ser Ser
145                 150                 155                 160

Asp Lys Val Met Thr Phe Asn Asp Leu Val Asn Leu Gly Gly Ser Ser
                165                 170                 175

Gly Ser Glu Phe Pro Ile Val Asp Asp Phe Lys Gln Ser Asp Thr Ala
            180                 185                 190

Ala Leu Leu Tyr Ser Ser Gly Thr Thr Gly Met Ser Lys Gly Val Val
```

-continued

```
        195                 200                 205

Leu Thr His Lys Asn Phe Ile Ala Ser Ser Leu Met Val Thr Met Glu
    210                 215                 220

Gln Asp Leu Val Gly Glu Met Asp Asn Val Phe Leu Cys Phe Leu Pro
225                 230                 235                 240

Met Phe His Val Phe Gly Leu Ala Ile Ile Thr Tyr Ala Gln Leu Gln
                245                 250                 255

Arg Gly Asn Thr Val Ile Ser Met Ala Arg Phe Asp Leu Glu Lys Met
            260                 265                 270

Leu Lys Asp Val Glu Lys Tyr Lys Val Thr His Leu Trp Val Val Pro
        275                 280                 285

Pro Val Ile Leu Ala Leu Ser Lys Asn Ser Met Val Lys Lys Phe Asn
    290                 295                 300

Leu Ser Ser Ile Lys Tyr Ile Gly Ser Gly Ala Ala Pro Leu Gly Lys
305                 310                 315                 320

Asp Leu Met Glu Glu Cys Ser Lys Val Val Pro Tyr Gly Ile Val Ala
                325                 330                 335

Gln Gly Tyr Gly Met Thr Glu Thr Cys Gly Ile Val Ser Met Glu Asp
            340                 345                 350

Ile Arg Gly Gly Lys Arg Asn Ser Gly Ser Ala Gly Met Leu Ala Ser
        355                 360                 365

Gly Val Glu Ala Gln Ile Val Ser Val Asp Thr Leu Lys Pro Leu Pro
    370                 375                 380

Pro Asn Gln Leu Gly Glu Ile Trp Val Lys Gly Pro Asn Met Met Gln
385                 390                 395                 400

Gly Tyr Phe Asn Asn Pro Gln Ala Thr Lys Leu Thr Ile Asp Lys Lys
                405                 410                 415

Gly Trp Val His Thr Gly Asp Leu Gly Tyr Phe Asp Glu Asp Gly His
            420                 425                 430

Leu Tyr Val Val Asp Arg Ile Lys Glu Leu Ile Lys Tyr Lys Gly Phe
        435                 440                 445

Gln Val Ala Pro Ala Glu Leu Glu Gly Leu Leu Val Ser His Pro Glu
    450                 455                 460

Ile Leu Asp Ala Val Val Ile Pro Phe Pro Asp Ala Glu Ala Gly Glu
465                 470                 475                 480

Val Pro Val Ala Tyr Val Val Arg Ser Pro Asn Ser Ser Leu Thr Glu
                485                 490                 495

Asn Asp Val Lys Lys Phe Ile Ala Gly Gln Val Ala Ser Phe Lys Arg
            500                 505                 510

Leu Arg Lys Val Thr Phe Ile Asn Ser Val Pro Lys Ser Ala Ser Gly
        515                 520                 525

Lys Ile Leu Arg Arg Glu Leu Ile Gln Lys Val Arg Ser Asn Met
    530                 535                 540


<210> SEQ ID NO 3
<211> LENGTH: 720
<212> TYPE: PRT
<213> ORGANISM: Cannabis sativa

<400> SEQUENCE: 3

Met Gly Lys Asn Tyr Lys Ser Leu Asp Ser Val Val Ala Ser Asp Phe
1               5                   10                  15

Ile Ala Leu Gly Ile Thr Ser Glu Val Ala Glu Thr Leu His Gly Arg
            20                  25                  30
```

-continued

```
Leu Ala Glu Ile Val Cys Asn Tyr Gly Ala Ala Thr Pro Gln Thr Trp
        35                  40                  45

Ile Asn Ile Ala Asn His Ile Leu Ser Pro Asp Leu Pro Phe Ser Leu
    50                  55                  60

His Gln Met Leu Phe Tyr Gly Cys Tyr Lys Asp Phe Gly Pro Ala Pro
65                  70                  75                  80

Pro Ala Trp Ile Pro Asp Pro Glu Lys Val Lys Ser Thr Asn Leu Gly
                85                  90                  95

Ala Leu Leu Glu Lys Arg Gly Lys Glu Phe Leu Gly Val Lys Tyr Lys
            100                 105                 110

Asp Pro Ile Ser Ser Phe Ser His Phe Gln Glu Phe Ser Val Arg Asn
        115                 120                 125

Pro Glu Val Tyr Trp Arg Thr Val Leu Met Asp Glu Met Lys Ile Ser
    130                 135                 140

Phe Ser Lys Asp Pro Glu Cys Ile Leu Arg Arg Asp Asp Ile Asn Asn
145                 150                 155                 160

Pro Gly Gly Ser Glu Trp Leu Pro Gly Gly Tyr Leu Asn Ser Ala Lys
                165                 170                 175

Asn Cys Leu Asn Val Asn Ser Asn Lys Lys Leu Asn Asp Thr Met Ile
            180                 185                 190

Val Trp Arg Asp Glu Gly Asn Asp Asp Leu Pro Leu Asn Lys Leu Thr
        195                 200                 205

Leu Asp Gln Leu Arg Lys Arg Val Trp Leu Val Gly Tyr Ala Leu Glu
    210                 215                 220

Glu Met Gly Leu Glu Lys Gly Cys Ala Ile Ala Ile Asp Met Pro Met
225                 230                 235                 240

His Val Asp Ala Val Val Ile Tyr Leu Ala Ile Val Leu Ala Gly Tyr
                245                 250                 255

Val Val Val Ser Ile Ala Asp Ser Phe Ser Ala Pro Glu Ile Ser Thr
            260                 265                 270

Arg Leu Arg Leu Ser Lys Ala Lys Ala Ile Phe Thr Gln Asp His Ile
        275                 280                 285

Ile Arg Gly Lys Lys Arg Ile Pro Leu Tyr Ser Arg Val Val Glu Ala
    290                 295                 300

Lys Ser Pro Met Ala Ile Val Ile Pro Cys Ser Gly Ser Asn Ile Gly
305                 310                 315                 320

Ala Glu Leu Arg Asp Gly Asp Ile Ser Trp Asp Tyr Phe Leu Glu Arg
                325                 330                 335

Ala Lys Glu Phe Lys Asn Cys Glu Phe Thr Ala Arg Glu Gln Pro Val
            340                 345                 350

Asp Ala Tyr Thr Asn Ile Leu Phe Ser Ser Gly Thr Thr Gly Glu Pro
        355                 360                 365

Lys Ala Ile Pro Trp Thr Gln Ala Thr Pro Leu Lys Ala Ala Ala Asp
    370                 375                 380

Gly Trp Ser His Leu Asp Ile Arg Lys Gly Asp Val Ile Val Trp Pro
385                 390                 395                 400

Thr Asn Leu Gly Trp Met Met Gly Pro Trp Leu Val Tyr Ala Ser Leu
                405                 410                 415

Leu Asn Gly Ala Ser Ile Ala Leu Tyr Asn Gly Ser Pro Leu Val Ser
            420                 425                 430

Gly Phe Ala Lys Phe Val Gln Asp Ala Lys Val Thr Met Leu Gly Val
        435                 440                 445

Val Pro Ser Ile Val Arg Ser Trp Lys Ser Thr Asn Cys Val Ser Gly
```

```
    450                 455                 460

Tyr Asp Trp Ser Thr Ile Arg Cys Phe Ser Ser Ser Gly Glu Ala Ser
465                 470                 475                 480

Asn Val Asp Glu Tyr Leu Trp Leu Met Gly Arg Ala Asn Tyr Lys Pro
                485                 490                 495

Val Ile Glu Met Cys Gly Gly Thr Glu Ile Gly Gly Ala Phe Ser Ala
            500                 505                 510

Gly Ser Phe Leu Gln Ala Gln Ser Leu Ser Ser Phe Ser Ser Gln Cys
        515                 520                 525

Met Gly Cys Thr Leu Tyr Ile Leu Asp Lys Asn Gly Tyr Pro Met Pro
    530                 535                 540

Lys Asn Lys Pro Gly Ile Gly Glu Leu Ala Leu Gly Pro Val Met Phe
545                 550                 555                 560

Gly Ala Ser Lys Thr Leu Leu Asn Gly Asn His His Asp Val Tyr Phe
                565                 570                 575

Lys Gly Met Pro Thr Leu Asn Gly Glu Val Leu Arg Arg His Gly Asp
            580                 585                 590

Ile Phe Glu Leu Thr Ser Asn Gly Tyr Tyr His Ala His Gly Arg Ala
        595                 600                 605

Asp Asp Thr Met Asn Ile Gly Gly Ile Lys Ile Ser Ser Ile Glu Ile
    610                 615                 620

Glu Arg Val Cys Asn Glu Val Asp Asp Arg Val Phe Glu Thr Thr Ala
625                 630                 635                 640

Ile Gly Val Pro Pro Leu Gly Gly Gly Pro Glu Gln Leu Val Ile Phe
                645                 650                 655

Phe Val Leu Lys Asp Ser Asn Asp Thr Thr Ile Asp Leu Asn Gln Leu
            660                 665                 670

Arg Leu Ser Phe Asn Leu Gly Leu Gln Lys Lys Leu Asn Pro Leu Phe
        675                 680                 685

Lys Val Thr Arg Val Val Pro Leu Ser Ser Leu Pro Arg Thr Ala Thr
    690                 695                 700

Asn Lys Ile Met Arg Arg Val Leu Arg Gln Gln Phe Ser His Phe Glu
705                 710                 715                 720


<210> SEQ ID NO 4
<211> LENGTH: 385
<212> TYPE: PRT
<213> ORGANISM: Cannabis sativa

<400> SEQUENCE: 4

Met Asn His Leu Arg Ala Glu Gly Pro Ala Ser Val Leu Ala Ile Gly
1               5                   10                  15

Thr Ala Asn Pro Glu Asn Ile Leu Leu Gln Asp Glu Phe Pro Asp Tyr
            20                  25                  30

Tyr Phe Arg Val Thr Lys Ser Glu His Met Thr Gln Leu Lys Glu Lys
        35                  40                  45

Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
65                  70                  75                  80

Met Gln Thr Leu Asp Ala Arg Gln Asp Met Leu Val Val Glu Val Pro
                85                  90                  95

Lys Leu Gly Lys Asp Ala Cys Ala Lys Ala Ile Lys Glu Trp Gly Gln
            100                 105                 110
```

-continued

```
Pro Lys Ser Lys Ile Thr His Leu Ile Phe Thr Ser Ala Ser Thr Thr
        115                 120                 125

Asp Met Pro Gly Ala Asp Tyr His Cys Ala Lys Leu Leu Gly Leu Ser
    130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Glu Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
    210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
    290                 295                 300

Asp Lys Val Glu Glu Lys Leu His Leu Lys Ser Asp Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
        355                 360                 365

Pro Gly Leu Thr Val Glu Arg Val Val Val Arg Ser Val Pro Ile Lys
    370                 375                 380

Tyr
385


<210> SEQ ID NO 5
<211> LENGTH: 101
<212> TYPE: PRT
<213> ORGANISM: Cannabis sativa

<400> SEQUENCE: 5

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30

Ile Ile Pro Ala Met Lys Asp Val Tyr Trp Gly Lys Asp Val Thr Gln
        35                  40                  45

Lys Asn Lys Glu Glu Gly Tyr Thr His Ile Val Glu Val Thr Phe Glu
    50                  55                  60

Ser Val Glu Thr Ile Gln Asp Tyr Ile Ile His Pro Ala His Val Gly
65                  70                  75                  80

Phe Gly Asp Val Tyr Arg Ser Phe Trp Glu Lys Leu Leu Ile Phe Asp
                85                  90                  95
```

-continued

```
Tyr Thr Pro Arg Lys
            100


<210> SEQ ID NO 6
<211> LENGTH: 99
<212> TYPE: PRT
<213> ORGANISM: Cannabis sativa

<400> SEQUENCE: 6

Ala Val Lys His Leu Ile Val Leu Lys Phe Lys Asp Glu Ile Thr Glu
1               5                   10                  15

Ala Gln Lys Glu Glu Phe Phe Lys Thr Tyr Val Asn Leu Val Asn Ile
            20                  25                  30

Ile Pro Ala Met Lys Asp Val Tyr Trp Gly Lys Asp Val Thr Gln Lys
        35                  40                  45

Asn Lys Glu Glu Gly Tyr Thr His Ile Val Glu Val Thr Phe Glu Ser
    50                  55                  60

Val Glu Thr Ile Gln Asp Tyr Ile Ile His Pro Ala His Val Gly Phe
65                  70                  75                  80

Gly Asp Val Tyr Arg Ser Phe Trp Glu Lys Leu Leu Ile Phe Asp Tyr
                85                  90                  95

Thr Pro Arg


<210> SEQ ID NO 7
<211> LENGTH: 95
<212> TYPE: PRT
<213> ORGANISM: Cannabis sativa

<400> SEQUENCE: 7

Ala Val Lys His Leu Ile Val Leu Lys Phe Lys Asp Glu Ile Thr Glu
1               5                   10                  15

Ala Gln Lys Glu Glu Phe Phe Lys Thr Tyr Val Asn Leu Val Asn Ile
            20                  25                  30

Ile Pro Ala Met Lys Asp Val Tyr Trp Gly Lys Asp Val Thr Gln Lys
        35                  40                  45

Asn Lys Glu Glu Gly Tyr Thr His Ile Val Glu Val Thr Phe Glu Ser
    50                  55                  60

Val Glu Thr Ile Gln Asp Tyr Ile Ile His Pro Ala His Val Gly Phe
65                  70                  75                  80

Gly Asp Val Tyr Arg Ser Phe Trp Glu Lys Leu Leu Ile Phe Asp
                85                  90                  95


<210> SEQ ID NO 8
<211> LENGTH: 415
<212> TYPE: PRT
<213> ORGANISM: Ralstonia solanacearum

<400> SEQUENCE: 8

Met Ala Phe Asn Glu Arg Val Val Asp Trp Gln Gln Val Ala Gly Ala
1               5                   10                  15

Gln Pro Asp Ala Ser Pro Glu Arg Met Ser Ala Asp Asp Pro Phe Met
            20                  25                  30

Ile Ile Tyr Thr Ser Gly Thr Thr Gly Lys Pro Lys Gly Thr Val His
        35                  40                  45

Thr His Gly Ser Phe Pro Met Lys Ile Ala His Asp Ser Ala Ile His
    50                  55                  60

Phe Asn Val Ser Pro Lys Asp Val Phe Cys Trp Pro Ala Asp Met Gly
```

-continued

```
65                  70                  75                  80

Trp Val Ala Gly Thr Leu Val Met Ser Cys Ala Leu Leu Arg Gly Ala
                85                  90                  95

Thr Leu Val Cys Tyr Asp Gly Ala Pro Asp Phe Pro Asp Trp Ser Arg
            100                 105                 110

Met Ser Arg Leu Ile Glu Arg His Arg Val Thr His Phe Gly Ser Ala
        115                 120                 125

Pro Thr Leu Ile Arg Gly Leu Ala Ser Asn Glu Ala Ile Ala Thr Gln
    130                 135                 140

Gly Asp Val Ser Ser Val Lys Leu Leu Ile Thr Ala Gly Glu Gly Ile
145                 150                 155                 160

Asp Pro Glu His Phe Leu Trp Phe Gln Lys Ala Phe Gly Gly Gly His
                165                 170                 175

Arg Pro Val Ile Asn Tyr Thr Gly Gly Thr Glu Val Ser Gly Ala Leu
            180                 185                 190

Leu Ser Ser Val Val Ile Lys Pro Ile Ser Pro Ala Gly Phe Asn Thr
        195                 200                 205

Ala Ser Pro Gly Val Ala Thr Asp Val Val Asp Ala Glu Gly His Ser
    210                 215                 220

Val Thr Gly Glu Val Gly Glu Leu Ala Ile Arg Lys Pro Phe Ile Gly
225                 230                 235                 240

Met Thr Arg Ser Phe Trp Gln Asp Asp Glu Arg Tyr Leu Asp Ser Tyr
                245                 250                 255

Trp Arg Thr Ile Pro Gly Ile Trp Val His Gly Asp Leu Ala Met Arg
            260                 265                 270

Arg Glu Asp Gly Met Trp Phe Met Met Gly Arg Ser Asp Asp Thr Ile
        275                 280                 285

Lys Leu Ala Gly Lys Arg Leu Gly Pro Ala Glu Ile Glu Asp Val Leu
    290                 295                 300

Leu Glu Leu Pro Glu Ile Ala Glu Ala Ala Ala Ile Gly Val Glu Asp
305                 310                 315                 320

Pro Val Lys Gly Gln Lys Leu Val Val Phe Val Val Ala Ser Lys Ala
                325                 330                 335

Ser Thr Ala Ser Ala Asp Ala Leu Ala Ser Val Ile Gly Lys His Val
            340                 345                 350

Asp Leu Arg Leu Gly Arg Pro Phe Arg Pro Ser Val Val His Val Val
        355                 360                 365

Ala Gln Leu Pro Lys Thr Arg Ser Ser Lys Ile Met Arg Arg Val Ile
    370                 375                 380

Arg Ser Val Tyr Thr Gly Lys Pro Ala Gly Asp Leu Ser Ser Leu Asp
385                 390                 395                 400

Asn Pro Leu Ala Leu Asp Glu Ile Arg Ser Ala Ala Ala Val Ser
                405                 410                 415


<210> SEQ ID NO 9
<211> LENGTH: 146
<212> TYPE: PRT
<213> ORGANISM: Streptomyces sp.

<400> SEQUENCE: 9

Ala Gly Arg Thr Asp Asn Ser Val Val Ile Asp Ala Pro Val Gln Leu
1               5                   10                  15

Val Trp Asp Met Thr Asn Asp Val Ser Gln Trp Ala Val Leu Phe Glu
            20                  25                  30
```

-continued

```
Glu Tyr Ala Glu Ser Glu Val Leu Ala Val Asp Gly Asp Thr Val Arg
        35                  40                  45

Phe Arg Leu Thr Thr Gln Pro Asp Glu Asp Gly Lys Gln Trp Ser Trp
    50                  55                  60

Val Ser Glu Arg Thr Arg Asp Leu Glu Asn Arg Thr Val Thr Ala Arg
65                  70                  75                  80

Arg Leu Asp Asn Gly Leu Phe Glu Tyr Met Asn Ile Arg Trp Glu Tyr
                85                  90                  95

Thr Glu Gly Pro Asp Gly Val Arg Met Arg Trp Ile Gln Glu Phe Ser
            100                 105                 110

Met Lys Pro Ser Ala Pro Val Asp Asp Ser Gly Ala Glu Asp His Leu
        115                 120                 125

Asn Arg Gln Thr Val Lys Glu Met Ala Arg Ile Lys Lys Leu Ile Glu
    130                 135                 140

Glu Ala
145


<210> SEQ ID NO 10
<211> LENGTH: 5
<212> TYPE: PRT
<213> ORGANISM: Cannabis sativa

<400> SEQUENCE: 10

Tyr Thr Pro Arg Lys
1               5
```

CANNABINOID ANALOGS AND METHODS FOR THEIR PREPARATION

CROSS-REFERENCES TO RELATED APPLICATIONS

The present application claims priority to U.S. Provisional Pat. Appl. No. 62/753,708, filed on Oct. 31, 2018, and U.S. Provisional Pat. Appl. No. 62/767,447, filed on Nov. 14, 2018, which applications are incorporated herein by reference in their entirety.

BACKGROUND OF THE INVENTION

*Cannabis sativa* varieties have been cultivated and utilized extensively throughout the world for a number of applications. Stems, branches, and leaves are used in fibers and fiber-based products; sprouts and seeds as food; seeds for inexpensive oils; flowers for aromatic, recreational, ritual and medicinal purposes; and flowers and roots for nutritional and additional medicinal and pharmaceutical applications. Indeed, many controlled clinical studies and anecdotal or open-label studies in humans have been documented that demonstrate beneficial effects of both plant extracts and purified *C. sativa* plant compounds in many human medical conditions. Beneficial activities of the cannabinoid family of compounds described from human studies range from neurological to mood/behavior disorders, and to gastrointestinal disorders as well as sleeping, appetite and fatigue problems. Other uses or potential uses include the treatment of various microbial and viral infections and the treatment of a number of cancers.

BRIEF SUMMARY OF THE INVENTION

Provided herein are compounds according to Formula I:

(I)

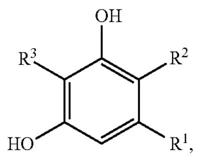

and salts and cannabinoid derivatives thereof, wherein:

$R^1$ is selected from the group consisting of $C_1$-$C_{20}$ haloalkyl, $C_1$-$C_{20}$ hydroxyalkyl, deuterated $C_1$-$C_{20}$ alkyl, tritiated $C_1$-$C_{20}$ alkyl, and $C_2$-$C_{20}$ alkenyl, $R^2$ is selected from the group consisting of $COOR^2$a and H, $R^{2a}$ is selected from the group consisting of $C_1$-$C_6$ alkyl and H, and $R^3$ is selected from the group consisting of H and a prenyl moiety.

In some embodiments, the cannabinoid derivative is a cannabidiolic acid analog, a cannabidiol analog, a $\Delta^9$-tetrahydrocannabinolic acid analog, a $\Delta^8$-tetrahydrocannabinolic acid analog, a cannabichromenic acid analog, a cannabichromene analog, a cannabinol analog, a cannabinodiol analog, a cannabinolic acid analog, a cannabivarin analog, a cannabivarinic acid analog, a $\Delta^9$-tetrahydrocannabivarin analog, a $\Delta^8$-tetrahydrocannabivarin analog, a $\Delta^9$-tetrahydrocannabivarinic acid analog, a $\Delta^8$-tetrahydrocannabivarinic acid analog, a cannabigerovarin analog, a cannabigerovarinic acid analog, a cannabichromevarin analog, a cannabichromevarinic acid analog, a cannabidivarin analog, a cannabidivarinic acid analog, a cannabitriol analog, or a cannabicyclol analog.

Also provided herein are methods of producing compounds according to Formula IV:

(IV)

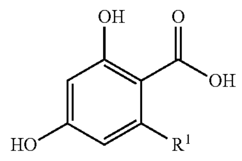

or a salt thereof, wherein $R^1$ is selected from the group consisting of $C_1$-$C_{20}$ haloalkyl, $C_1$-$C_{20}$ hydroxyalkyl, deuterated $C_1$-$C_{20}$ alkyl, tritiated $C_1$-$C_{20}$ alkyl, and $C_2$-$C_{20}$ alkenyl;

the method comprising culturing a modified recombinant host cell in a medium comprising a thioester according to Formula II;

(II)

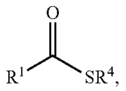

wherein $R^4$ is selected from the group consisting of a coenzyme A (CoA) moiety, a pantetheine moiety, and a cysteamine moiety, wherein the modified recombinant host cell comprises i. a first polynucleotide that encodes a synthase that converts the thioester according to Formula II and malonyl CoA to a tetraketide according to Formula III:

(III)

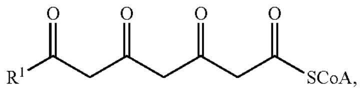

and ii. a second polynucleotide that encodes a 2-alkyl-4,6-dihydroxybenzoic acid cyclase that converts the tetraketide according to Formula III to the compound of Formula IV, and wherein the modified recombinant host cell is cultured under conditions in which products encoded by the first and second polynucleotides are expressed and the compound according to Formula IV is produced.

Compounds of Formula IV can be converted to a number of neutral and acidic cannabinoid analogs via the methods described herein.

BRIEF DESCRIPTION OF THE DRAWINGS

FIG. 1 shows one example of an enzymatic route for preparation of cannabinoid analogs according to the present disclosure.

DETAILED DESCRIPTION OF THE INVENTION

The present disclosure provides new cannabinoid compounds which are useful in a number of human therapeutic indications including neurological conditions, mood/behavior disorders, infections, and cancers. Also provided are methods for the production of pharmaceutical grade cannabinoids using sustainable, modern biopharmaceutical preparation methods.

I. DEFINITIONS

Unless otherwise defined, all terms of art, notations and other scientific terminology used herein are intended to have the meanings commonly understood by those of ordinary skill in the art to which the present application pertains. In some cases, terms with commonly understood meanings are defined herein for clarity and/or for ready reference, and the inclusion of such definitions herein should not necessarily be construed to represent a substantial difference over what is generally understood in the art.

As used herein, the terms "cannabinoid," "cannabinoid compound," and "cannabinoid product" are used interchangeably to refer to a molecule containing a polyketide moiety, e.g., olivetolic acid or another 2-alkyl-4,6-dihydroxybenzoic acid, and a terpene-derived prenyl moiety e.g., a geranyl group. Geranyl groups are derived from the diphosphate of geraniol, known as geranyl pyrophosphate or geranyl diphosphate, which can react with olivetolic acid-type compounds to form the acidic cannabinoid cannabigerolic acid (CBGA) and CBGA analogs, as shown in FIG. 1. CBGA can be converted to further bioactive cannabinoids both enzymatically (e.g., by decarboxylation via enzyme treatment in vivo or in vitro to form the neutral cannabinoid cannabigerol) and chemically (e.g., by heating).

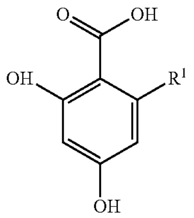

olevitolic acid $R^1$ = n-pentyl

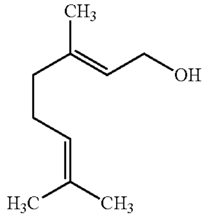

geraniol

The term cannabinoid includes acid cannabinoids and neutral cannabinoids. The term "acidic cannabinoid" refers to a cannabinoid having a carboxylic acid moiety. The carboxylic acid moiety may be present in protonated form (i.e., as —COOH) or in deprotonated form (i.e., as carboxylate —$COO^-$). Examples of acidic cannabinoids include, but are not limited to, cannabigerolic acid, cannabidiolic acid, cannabichromenic acid, and $\Delta^9$-tetrahydrocannabinolic acid. The term "neutral cannabinoid" refers to a cannabinoid that does not contain a carboxylic acid moiety (i.e., does not contain a moiety —COOH or —$COO^-$). Examples of neutral cannabinoids include, but are not limited to, cannabigerol, cannabidiol, cannabichromene, and $\Delta^9$-tetrahydrocannabinol.

The term "2-alkyl-4,6-dihydroxybenzoic acid" refers to a compound having the structure:

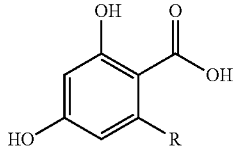

wherein R is a $C_1$-$C_{20}$ alkyl group, which can be halogenated, hydroxylated, deuterated, and/or tritiated as described herein. Examples of 2-alkyl-4,6-dihydroxybenzoic acids include, but are not limited to olivetolic acid (i.e., 2-pentyl-4,6-dihydroxybenzoic acid; CAS Registry No. 491-72-5) and divarinic acid (i.e., 2-propyl-4,6-dihydroxybenzoic acid; CAS Registry No. 4707-50-0). Olivetolic acid analogs include other 2-alkyl-4,6-dihydroxybenzoic acids and substituted resorcinols including, but not limited to, 5-halomethylresorcinols, 5-haloethylresorcinols, 5-halopropylresorcinols, 5-halohexylresorcinols, 5-haloheptyl-resorcinols, 5-halooctylresorcinols, and 5-halononylresorcinols.

The term "alkyl," by itself or as part of another substituent, refers to a straight or branched, saturated, aliphatic radical. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc.

The term "alkenyl," by itself or as part of another substituent, refers to an alkyl group, as defined herein, having one or more carbon-carbon double bonds. Examples of alkenyl groups include, but are not limited to, vinyl (i.e., ethenyl), crotyl (i.e., but-2-en-1-yl), penta-1,3-dien-1-yl, and the like. Alkenyl moieties may be further substituted, e.g., with aryl substituents (such as phenyl or hydroxyphenyl, in the case of 4-hydroxystyryl).

The terms "halogen" and "halo," by themselves or as part of another substituent, refer to a fluorine, chlorine, bromine, or iodine atom.

The term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_1$-6. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

The term "hydroxyalkyl," by itself or as part of another substituent, refers to an alkyl group where some or all of the hydrogen atoms are replaced with hydroxyl groups (i.e., —OH groups). As for alkyl and haloalkyl groups, hydroxyalkyl groups can have any suitable number of carbon atoms, such as $C_1$-6.

The term "deuterated" refers to a substituent (e.g., an alkyl group) having one or more deuterium atoms (i.e., $^2H$ atoms) in place of one or more hydrogen atoms.

The term "tritiated" refers to a substituent (e.g., an alkyl group) having one or more tritium atoms (i.e., $^3H$ atoms) in place of one or more hydrogen atoms.

The term "prenyl moiety" refers to a substituent containing at least one methylbutenyl group (e.g., a 3-methylbut-2-ene-1-yl group). In many instances prenyl moieties are synthesized biochemically from isopentenyl pyrophosphate and/or isopentenyl diphosphate, giving rise to terpene natural products and other compounds. Examples of prenyl moieties include, but are not limited to, prenyl (i.e., 3-methylbut-2-ene-1-yl), isoprenyl (i.e., 3-methylbut-3-ene-1-yl), geranyl, myrcenyl, ocimenyl, farnesyl, and geranylgeranyl.

The term "geraniol" refers to (2E)-3,7-dimethyl-2,6-octadien-1-ol (CAS Registry No. 106-24-1). The term "geranylating" refers to the covalent bonding of a 3,7-dimethyl-2,6-octadien-1-yl radical to a molecule such as a 2-alkyl-4,6-hydroxybenzoic acid. Geranylation can be conducted chemically or enzymatically, as described herein. The term "citral" refers to 3,7-dimethylocta-2,6-dienal.

"Organic solvent" refers to a carbon-containing substance that is liquid at ambient temperature and pressure and is substantially free of water. Examples of organic solvents include, but are not limited to, toluene, methylene chloride, ethyl acetate, acetonitrile, tetrahydrofuran, benzene, chloroform, diethyl ether, dimethyl formamide, dimethyl sulfoxide, and petroleum ether.

The term "acid" refers to a substance that is capable of donating a proton (i.e., a hydrogen cation) to form a conjugate base of the acid. Examples of acids include, but are not limited to, mineral acids (e.g., hydrochloric acid, sulfuric acid, and the like), carboxylic acids (e.g., acetic acid, formic acid, and the like), and sulfonic acids (e.g., methanesulfonic acid, p-toluenesulfonic acid, and the like).

As used herein, the term "treating" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; or decreasing the frequency or duration of the symptom or condition. The treatment or amelioration of symptoms can be based on any objective or subjective parameter including, e.g., the result of a physical examination.

As used herein, the term "administering" refers to oral, topical, parenteral, intravenous, intraperitoneal, intramuscular, intralesional, intranasal, subcutaneous, pulmonary, or intrathecal administration to a subject, as well administration as a suppository or the implantation of a slow-release device, e.g., a mini-osmotic pump, in the subject.

As used herein, the "term effective amount" refers to a dose that produces a therapeutic effect for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

Throughout this specification and claims, the word "comprise," or variations such as "comprises" or "comprising," will be understood to imply the inclusion of a stated integer or group of integers but not the exclusion of any other integer or group of integers.

The terms "identical" or percent "identity," in the context of two or more polypeptide sequences, refer to two or more sequences or subsequences that are the same or have a specified percentage of amino acid residues that are the same (e.g., at least 70%, at least 75%, at least 80%, 85%, 90%, 91%, 92%, 93%, 94%, 95%, 96%, 97%, 98%, 99%, or higher) identity over a specified region, when compared and aligned for maximum correspondence over a comparison window or designated region. Alignment for purposes of determining percent amino acid sequence identity can be performed in various methods, including those using publicly available computer software such as BLAST, BLAST-2, ALIGN, Megalign (DNASTAR), or Geneious software. Examples of algorithms that are suitable for determining percent sequence identity and sequence similarity the BLAST 2.0 algorithms, which are described in Altschul et al., Nuc. Acids Res. 25:3389-3402 (1977) and Altschul et al., J. Mol. Biol. 215:403-410 (1990). Thus, BLAST 2.0 can be used with the default parameters described to determine percent sequence identity.

A "conservative" substitution as used herein refers to a substitution of an amino acid such that charge, hydrophobicity, and/or size of the side group chain is maintained. Illustrative sets of amino acids that may be substituted for one another include (i) positively-charged amino acids Lys, Arg and His; (ii) negatively charged amino acids Glu and Asp; (iii) aromatic amino acids Phe, Tyr and Trp; (iv) nitrogen ring amino acids His and Trp; (v) large aliphatic nonpolar amino acids Val, Leu and Ile; (vi) slightly polar amino acids Met and Cys; (vii) small-side chain amino acids Ser, Thr, Asp, Asn, Gly, Ala, Glu, Gln and Pro; (viii) aliphatic amino acids Val, Leu, Ile, Met and Cys; and (ix) small hydroxyl amino acids Ser and Thr. Reference to the charge of an amino acid in this paragraph refers to the charge at physiological pH.

In specific cases, abbreviated terms are used. For example, the term "CBGA" refers to cannabigerolic acid. Likewise: "OA" refers to olivetolic acid; "CBG" refers to cannabigerol; "CBDA" refers to cannabidiolic acid; "CBD" refers to cannabidiol; "THC" refers to $\Delta^9$-tetrahydrocannabinol ($\Delta^9$-THC); "$\Delta^8$-THC" refers to $\Delta^8$-tetrahydrocannabinol; "THCA" refers to $\Delta^9$-tetrahydrocannabinolic acid ($\Delta^9$-THCA); "$\Delta^8$-THCA" refers to $A^8$-tetrahydrocannabinolic acid; "CBCA" refers to cannabichromenic acid; "CBC" refers to cannabichromene; "CBN" refers to cannabinol; "CBND" refers to cannabinodiol; "CBNA" refers to cannabinolic acid; "CBV" refers to cannabivarin; "CBVA" refers to cannabivarinic acid; "THCV" refers to $\Delta^8$-tetrahydrocannabivarin ($\Delta^8$-THCV); "$A^8$-THCV" refers to "$\Delta^8$-tetrahydrocannabivarin; "THCVA" refers to $\Delta^9$-tetrahydrocannabivarinic acid ($\Delta^9$-THCV); "$A^8$-THCVA" refers to $A^8$-tetrahydrocannabivarinic acid; "CBGV" refers to cannabigerovarin; "CBGVA" refers to cannabigerovarinic acid; "CBCV" refers to cannabichromevarin; "CBCVA" refers to cannabichromevarinic acid; "CBDV" refers to cannabidivarin; "CBDVA" refers to cannabidivarinic acid; "MPF" refers to multiple precursor feeding; "PKS" refers to a polyketide synthase; "GOT" refers to geranyl pyrophosphate:olivetolate geranyl transferase; "YAC" refers to yeast artificial chromosome; "IRES" or "internal ribosome entry site" means a specialized sequence that directly promotes ribosome binding and mRNA translation, independent of a cap structure; and "HPLC" refers to high performance liquid chromatography.

As used herein and in the appended claims, the singular forms "a," "and," and "the" include plural referents unless the context clearly dictates otherwise.

As used herein, the terms "about" and "around" indicate a close range around a numerical value when used to modify that specific value. If "X" were the value, for example, "about X" or "around X" would indicate a value from 0.9× to 1.1×, e.g., a value from 0.95× to 1.05×, or a value from 0.98× to 1.02×, or a value from 0.99× to 1.01×. Any reference to "about X" or "around X" specifically indicates at least the values X, 0.9×, 0.91×, 0.92×, 0.93×, 0.94×, 0.95×, 0.96×, 0.97×, 0.98×, 0.99×, 1.01×, 1.02×, 1.03×, 1.04×, 1.05×, 1.06×, 1.07×, 1.08×, 1.09×, and 1.1×, and values within this range The molecular biology techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N. Y. As appropriate, procedures involving the use of commercially available kits and reagents are generally carried out in accordance with manufacturer defined protocols and/or parameters unless otherwise noted. Before the present methods, expression systems, and uses therefore are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention, which will be limited only by the appended claims.

II. CANNABINOID ANALOGS

Provided herein are compounds according to Formula I:

(I)

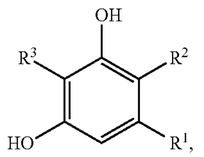

and salts and cannabinoid derivatives thereof, wherein:

$R^1$ is selected from the group consisting of $C_1$-$C_{20}$ haloalkyl, $C_1$-$C_{20}$ hydroxyalkyl, deuterated $C_1$-$C_{10}$ alkyl, tritiated $C_1$-$C_{20}$ alkyl, and $C_2$-$C_{20}$ alkenyl, $R^2$ is selected from the group consisting of $COOR^{2a}$ and H, $R^{2a}$ is selected from the group consisting of $C_1$-$C_6$ alkyl and H, and $R^3$ is selected from the group consisting of H and a prenyl moiety.

In some embodiments, $R^1$ is $C_1$-$C_{20}$ haloalkyl (e.g., $C_1$-$C_{15}$ haloalkyl or $C_1$-$C_{10}$ haloalkyl). $R^1$ can be, for example, haloethyl (containing from 1 to 5 halogen atoms), halopropyl (containing from 1 to 7 halogen atoms), halobutyl (containing from 1 to 9 halogen atoms), halopentyl (containing from 1 to 11 halogen atoms), halohexyl (containing from 1 to 13 halogen atoms), haloheptyl (containing from 1 to 15 halogen atoms), halooctyl (containing from 1 to 17 halogen atoms), and halononyl (containing from 1 to 19 halogen atoms). Examples of haloalkyl groups include, but are not limited to, chloromethyl, dichloromethyl, trichloromethyl, fluoromethyl, difluoromethyl, trifluoromethyl, 2,2,2-trichloroethyl, 2,2,2-trifluoroethyl, pentachloroethyl, pentafluoroethyl, 1,1,1,3,3,3-hexachloropropyl, 1,1,1,3,3,3-hexafluoropropyl, and the like. In some embodiments, $R^1$ is selected from $C_1$-$C_{10}$ fluoroalkyl, $C_1$-$C_{10}$ chloroalkyl, $C_1$-$C_{10}$ bromoalkyl, and $C_1$-$C_{10}$ iodoalkyl. In some embodiments, $R^1$ is selected from $C_1$-$C_{10}$ fluoroalkyl, $C_1$-$C_{10}$ chloroalkyl, and $C_1$-$C_{10}$ bromoalkyl. In some embodiments, $R^1$ is $C_1$-$C_{10}$ fluoroalkyl.

In some embodiments, $R^1$ is selected from fluoroethyl (containing from 1 to 5 fluorine atoms), fluoropropyl (containing from 1 to 7 fluorine atoms), fluorobutyl (containing from 1 to 9 fluorine atoms), fluoropentyl (containing from 1 to 11 fluorine atoms), fluorohexyl (containing from 1 to 13 fluorine atoms), fluoroheptyl (containing from 1 to 15 fluorine atoms), fluorooctyl (containing from 1 to 17 fluorine atoms), and fluorononyl (containing from 1 to 19 fluorine atoms).

In some embodiments, $R^1$ is selected from 3-fluoropropyl; 3,3,3-trifluoropropyl; 1,1-difluoropropyl; perfluoropropyl; 4-fluorobutyl; 1,1-difluorobutyl; perfluorobutyl; 5-fluoropentyl; 1,1-difluoropentyl; and perfluoropentyl.

In some embodiments, $R^1$ is selected from the group consisting of 3-fluoropropyl, 4-fluorobutyl, and 5-fluoropentyl.

In some embodiments, $R^1$ is selected from the group consisting of 3-chloropropyl, 3-bromopropyl, 3-hydroxypropyl, 4-chlorobutyl, 4-bromobutyl, 4-hydroxybutyl, 5-chloropentyl, 5-bromopentyl, 5-hydroxypentyl, 6-chlorohexyl, 6-bromohexyl, and 6-hydroxyhexyl. In some embodiments, $R^1$ is perdeutero-pentyl (i.e., $-C_5D_{11}$).

In some embodiments, $R^2$ is COOH. Compounds of Formula I wherein $R^2$ is COOH and $R^3$ is H include olivetolic acid analogs, wherein $R^1$ is halopentyl, hydroxypentyl, deuterated pentyl, or tritiated pentyl.

In some embodiments, $R^2$ is H. Compounds of Formula I wherein $R^2$ is H and $R^3$ is H include olivetol analogs, wherein $R^1$ is halopentyl, hydroxypentyl, deuterated pentyl, or tritiated pentyl.

In some embodiments, $R^2$ is $COOR^{2a}$ and $R^{2a}$ is $C_1$-$C_6$ alkyl. $R^{2a}$ can be, for example, methyl, ethyl, propyl, isopropyl, n-butyl, isobutyl, sec-butyl, tert-butyl, n-pentyl, isopentyl, n-hexyl, or branched hexyl.

In some embodiments, 2,4-dihydroxy-6-perdeuteropentylbenzoic acid; 2,4-dihydroxy-6-(5-fluoropentyl)-benzoic acid; 2,4-dihydroxy-6-(4-fluorobutyl)-benzoic acid; 6-(4-chlorobutyl)-2,4-dihydroxybenzoic acid; and/or 2,4-dihydroxy-6-(3-fluoropropyl)-benzoic acid is provided. In some embodiments, 5-perdeuteropentylbenzene-1,3-diol; 5-(5-fluoropentyl)-benzene-1,3-diol; 5-(4-fluorobutyl)-benzene-1,3-diol; 5-(4-chlorobutyl)-benzene-1,3-diol; and/or 5-(3-fluoropropyl)-benzene-1,3-diol is provided.

In some embodiments, $R^3$ is a prenyl moiety. $R^3$ can be, for example, prenyl (i.e., 2-methylbut-2-en-1-yl), geranyl (i.e., 3,7-dimethylocta-2,6-diene-1-yl), farnesyl (i.e., 3,7,11-trimethyldodeca-2,6,10-triene-1-yl), or geranylgeranyl (i.e., 3,7,11,15-tetramethylhexadeca-2,6,10,14-tetraene-1-ol). In some embodiments, the prenyl moiety is geranyl. The carbon-carbon double bonds of the prenyl moiety can be in the cis (Z) configuration or trans (E) configuration, as shown in non-limiting examples set forth below wherein the wavy line represents the point of attachment of the prenyl moiety to the compound of Formula I. In some embodiments, $R^3$ is trans-geranyl (i.e., (E)-3,7-dimethylocta-2,6-dien-1-yl).

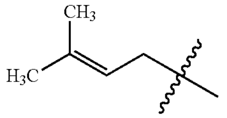

3-methylbut-2-en-1-yl

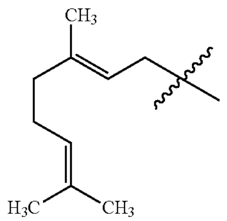

(E)-3,7-dimethylocta-2,6-diene-1-yl

-continued

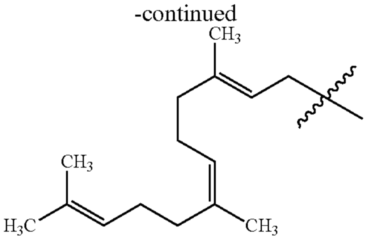

(2E,6Z)-3,7,11-trimethyldodeca-2,6,10-triene-1-yl

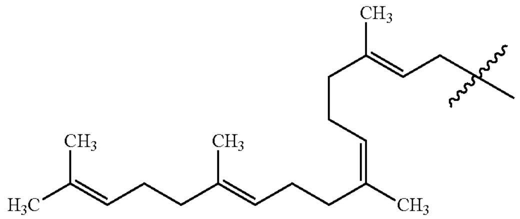

(2E,6Z,10E)-3,7,11,15-trimethylhexadeca-2,6,10,14-tetraene-1-yl

In some embodiments, the compound has a structure according to Formula Ia:

(Ia)

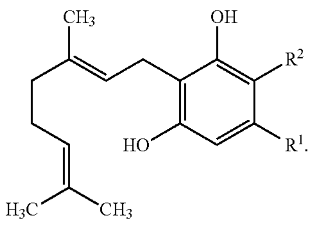

Compounds of Formula Ia wherein $R^2$ is COOH include cannabigerolic acid analogs, wherein $R^1$ is halopentyl, hydroxypentyl, deuterated pentyl, or tritiated pentyl. Compounds of Formula Ia wherein $R^2$ is H including cannabigerol analogs, wherein $R^1$ is halopentyl, hydroxypentyl, deuterated pentyl, or tritiated pentyl.

In some embodiments, 6-(4-chlorobutyl)-3-(3,7-dimethyl-octa-2,6-dienyl)-2,4-dihydroxy-benzoic acid; 3-(3,7-dimethyl-octa-2,6-dienyl)-6-(5-fluoropentyl)-2,4-dihydroxy-benzoic acid; 2-methyl-2-(4-methyl-pent-3-enyl)-7-perdeuteropentyl-2H-chromen-5-ol; 5-hydroxy-2-methyl-2-(4-methyl-pent-3-enyl)-7-perdeuteropentyl-2H-chromene-6-carboxylic acid; 7-(5-fluoropentyl)-2-methyl-2-(4-methyl-pent-3-enyl)-2H-chromen-5-ol; and/or 7-(5-chloropentyl)-2-methyl-2-(4-methyl-pent-3-enyl)-2H-chromen-5-ol is provided.

In some embodiments, cannabinoid derivatives of compounds according to Formula I and Formula Ia are provided.

In some embodiments, the cannabinoid derivative is selected from a halogenated cannabidiolic acid, a halogenated cannabidiol, a halogenated $\Delta^9$-tetrahydrocannabinolic acid, a halogenated $\Delta^8$-tetrahydrocannabinolic acid, a halogenated cannabichromenic acid, a halogenated cannabichromene, a halogenated cannabinol, a halogenated cannabinodiol, a halogenated cannabinolic acid, a cannabivarin, a halogenated cannabivarinic acid, a halogenated $\Delta^9$-tetrahydrocannabivarin, a halogenated $\Delta^8$-tetrahydrocannabivarin, a halogenated $\Delta^9$-tetrahydrocannabivarinic acid, a halogenated $\Delta^8$-tetrahydrocannabivarinic acid, a halogenated cannabigerovarin, a halogenated cannabigerovarinic acid, a halogenated cannabichromevarin, a halogenated cannabichromevarinic acid, a halogenated cannabidivarin, a halogenated cannabidivarinic acid, a halogenated cannabitriol, and a halogenated cannabicyclol.

In some embodiments, the cannabinoid derivative is selected from a deuterated cannabidiolic acid, a deuterated cannabidiol, a deuterated $\Delta^9$-tetrahydrocannabinolic acid, a deuterated $\Delta^8$-tetrahydrocannabinolic acid, a deuterated cannabichromenic acid, a deuterated cannabichromene, a deuterated cannabinol, a deuterated cannabinodiol, a deuterated cannabinolic acid, a cannabivarin, a deuterated cannabivarinic acid, a deuterated $\Delta^9$-tetrahydrocannabivarin, a deuterated $\Delta^8$-tetrahydrocannabivarin, a deuterated $\Delta^9$-tetrahydrocannabivarinic acid, a deuterated $\Delta^8$-tetrahydrocannabivarinic acid, a deuterated cannabigerovarin, a deuterated cannabigerovarinic acid, a deuterated cannabichromevarin, a deuterated cannabichromevarinic acid, a deuterated cannabidivarin, a deuterated cannabidivarinic acid, a deuterated cannabitriol, and a deuterated cannabicyclol.

In some embodiments, the cannabinoid derivative is selected from a tritiated cannabidiolic acid, a tritiated cannabidiol, a tritiated $\Delta^9$-tetrahydrocannabinolic acid, a tritiated $\Delta^8$-tetrahydrocannabinolic acid, a tritiated cannabichromenic acid, a tritiated cannabichromene, a tritiated cannabinol, a tritiated cannabinodiol, a tritiated cannabinolic acid, a cannabivarin, a tritiated cannabivarinic acid, a tritiated $\Delta^9$-tetrahydrocannabivarin, a tritiated $\Delta^8$-tetrahydrocannabivarin, a tritiated $\Delta^9$-tetrahydrocannabivarinic acid, a tritiated $\Delta^8$-tetrahydrocannabivarinic acid, a tritiated cannabigerovarin, a tritiated cannabigerovarinic acid, a tritiated cannabichromevarin, a tritiated cannabichromevarinic acid, a tritiated cannabidivarin, a tritiated cannabidivarinic acid, a tritiated cannabitriol, and a tritiated cannabicyclol.

In some embodiments, the cannabinoid derivative is selected from a hydroxy-cannabidiolic acid, a hydroxy-cannabidiol, a hydroxy-$\Delta^9$-tetrahydrocannabinolic acid, a hydroxy-$\Delta^8$-tetrahydrocannabinolic acid, a hydroxy-cannabichromenic acid, a hydroxy-cannabichromene, a hydroxy-cannabinol, a hydroxy-cannabinodiol, a hydroxy-cannabinolic acid, a cannabivarin, a hydroxy-cannabivarinic acid, a hydroxy-$\Delta^9$-tetrahydrocannabivarin, a hydroxy-$\Delta^8$-tetrahydrocannabivarin, a hydroxy-$\Delta^9$-tetrahydrocannabivarinic acid, a hydroxy-$\Delta^8$-tetrahydrocannabivarinic acid, a hydroxy-cannabigerovarin, a hydroxy-cannabigerovarinic acid, a hydroxy-cannabichromevarin, a hydroxy-cannabichromevarinic acid, a hydroxy-cannabidivarin, a hydroxy-cannabidivarinic acid, a hydroxy-cannabitriol, and a hydroxy-cannabicyclol.

Cannabinoid derivatives of compounds according to Formula I and Formula Ia include, but are not limited to, the cannabinoid derivatives set forth in Table 1. Compounds according to Formula I and Formula Ia can be converted to cannabinoid derivatives enzymatically (e.g., using cannabinoid synthases) or chemically, as described below.

TABLE 1

Cannabinoid Derivatives of Compounds According to Formula I and Formula Ia

| Cannabinoid derivative structure | Derivative name |
| --- | --- |
| 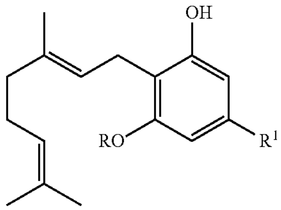 | cannabigerol [CBG] analog (R = H)<br>cannabigerol monomethyl ether [CBGM] analog (R = $CH_3$)<br>cannabigerovarin [CBGV] analog |
| 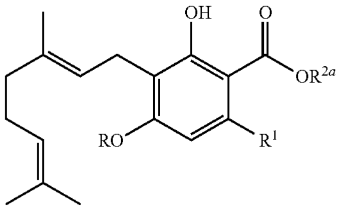 | cannabigerolic acid A [CBGA] analog (R = H)<br>cannabigerolic acid A monomethyl ether [CBGAM] analog (R = $CH_3$)<br>cannabigerovarinic acid [CBGVA] analog |
| 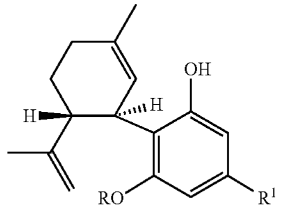 | (-)-cannabidiol [CBD] analog (R = H)<br>cannabidiol monomethyl ether [CBDM] analog (R = $CH_3$)<br>cannabidivarin [CBDV] analog<br>cannabidiorcol [CBD-C1] analog |
| 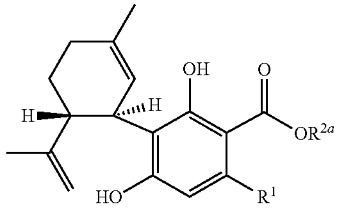 | cannabidiolic acid [CBDA] analog<br>cannabidivarinic acid [CBDVA] analog |
| 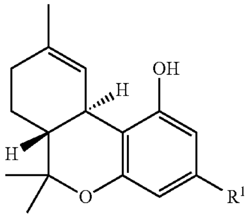 | $\Delta^9$-tetrahydrocannabinol [THC] analog<br>$\Delta^9$-tetrahydrocannabivarin [THCV] analog<br>$\Delta^9$-tetrahydrocannabiorcol [THC-$C_1$] analog |
| 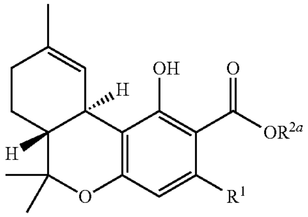 | $\Delta^9$-tetrahydrocannabinolic acid [$\Delta^9$-THCA] analog<br>$\Delta^9$-tetrahydrocannabivarinic acid [$\Delta^9$-THCVA] analog<br>$\Delta^9$-tetrahydrocannabiorcolic acid [THCOA] analog |
| 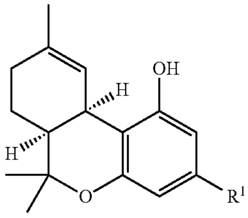 | (-)-(6aS, 10aR)-$\Delta^9$-tetrahydrocannabinol [cis-$\Delta^9$-THC] analog |

TABLE 1-continued

Cannabinoid Derivatives of Compounds According to Formula I and Formula Ia

| Cannabinoid derivative structure | Derivative name |
|---|---|
| 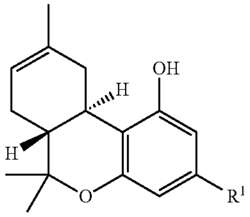 | (-)-$\Delta^8$-trans-(6aR, 10aR)-$\Delta^8$-$\Delta^8$-tetrahydrocannabinol [$\Delta^8$-THC] analog<br>(-)-$\Delta^8$-trans-(6aR, 10aR)-$\Delta^8$-$\Delta^8$-tetrahydrocannabivarin [$\Delta^8$-THCV] analog |
| 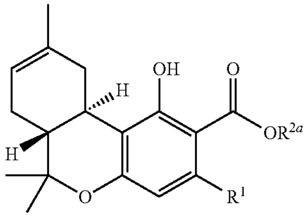 | (-)-$\Delta^8$-trans-(6aR, 10aR)-$\Delta^8$-tetrahydrocannabinolic acid [$\Delta^8$-THCA] analog<br>$\Delta^8$-tetrahydrocannabivarinic acid [$\Delta^8$-THCVA] analog |
| 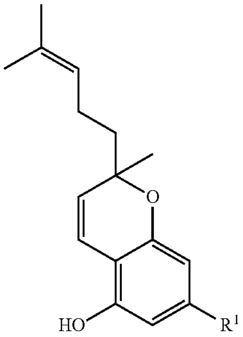 | cannabichromene [CBC] analog<br>cannabichromevarin [CBCV] analog |
| 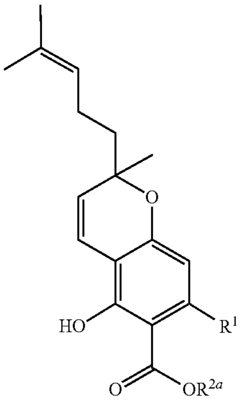 | cannabichromenic acid [CBCA] analog<br>cannabichromevarinic acid [CBCVA] analog |
| 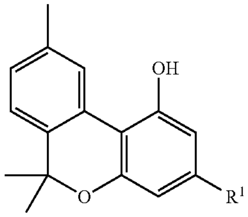 | cannabinol [CBN] analog<br>cannabinol methyl ether [CBNM] analog<br>cannabivarin [CBV] analog<br>cannabiorcol [$CBN-C_1$] analog |

TABLE 1-continued

Cannabinoid Derivatives of Compounds According to Formula I and Formula Ia

| Cannabinoid derivative structure | Derivative name |
|---|---|
| 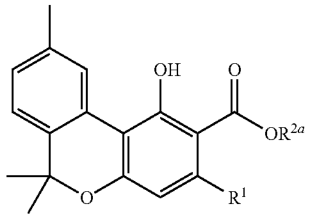 | cannabinolic acid [CBNA] analog<br>cannabivarinic acid [CBVA] analog |
| 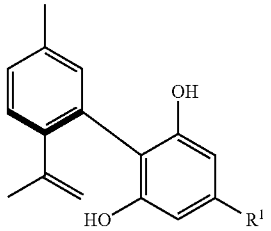 | cannabinodiol [CBND] analog<br>cannabinodivarin [CBND-C3] analog |
| 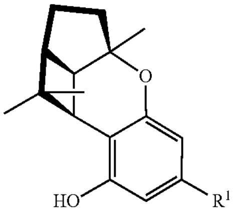 | (±)-(1aS,3aR,8bR,8cR)-cannabicyclol [CBL] analog<br>(±)-(1aS,3aR,8bR,8cR)-cannabicyclovarin [CBLV] analog |
| 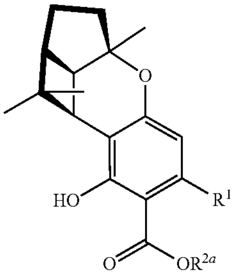 | (±)-(1aS,3aR,8bR,8cR)-cannabicyclolic acid [CBLA] analog |
| 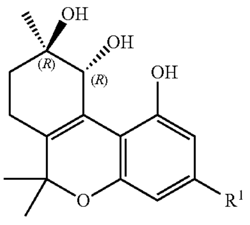 | (-)-(9R,10R)-trans-cannabitriol [(-)-trans-CBT] analog |
| 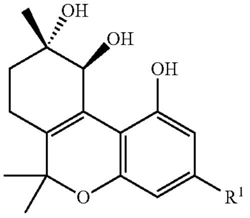 | (+)-(9S,10S)-trans-cannabitriol [(+)-trans-CBT] analog |

TABLE 1-continued

| Cannabinoid Derivatives of Compounds According to Formula I and Formula Ia | |
|---|---|
| Cannabinoid derivative structure | Derivative name |
| 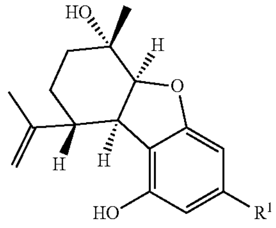 | (5aS,6S,9R,9aR)-cannabielsoin [CBE] analog |
| 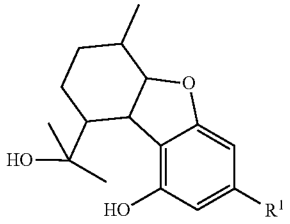 | cannabiglendol-$C_3$ [OH-iso-HHCV-$C_3$] analog |
| 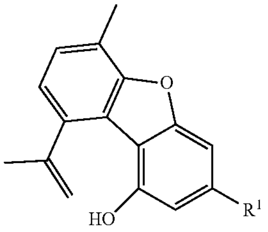 | dehydrocannabifuran [DCBF] analog |
| 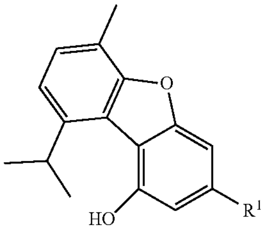 | cannabifuran [CBF] analog |
| 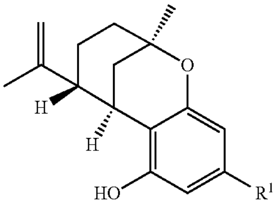 | (-)-$\Delta^7$-trans-(1R,3R,6R)-isotetrahydrocannabinol analog<br>(-)-$\Delta^7$-trans-(1R,3R,6R)-isotetrahydrocannabivarin |
| 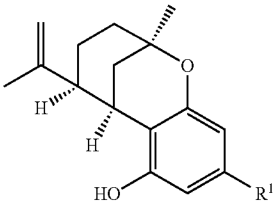 | (±)-$\Delta^7$-1,2-cis-(1R,3R,6S)-isotetrahydrocannabivarin analog |

TABLE 1-continued

| Cannabinoid Derivatives of Compounds According to Formula I and Formula Ia | |
|---|---|
| Cannabinoid derivative structure | Derivative name |
| 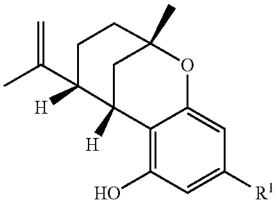 | (±)-$\Delta^7$-1,2-cis-(1S,3S,6R)-isotetrahydrocannabivarin analog |
| 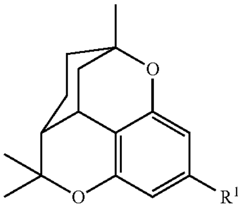 | cannabicitran [CBT] analog |
| 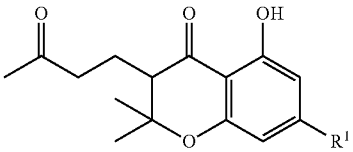 | cannabichromanone [CBCN] analog |
| 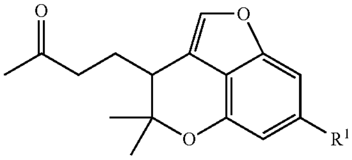 | cannabicoumaronone [CBCON] analog |

Cannabinoid derivatives of compounds according to Formula I and Formula Ia include, without limitation, analogs of CBG, CBDA, CBD, THC, $\Delta^8$-THC, THCA, $\Delta^8$-THCA, CBCA, CBC, CBN, CBND, CBNA, CBV, CBVA, THCV, THCVA, $\Delta^8$-THCA, CBGV, CBGVA, CBCV, CBCVA, CBDV and CBDVA. Further examples include, but are not limited to, the cannabichromanones, cannabicoumaronone, cannabicitran, 10-oxo-$\Delta^{6a(10a)}$-tetrahydrohydrocannabinol (OTHC), cannabiglendol, and $\Delta^7$-isotetrahydrocannabinol.

III. METHODS FOR ENZYMATIC AND CHEMOENZYMATIC PREPARATION OF CANNABINOID ANALOGS

Also provided herein are methods for the synthesis of cannabinoid analogs and intermediates thereof via metabolic pathways in engineered host cells. The term "metabolic pathway" refers to a series of two or more enzymatic reactions in which the product of one enzymatic reaction becomes the substrate for the next enzymatic reaction. At each step of a metabolic pathway, intermediate compounds are formed and utilized as substrates for a subsequent step. In some embodiments, each step of the metabolic pathway occurs in a modified recombinant cell described herein. In some embodiments, at least one step of the metabolic pathway occurs in a modified recombinant cell described herein, and at least one step of the metabolic pathway occurs outside the modified recombinant cell, in the yeast media or within an additional co-cultured modified recombinant cell.

Accordingly, some embodiments of the present disclosure provide methods for producing a compound according to Formula IV:

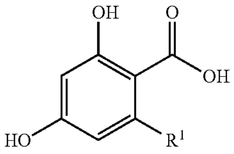

(IV)

and salts thereof, wherein $R^1$ is selected from the group consisting of $C_1$-$C_{20}$ haloalkyl, $C_1$-$C_{20}$ hydroxyalkyl, deuterated $C_1$-$C_{20}$ alkyl, tritiated $C_1$-$C_{10}$ alkyl, and $C_2$-$C_{20}$ alkenyl.

The methods include culturing a modified recombinant host cell in a medium comprising a thioester according to Formula II:

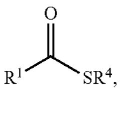

(II)

wherein $R^4$ is selected from the group consisting of a coenzyme A (CoA) moiety, a pantetheine moiety, and a cysteamine moiety, wherein the modified recombinant host cell comprises i. a first polynucleotide that encodes a synthase that converts the thioester according and malonyl CoA to Formula II to a tetraketide according to Formula III:

(III)

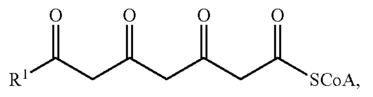

and ii. a second polynucleotide that encodes a 2-alkyl-4,6-dihydroxybenzoic acid cyclase that converts the tetraketide according to Formula III to the compound of Formula IV, and wherein the modified recombinant host cell is cultured under conditions in which products encoded by the first and second polynucleotides are expressed and the compound according to Formula IV is produced.

Olivetolic Acid Synthase

In some embodiments, the synthase is an olivetolic acid synthase. In some such embodiments, the host cell is genetically modified to express an exogenous polynucleotide that encodes olivetolic acid synthase or a variant thereof, e.g., a native homolog or ortholog, or a non-naturally occurring variant that has polyketide synthase activity. Olivetolic acid synthase (Taura et al. *FEBS Letters* 583:2061-2066, 2009), also referred to as 3, 5, 7, -trioxododecanoyl-CoA synthase, UniProtKB-B1Q2B6, is a type III PKS that that catalyzes the condensation of acyl-CoAs with three molecules of malonyl-CoA to form a 3,5,7-trioxoalkanoyl-CoA tetraketide as shown below:

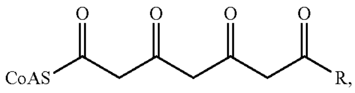

wherein "CoA" is coenzyme A and "R" is an alkyl group. When hexanoic acid is used as the starting material for cannabinoid production in naturally occurring systems, the hexanoyl-CoA is condensed with three molecules of malonyl-CoA to form 3,5,7-trioxododecanoyl-CoA (i.e., "R" is an n-pentyl group). Type III PKSs are homodimeric enzymes that act directly on acyl-CoA substrates (as opposed to acyl carrier protein-bound substrates, in the case of type I PKSs and type II PKSs). Type III PKSs are well characterized, for example, by Yu et al. (*IUBMB Life,* 64(4): 285-295, 2012).

In some embodiments, the olivetolic acid synthase polynucleotide encodes a polypeptide that comprises an amino acid sequence that has about 60% or greater identity (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:4. In some embodiments, the olivetolic acid synthase polynucleotide encodes a type III PKS comprising an amino acid sequence that has about 70%, 75%, 80%, 85%, 90%, 95%, or greater identity to the sequence set forth in SEQ ID NO:4.

The substrate specificity observed in the naturally occurring systems can be expanded to a number of starting materials with $R^1$ groups as described herein, e.g., $C_1$-$C_{20}$ haloalkyl groups, $C_1$-$C_{20}$ hydroxyalkyl groups, deuterated $C_1$-$C_{20}$ alkyl groups, tritiated $C_1$-$C_{20}$ alkyl groups, and/or $C_2$-$C_{20}$ alkenyl groups. Similarly, the thioesters employed in the methods of the invention are not limited to the coenzyme A (CoA) esters utilized in naturally occurring systems. $R^4$ may be a CoA moiety as shown below, wherein the wavy line represents the point of attached of the CoA moiety to the sulfur atom in the thioester according to Formula II:

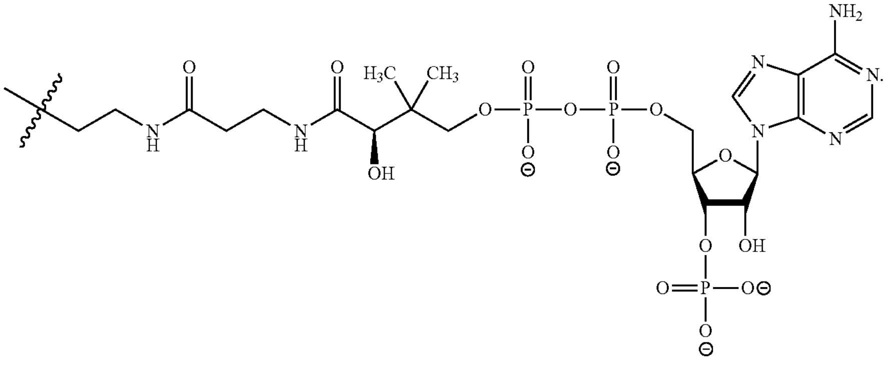

Alternatively, $R^4$ may be a pantetheine moiety:

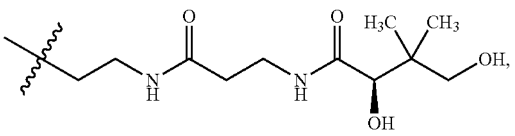 [SMILES: *CCNC(=O)CCNC(=O)[C@H](O)C(C)(C)CO]

or a cysteamine moiety:

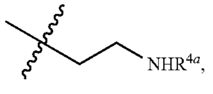

wherein the wavy line represents the point of attachment of $R^4$ to the sulfur atom in the thioester according to Formula II, and wherein $R^{4a}$ is H or acetyl (—$C(O)CH_3$). Thioesters according to Formula II can be formed enzymatically or prepared chemically as described below.

2-Alkyl-4,6-dihydroxybenzoic Acid Cyclase

Host cells used for producing compounds of Formula IV can be modified to express an exogenous polynucleotide that encodes a 2-alkyl-4,6-dihydroxybenzoic acid cyclase. In some embodiments, the 2-alkyl-4,6-dihydroxybenzoic acid cyclase is a dimeric α+β barrel (DABB) protein domain that resembles DABB-type polyketide cyclases from *Streptomyces*. Olivetolic acid cyclase is described, for example, by Gagne et al. (*Proc. Nat. Acad. Sci. USA* 109 (31): 12811-12816; 2012). The term "2-alkyl-4,6-dihydroxybenzoic acid cyclase" includes variants, e.g., a truncated or modified polypeptide, that have cyclase activity; and naturally occurring homologs or orthologs. In some embodiments, the 2-alkyl-4,6-dihydroxybenzoic acid cyclase is olivetolic acid cyclase from *C. sativa* (EC number 4.4.1.26). In some embodiments, the 2-alkyl-4,6-dihydroxybenzoic acid cyclase produces divarinic acid (see, e.g., Yang et al., *FEBS J.* 283:1088-1106, 2016). In some embodiments, the 2-alkyl-4,6-dihydroxybenzoic acid cyclase is an olivetolic acid cyclase homolog from *Arabidopsis thaliana* AtHS1 (Uniprot Q9LUV2), *Populus tremula* SP1 (P0A881), *A. thaliana* At5g22580 (Q9FK81), *S. glaucescens* TcmI cyclase (P39890), *S. coelicolor* ActVA-Orf6 (Q53908), *P. reinekei* MLMI (C5MR76), *S. nogalater* SnoaB (O54259), *M. tuberculosis* Rv0793 (086332), or *P. aeruginosa* PA3566 (Q9HY51). In some embodiments, the 2-alkyl-4,6-dihydroxybenzoic acid cyclase comprises the cyclase domain from the benH gene product (B1GSN4) of the benastatin gene cluster of *Streptomyces* spp., e.g., *Streptomyces* sp. A2991200, as set forth in SEQ ID NO:9. In some embodiments, the 2-alkyl group of the 2-alkyl-4,6-dihydroxybenzoic acid contains 1-18 carbon atoms. In some embodiments, the 2-alkyl group of the 2-alkyl-4,6-dihydroxybenzoic acid contains 1-12 carbon atoms. In some embodiments, the 2-alkyl group of the 2-alkyl-4,6-dihydroxybenzoic acid contains 1-9 carbon atoms.

In some embodiments, the polynucleotide encoding the 2-alkyl-4,6-dihydroxybenzoic acid cyclase encodes a polypeptide that has about 60% or greater identity (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:5, 6, 7, or 9. In some embodiments, the polypeptide has about 70%, 75%, 80%, 85%, 90%, 95%, or greater identity to the sequence set forth in SEQ ID NO:5, 6, 7, or 9.

Acyl-CoA Synthetase

Thioesters according to Formula II can be formed enzymatically by the host cells or chemically prior to cell culture. In some embodiments, the host cell further comprises a third polynucleotide that encodes an acyl-CoA synthetase that converts a starting material according to Formula IIa (IIa)

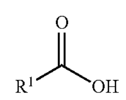

to the thioester according to Formula II, and step a) comprises culturing the host cell under conditions in which the product encoded by the third polynucleotide is expressed and the thioester according to Formula II is produced.

As used herein, the term "acyl-CoA synthetase," which may also be referred to as an "acyl-CoA synthase," an "acyl activating enzyme," or an "acyl-CoA ligase," is an enzyme that converts a carboxylic acid (e.g., an acid starting material according to Formula IIa) to an acyl-CoA thioester through a two-step process in which a carboxylate and ATP are converted to an enzyme-bound carboxyl-AMP intermediate (called an adenylate) with the release of pyrophosphate (PPi). The activated carbonyl carbon of the adenylate is coupled to the thiol of CoA, followed by enzyme release of the thioester and AMP.

Any number of acyl-CoA synthetases can be employed for formation of the thioester according to Formula II. Acyl-CoA synthetases include, but are not limited to, short-chain acyl-CoA synthetases (EC 6.2.1.1), medium chain acyl-CoA synthetases (EC 6.2.1.2), long-chain acyl-CoA synthetases (EC 6.2.1.3), and coumarate-CoA ligases (EC 6.2.1.12). Acyl-CoA synthetases typically include a 12-amino acid residue domain called the AMP-binding motif (PROSITE PS00455): [LIVMFY]-{E}-{VES}-[STG]-[STAG]-G-[ST]-[STEI]-[SG]-x-[PASLIVM]-[KR]. In the PROSITE sequence, each position in the sequence is separated by "-" and the symbol "x" means that any residue is accepted at the given location in the sequence. Acceptable amino acids for a given position are placed between square parentheses (e.g., [ST] indicates that serine or threonine are acceptable at the given location in the sequence), while amino acids which are not accepted at a given location are placed between curly brackets (e.g., {VES} indicates that any residue except valine, glutamic acid, and serine are acceptable at the given location in the sequence). The AMP binding motif has been used to classify polypeptides as acyl activating enzymes (AAEs) and contributed to the identification of the large AAE gene superfamily present in *Arabidopsis* (Shockey et al., 2003, *Plant Physiology* 132: 1065-1076), *Chlamydomonas reinhardtii, Populus trichocharpa*, and *Physcomitrella patens* (Shockey and Browse, 2011, *The Plant Journal* 66: 143-160). Acyl-CoA synthetases are also described, for example, in WO 2018/209143; by Black et al. (*Biochim Biophys Acta.* 1771(3):286-98, 2007); by Miyazawa et al. (*J. Biol. Chem* 290 (45): 26994-27011, 2015); and by Stout et al. (*Plant J.* 71(3):353-365, 2012).

In some embodiments, the acyl-CoA synthetase is from an organism that biosynthesizes resveratrol. In some embodiments, the acyl-CoA synthetase is a coumarate-CoA ligase from the genus *Morus* or the genus *Vitis*. In some embodiments, the acyl-CoA synthetase is from *Ralstonia solanacearum*. In some embodiments, the acyl-CoA synthetase from *Ralstonia solanacearum* is deleted at the N-terminus, see, e.g., SEQ ID NO:8. In some embodiments, a transmembrane domain may be deleted from the acyl-CoA synthetase.

In some embodiments, the host cell is genetically modified to express an exogenous polynucleotide that encodes a revS polypeptide from a *Streptomyces* sp. (see, e.g., Miyazawa et al., *J. Biol. Chem.* 290:26994-27001, 2015), or variant thereof, e.g., a native homolog, ortholog or non-naturally occurring variant that has acyl-CoA synthetase activity. In some embodiments, the polynucleotide encodes a polypeptide that has about 60% or greater identity (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:1. In some embodiments, the polynucleotide encodes a RevS polypeptide that has about 70%, 75%, 80%, 85%, 90%, 95%, or greater identity to the sequence set forth in SEQ ID NO:1. In some embodiments, a non-naturally occurring variant comprises one or more modifications, e.g., substitutions such as conservative substitutions, in comparison to SEQ ID NO:1, e.g., in regions outside the AMP binding motif or catalytic site.

In some embodiments, the host cell is genetically modified to express an exogenous polynucleotide that encodes an acyl activating enzyme from *Cannabis sativa* (CsAAE3) or variant thereof, e.g., a native homolog, ortholog or non-naturally occurring variant that has acyl-CoA synthetase activity. In some embodiments, the CsAAE3 polypeptide encoded by the polynucleotide comprises an amino acid sequence that has at least about 60% or greater identity (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:2. In some embodiments, the acyl-CoA synthetase polynucleotide encodes a CsAAE3, or a homolog or non-naturally occurring variant thereof, comprising an amino acid sequence that has about 70%, 75%, 80%, 85%, 90%, 95%, or greater identity to the sequence set forth in SEQ ID NO:2. In some embodiments, the non-naturally occurring variant comprises one or more modifications, e.g., substitutions such as conservative substitutions, in comparison to SEQ ID NO:2, e.g., in regions outside the AMP binding motif or catalytic site.

In some embodiments, the host cell is genetically modified to express an exogenous polynucleotide that encodes an acyl activating enzyme from *Cannabis sativa* (CsAAE1) or variant thereof, e.g., a native homolog, ortholog or non-naturally occurring variant that has acyl-CoA synthetase activity. In some embodiments, the CsAAE1 polypeptide encoded by the polynucleotide comprises an amino acid sequence that has at least about 60% or greater identity (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:3. In some embodiments, the acyl-CoA synthetase polynucleotide encodes a CsAAE1, or a homolog thereof, comprising an amino acid sequence that has about 70%, 75%, 80%, 85%, 90%, 95%, or greater identity to the sequence set forth in SEQ ID NO:3. In some embodiments, the CsAAE1 polynucleotide encodes a polypeptide from which the transmembrane domain is deleted. In some embodiments, a non-naturally occurring variant comprises one or more modifications, e.g., substitutions such as conservative substitutions, in comparison to SEQ ID NO:3, e.g., in regions outside the AMP binding motif or catalytic site.

In some embodiments, $R^1$ is selected from 4-fluorobutanoic acid; 4,4,4-trifluorobutanoic acid; 2,2-difluorobutanoic acid; perfluorobutanoic acid; 5-fluoropentanoic acid; 2,2-difluoropentanoic acid; perfluoropentanoic acid; 6-fluorohexanoic acid; 2,2-difluorohexanoic acid; and perfluorohexanoic acid.

In some embodiments, $R^1$ in starting materials according to Formula IIa is selected from the group consisting of 4-fluorobutanoic acid, 5-fluoropentanoic acid, and 6-fluorohexanoic acid.

In some embodiments, $R^1$ is selected from the group consisting of 4-chlorobutanoic acid, 4-bromobutanoic acid, 4-hydroxybutanoic acid, 5-chloropentanoic acid, 5-bromopentanoic acid, 5-hydroxypentanoic acid, 6-chlorohexanoic acid, 6-bromohexanoic acid, 6-hydroxyhexanoic acid, 7-chloroheptanoic acid, 7-bromoheptanoic acid, and 7-hydroxyheptanoic acid. In some embodiments, $R^1$ is perdeuterohexanoic acid (i.e., $D_{11}C_5COOH$).

Chemical Thioester Synthesis

Thioesters according to Formula II may contain a CoA $R^4$ moiety, a pantetheine $R^4$ moiety, or a cysteamine $R^4$ moiety. A thioester according to Formula II can be prepared enzymatically using an acyl-CoA synthetase expressed by the host cell as described above, or the thioester can be synthesized by chemically acylating CoA, pantetheine (i.e., 2,4-dihydroxy-3,3-dimethyl-N-[2-(2-sulfanylethylcarbamoyl)ethyl]butanamide), or cysteamine (i.e., 2-aminoethanethiol) with a carboxylic acid according to Formula IIa or an activated derivative thereof.

Numerous suitable carboxylic acids are commercially available or can be prepared according to known methods, including those described in *Fiesers' Reagents for Organic Synthesis* Volumes 1-28 (John Wiley & Sons, 2016), by March (*Advanced Organic Chemistry* 6th Ed. John Wiley & Sons, 2007), and by Larock (*Comprehensive Organic Transformations* 3rd Ed. John Wiley & Sons, 2018). As a non-limiting example, α-halogenated carboxylic acids may be prepared using a halogen (e.g., $Br_2$) and catalytic phosphorous in a Hell-Volhard-Zelinsky reaction. As another non-limiting example, fluorinated carboxylic acids may be prepared using—SELECTFLUOR (chloromethyl-4-fluoro-1,4-diazoniabicyclo[2.2.2]octane bis(tetrafluoroborate)) and a catalyst system containing a copper(I) bisimine complex as described by Bloom, et al. (*Angew. Chem. Int. Ed* 2012, 51, 1-5). Hydroxylation of carboxylic acids may be conducted using platinum catalysts according to the method of Kao and Sen (*J. Chem. Soc., Chem. Commun.,* 1991, 1242-1243). Deuteration of carboxylic acids may be conducted using platinum and rhodium on carbon according to the method of Yamada, et al. (*RSC Adv.,* 2015, 5, 13727-13732).

A carboxylic acid according to Formula IIa can be used in conjunction with a coupling agent for acylation of the thiol to be acylated (e.g., CoA, pantetheine, or cysteamine). Coupling agents include for example, carbodiimides (e.g., N,N'-dicyclohexylcarbodiimide (DCC), N,N'-dicyclopentylcarbodiimide, N,N'-diisopropylcarbodiimide (DIC), 1-ethyl-3-(3-dimethylaminopropyl)carbodiimide (EDC), etc.), phosphonium salts (HOBt, PyBOP, HOAt, etc.), aminium/uronium salts (e.g., pyrimidinium uronium salts such HATU, tetramethyl aminium salts, bispyrrolidino aminium salts, bispiperidino aminium salts, imidazolium uronium salts, uronium salts derived from N,N,N'-trimethyl-N'-phenylurea, morpholino-based aminium/uronium coupling reagents, antimoniate uronium salts, etc.), organophosphorus reagents (e.g., phosphinic and phosphoric acid derivatives), organosulfur reagents (e.g., sulfonic acid derivatives), triazine coupling reagents (e.g., 2-chloro-4,6-dimethoxy-1,3,5-triazine, 4-(4,6-dimethoxy-1,3,5-triazin-2-yl)-4 methylmorpholinium chloride, 4-(4,6-dimethoxy-1,3,5-triazin-2-yl)-4 methylmorpholinium tetrafluoroborate, etc.), pyridinium coupling reagents (e.g., Mukaiyama's reagent, pyridinium tetrafluoroborate coupling reagents, etc.), polymer-supported reagents (e.g., polymer-bound carbodiimide, polymer-bound TBTU, polymer-bound 2,4,6-trichloro-1,3,5-triazine, polymer-bound HOBt, polymer-bound HOSu, polymer-bound IIDQ, polymer-bound EEDQ, etc.), and the like.

Alternatively, acylation can be conducted using an activated carboxylic acid derivative such as an acid anhydride, a mixed anhydride an acid chloride, or an activated ester (e.g., a pentafluorophenyl ester or an N-hydroxysuccinimidyl ester). Typically, 1-10 molar equivalents of the carboxylic acid or activated derivative with respect to the thiol will be used. For example, 1-5 molar equivalents of the acid/acid derivative or 1-2 molar equivalents of the acid/acid derivative can be used. In some embodiments, around 1.0, 1.1, 1.2, 1.3, 1.4, or 1.5 molar equivalents of the acid/acid derivative with respect to the thiol is used to form the thioester according to Formula II.

A base can be used to promote acylation of the thiol by the carboxylic acid or the activated carboxylic acid derivative. Examples of suitable bases include potassium carbonate, sodium carbonate, sodium acetate, Huenig's base (i.e., N,N-diisopropylethylamine), lutidines including 2,6-lutidine (i.e., 2,6-dimethylpyridine), triethylamine, tributylamine, pyridine, 2,6-di-tert-butylpyridine, 1,8-diazabicycloundec-7-ene (DBU), quinuclidine, and the collidines. Combinations of two or more bases can be used. Typically, less than one molar equivalent of base with respect to the thiol will be employed in the formation of the thioester. For example, 0.05-0.9 molar equivalents or 0.1-0.5 molar equivalents of the base can be used. In some embodiments, around 0.05, 0.1, 0.15, or 0.2 molar equivalents of the base with respect to the thiol is used in conjunction with the acid/acid derivative to form the thioester according to Formula II.

Any suitable solvent can be used for forming the thioester. Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof. The acylation reaction is typically conducted at temperatures ranging from around 25° C. to about 100° C. for a period of time sufficient to form the thioester according to Formula II. The reaction can be conducted for a period of time ranging from a few minutes to several hours or longer, depending on the particular thiol and acid/acid derivative used in the reaction. For example, the reaction can be conducted for around 10 minutes, or around 30 minutes, or around 1 hour, or around 2 hours, or around 4 hours, or around 8 hours, or around 12 hours at around 40° C., or around 50° C., or around 60° C., or around 70° C., or around 80° C.

Functional groups such as the primary amine of cysteamine or the hydroxyl groups of pantetheine and CoA can be protected to prevent unwanted side reactions during the acylation step. Examples of amine protecting groups include, but are not limited to, benzyloxycarbonyl; 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Examples of hydroxyl protecting groups include, but are not limited to, benzyl; tert-butyl; trityl; tert-butyldimethylsilyl (TBDMS; TBS); 4,5-dimethoxy-2-nitrobenzyloxycarbonyl (Dmnb); propargyloxycarbonyl (Poc); and the like. Other alcohol protecting groups and amine protecting groups are known to those of skill in the art including, for example, those described by Green and Wuts (*Protective Groups in Organic Synthesis,* 4$^{th}$ Ed 2007, Wiley-Interscience, New York). The protecting groups can be removed using standard conditions so as to restore the original functional groups following the acylation step.

Prenyltransferase

In some embodiments, the recombinant host cell is further modified to express an exogenous polynucleotide that encodes a prenyltransferase that catalyzes coupling of an activated prenyl species (e.g., geranyl pyrophosphate) to a compound of Formula IV or a compound of Formula IVa, thereby forming compounds of Formula IV and Formula Va. Examples of prenyltransferases include, but are not limited to, geranylpyrophosphate:olivetolate geranyltransferase (GOT; EC 2.5.1.102) as described by Fellermeier & Zenk (*FEBS Letters* 427:283-285; 1998), as well as *Cannabis sativa* prenyltransferases described in WO 2018/200888 and WO 2019/071000. *Streptomyces* prenyltransferases including NphB, as described by Kumano et al. (*BioorgMed Chem.* 16(17): 8117-8126; 2008), can also be used in accordance with the invention. In some embodiments, the prenyltransferase is fnq26: Flaviolin linalyltransferase from *Streptomyces cinnamonensis*. In some embodiments, a host cell genetically modified to express the prenyltransferase may be a modified host cell as described below.

Accordingly, some embodiments of the disclosure provide methods that include converting a compound of Formula IV as described above to a compound of Formula V:

(VI)

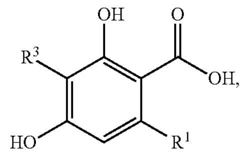

or a salt thereof, wherein $R^3$ is a prenyl moiety. $R^3$ can be, for example, geranyl, farnesyl, or geranylgeranyl, containing carbon-carbon double bonds in the cis (Z) configuration and/or trans (E) configuration. Some embodiments provide methods that include converting a decarboxylated compound of Formula IVa:

(IVa)

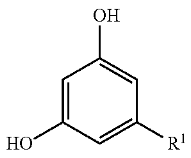

to a compound of Formula Va:

(Va)

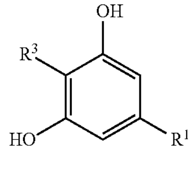

wherein $R^3$ is a prenyl moiety.

In some embodiments, the DNA construct for the geranyl pyrophosphate:olivetolate geranyltransferase encodes the wild type or a mutant enzyme with yeast-preferred codons. In some embodiments, DNA constructs that encode bacterial prenyltransferases (e.g., *Streptomyces* prenyltransferases) with relaxed substrate specificities are used (Kumano et al., 2008).

Exogenous prenyl species, such as geraniol, can be supplied to the host cells during culture and production of the prenylated compounds. Alternatively, the host cells can be cultured in media containing high levels of prenyl precursors, e.g., prenol, isoprenol, geraniol, and the like. In procedures including multiple precursor feeding (MPF), 5-carbon prenol and isoprenol can be enzymatically converted to the monophosphate level (i.e., to dimethylallyl monophosphate and isopentenyl monophosphate) and then to the diphosphate level (i.e., to dimethylallyl pyrophosphate and isopentenyl pyrophosphate) prior to coupling to form the 10-carbon geranyl pyrophosphate.

In some embodiments, the initial phosphorylation event is catalyzed by the enzyme hydroxyethylthiazole kinase. This enzyme has been described in several organisms from where the encoding genes are derived, including *E. coli, Bacillus subtilis, Rhizobium leguminosarum, Pyrococcus horikoshii, S. cerevisiae* and maize species. Further phosphorylation to the diphosphate level can be achieved by using the enzyme isoprenyl diphosphate synthase or isopentenylphosphate kinase described in U.S. Pat. No. 6,235,514. In some embodiments, chemically synthesized genes encoding this enzyme or more active mutants are derived by using the *Thermoplasma acidophilum, Methanothermobacter thermautotrophicus, Methano-caldococcus jannaschii, Mentha x piperita* or *Mangifera indica* amino acid sequences, or other homologous sequences with kinase activity. The coupling to from geranyl pyrophosphate can be catalyzed by a transferase enzyme such as geranyl pyrophosphate synthase (GPP synthase).

The 10-carbon geranyl pyrophosphate may also be generated by a kinase that phosphorylates geraniol to the monophosphate level, followed by a second kinase that gives rise to geranyl pyrophosphate. In some embodiments, the first kinase event is performed by the enzyme farnesol kinase (FOLK) (Fitzpatrick, Bhandari and Crowell, 2011; *Plant J.* 2011 June; 66(6):1078-88) or a variant thereof. This kinase enzyme is present in a number of organisms having the ability to phosphorylate 5-carbon prenols, including plants (*Arabidopsis thaliana, Camelina sativa, Capsella rubella, Noccaea caerulescens* etc.) and fungi (*Candida albicans, Talaromyces atroroseus*, etc.). Further phosphorylation of geranyl-phosphate to the geranyl pyrophosphate level can be achieved by using isopentenyl monophosphate kinase (IPK) or a variant thereof. This kinase enzyme is found in a number of bacterial and archaeal species, including but not limited to *Methanocaldococcus jannaschii*, and *Thermoplasma acidophilum*. Certain mutations in IPK (Val73, Val130, Ile140) have been reported to give rise to enhanced geranyl-phosphate kinase activity (Mabanglo et al., 2012, *ACS Chem. Biol.,* 7, 7, 1241-1246).

In some embodiments, the host cell comprises one or more additional exogenous polynucleotides selected from the three following exogenous polynucleotides: an exogenous polynucleotide that encodes a prenol and isoprenol kinase; an exogenous polynucleotide that encodes a kinase that produces dimethylallyl pyrophosphate and isopentenyl pyrophosphate when grown in the presence of exogenous prenol and isoprenol; and an exogenous polynucleotide that encodes a geranyl pyrophosphate synthase.

Chemical Prenylation

In some embodiments, the converting step is conducted in vitro. For example, the converting step can include forming a reaction mixture comprising 1) a compound according to Formula IV or Formula IVa, 2) geraniol, an activated geraniol (e.g., geranyl bromide, geranyl chloride, geranyl tosylate, geranyl mesylate, or the like), or citral, and 2) an organic solvent under conditions sufficient to produce a compound according to Formula V or Formula Va.

Any suitable organic solvent can be used in the chemical prenylation steps provided herein. Suitable solvents include, but are not limited to, toluene, methylene chloride, dichloroethane, ethyl acetate, acetonitrile, tetrahydrofuran, benzene, ethylbenzene, xylenes (i.e., m-xylene, o-xylene, p-xylene, or any combination thereof), chloroform, diethyl ether, dimethyl formamide, dimethyl sulfoxide, petroleum ether, and mixtures thereof. In some embodiments, the organic solvent is toluene, benzene, ethylbenzene, xylenes, or a mixture thereof. In some embodiments, the organic solvent is toluene. In some embodiments, the organic solvent is dichloroethane. Aqueous organic solvent mixtures (i.e., a mixture of water and a water-miscible organic solvent such as tetrahydrofuran or dimethyl formamide) can also be employed. In general, the ratio of the solvent to the compound of Formula IV or Formula IVa will range from about 1:1 to about 1000:1 by weight. The ratio of the solvent to the compound of Formula IV or Formula IVa can be, for example, about 100:1 by weight, or about 10:1 by weight, or about 5:1 weight. In certain embodiments, the compound of Formula IV or Formula IVa is present in a yeast mixture (e.g., dried yeast cells, or a wet yeast cell pellet collected from culture). In some such embodiments, the reaction mixture comprises the host cell (e.g., dried yeast cells). The ratio of solvent to yeast mixture (e.g., dried yeast cells) can range from about 1:1 to about 1000:1 by weight. The ratio of the solvent to the yeast mixture can be, for example, about 100:1 by weight, or about 10:1 by weight, or about 5:1 by weight, or about 2:1 by weight.

Any suitable amount of geraniol, activated geraniol, or citral can be used in the conversion step. In general, the reaction mixture contains at least one molar equivalent of geraniol, activated geraniol, or citral with respect to the compound of Formula IV or Formula IVa. The reaction mixture can contain, for example, from about 1 molar equivalent to about 10 molar equivalents of geraniol, activated geraniol, or citral with respect to the compound of Formula IV or Formula IVa (e.g., about 1.1 molar equivalents, or about 1.2 molar equivalents, or about 2 molar equivalents).

In some embodiments, including embodiments where geraniol or an activated geraniol is employed, the reaction mixture further comprises an acid. Any suitable acid can be used in the conversion step. Examples of suitable acids include, but are not limited to, hydrochloric acid, sulfuric acid, nitric acid, formic acid, acetic acid, trifluoroacetic acid, p-toluenesulfonic acid, methanesulfonic acid, and trifluoromethane sulfonic acid. In some embodiments, the acid is a sulfonic acid. In some embodiments, the acid is p-toluenesulfonic acid. Any suitable amount of the acid can be used in the conversion step. In general, the reaction mixture contains from about 0.01 molar equivalents of the acid (e.g., p-toluenesulfonic acid) to about 10 molar equivalents of the acid with respect to the compound of Formula IV or Formula IVa (e.g., about 0.01 molar equivalents, or about 0.1 molar equivalents, or about 1 molar equivalent).

In some embodiments, including embodiments where citral is employed, the reaction mixture further comprises an amine such as a diamine (e.g., a 1,2-diamine). Any suitable diamine or other amine can be used in the conversion step. Examples of suitable diamines include, but are not limited to, ethylene diamine, N,N-dimethylethylenediamine, N,N-diethylethylenediamine, N,N'-dimethylethylenediamine, N,N'-diphenylethylenediamine, N,N'-dibenzylethylenediamine, and N,N'-bis(2-hydroxyethyl)ethylenediamine. In some embodiments, the prenylation reaction mixture includes citral and N,N-dimethylethylenediamine. Any suitable amount of the amine can be used in the conversion step. In general, the reaction mixture contains from about 0.01 molar equivalents of the amine (e.g., N,N-dimethylethylenediamine) to about 10 molar equivalents of the amine with respect to the compound of Formula IV or Formula IVa (e.g., about 0.01 molar equivalents, or about 0.25 molar equivalents, or about 0.1 molar equivalents, or about 1 molar equivalent).

In some embodiments, chiral diamines (e.g., (1S, 2S)-1,2-di-1-naphthyl-ethylenediamine, (S)-1-[(1-methyl-2-pyrrolidinyl)methyl]piperidine, or the like) can contribute to the formation of one or more stereocenters in the prenylated cannabinoid product. For example, reaction of an olivetolic acid analog (e.g., perdeuteropentyl-olivetolic acid) with citral in the presence of a chiral diamine can afford the corresponding cannibichromene analog in stereoselective fashion. The chiral diamine can be selected to produce a particular cannabichromene analog enantiomer (e.g., (S)-2-methyl-2-(4-methylpent-3-en-1-yl)-7-perdeuteropentyl-2H-chromen-5-ol or (R)-2-methyl-2-(4-methylpent-3-en-1-yl)-7-perdeuteropentyl-2H-chromen-5-ol). Chiral diamines can also be used in the stereoselective synthesis of cannabinoids having unsubstituted alkyl groups at the $R^1$ position described herein. In some embodiments, for example, $R^1$ can be $C_1$-$C_{10}$ alkyl and forming a prenylated cannabinoid product can include reacting a 5-alkyl-resorcinol (such as olivetol or divarinol, i.e., 5-propylresorcinol) or a 2-alkyl-4,6-dihydroxybenzoic acid (such as olivetolic acid or divarinic acid) with citral in the presence of a chiral diamine to form the prenylated product (e.g., cannabichromene, cannabichromenic acid, or an analog thereof) in a stereoselective manner. Alternatively, mixtures of enantiomers (e.g., racemic mixtures) may be prepared, and the desired enantiomer may be isolated by chiral chromatography or selective crystallization.

The chemical prenylation conversion step can be conducted at any suitable temperature. Typically, the conversion step is conducted at temperatures ranging from about 20° C. to about 200° C., e.g., from about 20° C. to about 100° C., or from about 20° C. to about 80° C., or from about 20° C. to about 70° C. The conversion step is conducted for a period of time sufficient to convert the unprenylated compound to the prenylated product. Depending on factors such as the particular prenyl compound employed, the particular solvent employed, and the state of the unprenylated compound (e.g., present in a yeast mixture), the conversion time will range from a few minutes to several hours. In some embodiments, the reaction mixture will be maintained at a temperature ranging from about 20° C. to about 100° C. (e.g., about 60° C.) for a period of time ranging from about 5 minutes to about 360 minutes. In some embodiments, the reaction mixture is maintained at or around 60° C. for 60 minutes or less (e.g., about 55 minutes, or about 30 minutes, or about 15 minutes, or about 10 minutes). In some embodiments, the reaction mixture is maintained between 20° C. and 25° C. (e.g., around 23° C.) for 1 hour or more (e.g., about 60 minutes, or about 2 hours, or about 4 hours, or about 12 hours, or about 18 hours, or about 24 hours).

Host Cells

In some embodiments, host cells are modified to express an exogenous polynucleotide that encodes an acyl-CoA synthetase e.g., a revS polypeptide, CsAAE3, or CsAAE1 polypeptide; an exogenous polynucleotide that encodes an olivetolic acid synthase; and/or an exogenous polynucleotide that encodes a 2-alkyl-4,6-dihydroxybenzoic acid cyclase (e.g., olivetolic acid cyclase, including embodiments in which the olivetolic acid cyclase is truncated at the amino terminus, the carboxy terminus, or both termini) as described above.

Polynucleotides can be introduced into host cells using any methodology. In some embodiments, exogenous polynucleotides encoding two or more enzymes, e.g., two of acyl-CoA synthetase, olivetolic acid synthase, such as revS or CsAAE3, and a 2-alkyl-4,6-dihydroxybenzoic acid cyclase (e.g., olivetolic acid cyclase, or an engineered mutant thereof) as described herein are present in the same expression construct, e.g., an autonomously replicating expression vector, and expressed as a multicistronic RNA in which expression is driven by the same promoter. Thus, for example, in some embodiments, an exogenous polynucleotide encoding olivetolic acid synthase and an exogenous polynucleotide encoding 2-alkyl-4,6-dihydroxybenzoic acid cyclase (e.g., olivetolic acid cyclase), are contained in the same expression construct, e.g., and autonomously replicating expression vector, and separated by an internal ribosome entry site (IRES) such expression is drive by the same promoter to generate a discistronic mRNA. In some embodiments, the promoter is an alcohol dehydrogenase-2 promoter. In some embodiments, exogenous polynucleotides are present in the same expression construct, e.g., an autonomously replicating expression vector, and are operably linked to separate promoters. In some embodiments, exogenous polynucleotides are present in two or more expression constructs, e.g., autonomously replicating expression vectors. In some embodiments, the autonomously replicating expression vector is a yeast artificial chromosome. In some embodiments, one or more of the exogenous polynucleotides are integrated into the host genome. In some embodiments, multiple exogenous polynucleotides are introduced into the host cell by retrotransposon integration.

In some embodiments, a cannabinoid compound is produced using a compound of Formula IV or Formula IVa that is expressed within the host cell, and the host cell is further modified to express a prenyltransferase; a prenol and isoprenol kinase; a kinase to produce dimethylallyl pyrophosphate and isopentenyl pyrophosphate when grown in the presence of exogenous prenol and isoprenol; or a polynucleotide that encodes a geranyl pyrophosphate synthase as described herein. Such polynucleotides may be contained in the same or separate expression vectors as described in the preceding paragraph.

In some embodiments, the modified recombinant host cell further comprises an exogenous polynucleotide that encodes a cannabinoid synthase enzyme that catalyzes conversion of a first cannabinoid compound intermediate produced in the host cell to form a second cannabinoid compound.

In some embodiments, the host cell is a yeast or a filamentous fungus host cell such as an *Aspergillus* host cell. Genera of yeast that can be employed as host cells include, but are not limited to, cells of *Saccharomyces, Schizosaccharomyces, Candida, Hansenula, Pichia, Kluyveromyces, Yarrowia* and *Phaffia*. Suitable yeast species include, but are not limited to, *Saccharomyces cerevisiae, Schizosaccharomyces pombe, Candida albicans, Hansenula polymorpha, Pichia pastoris, P. canadensis, Kluyveromyces marxianus, Kluyveromyces lactis, Phaffia rhodozyma* and, *Yarrowia lipolytica*. Filamentous fungal genera that can be employed as host cells include, but are not limited to, cells of *Acremonium, Aspergillus, Aureobasidium, Bjerkandera, Ceriporiopsis, Chrysoporium, Coprinus, Coriolus, Corynascus, Chaertomium, Cryptococcus, Filobasidium, Fusarium, Gibberella, Humicola, Magnaporthe, Mucor, Myceliophthora,*

*Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes*, and *Trichoderma*. Illustrative species of filamentous fungal species include *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei*, and *Trichoderma viride*.

In some embodiments, the host cell is selected from the group consisting of *Saccharomyces cerevisiae, Kluyveromyces lactis, Kluyveromyces marxianus, Pichia pastoris, Yarrowia lipolytica, Hansenula polymorpha* and *Aspergillus*.

In the above embodiments, the genes may be encoded by chemically synthesized genes, with yeast codon optimization, that encode a wild type or mutant enzyme from *C. sativa, Arabidopsis thaliana* or *Pseudomonas* spp.

Promoters used for driving transcription of genes in *S. cerevisiae* and other yeasts are well known in the art and include DNA elements that are regulated by glucose concentration in the growth media, such as the alcohol dehydrogenase-2 (ADH2) promoter. Other regulated promoters or inducible promoters, such as those that drive expression of the GAL1, MET25 and CUP1 genes, are used when conditional expression is required. GAL1 and CUP1 are induced by galactose and copper, respectively, whereas MET25 is induced by the absence of methionine.

In some embodiments, one or more of the exogenous polynucleotides is operably linked to a glucose regulated promoter. In some embodiments, expression of one or more of the exogenous polynucleotides is driven by an alcohol dehydrogenase-2 promoter.

Other promoters drive strongly transcription in a constitutive manner. Such promoters include, without limitation, the control elements for highly expressed yeast glycolytic enzymes, such as glyceraldehyde-3-phosphate dehydrogenase (GPD), phosphoglycerate kinase (PGK), pyruvate kinase (PYK), triose phosphate isomerase (TPI), enolase (ENO2) and alcohol dehydrogenase-1 (ADH1). Other strong constitutive promoters that may be used are those from the *S. cerevisiae* transcription elongation factor EF-1 alpha genes (TEF1 and TEF2) (Partow et al., Yeast. 2010, (11): 955-64; Peng et al., Microb Cell Fact. 2015, (14):91-102) and the high-affinity glucose transporter (HXT7) and chaperonin (SSA1) promoters that function well under conditions of low glucose following the *S. cerevisiae* diauxic shift (Peng et al., Microb Cell Fact. 2015, (14):91-102).

In other embodiments, the host cells can increase cannabinoid production by increasing precursor pools and the like. Heterologous natural or chemically synthesized genes for enzymes such as malonyl-CoA synthase, with malonate feeding (Mutka et al., FEMS Yeast Res. 2006), and acetyl-CoA carboxylases 1 and 2 up-regulate the important malonyl-CoA for PKS biosynthesis. Similarly, acetyl-CoA synthases-1 and -2, and other gene products in the mevalonate pathway, e.g., acetoacetyl-CoA thiolase or the NphT7 gene product from *Streptomyces* sp. (Okamura et al., Proc Natl Acad Sci USA. 2010), HMG-CoA synthase, mevalonate kinase, phosphomevalonate kinase, mevalonate diphosphate decarboxylase, isopentenyl diphosphate: dimethylallyl diphosphate isomerase, HMG-CoA reductase, mutant farnesyl-pyrophosphate synthase (ERG20; Zhao et al., 2016) from *Saccharomyces* or other eukaryotic species may also be introduced on high-level expression plasmid vectors or through genomic integration using methods well known to those skilled in the art. Such methods may involve CRISPR Cas-9 technology, yeast artificial chromosomes (YACs) or the use of retrotransposons. Alternatively, if natural to the host organism, such genes may be up-regulated by genetic element integration methods known to those skilled in the art.

In yet other aspects, similar engineering may be employed to reduce the production of natural products, e.g., ethanol that utilize carbon sources that lead to reduced utilization of that carbon source for cannabinoid production. Such genes may be completely "knocked out" of the genome by deletion, or may be reduced in activity through reduction of promoter strength or the like. Such genes include those for the enzymes ADH1 and/or ADH6. Other gene "knockouts" include genes involved in the ergosterol pathway, such as ERG9 and the two most prominent aromatic decarboxylase genes of yeast, PAD1 and FDC1.

Further embodiments include genes for accessory enzymes aimed at assisting in the production of the final product cannabinoids. One such enzyme, catalase, is able to neutralize hydrogen peroxide produced by certain enzymes involved in the oxido-cyclization of CBGA and analogs, such as cannabidiolic acid synthase (Taura et al., 2007, *FEBSLett* 581: 2929-2934), $\Delta^9$-tetrahydrocannabinolic acid synthase (Sirikantaramas et al., 2004, *J. Biol. Chem.*, 279: 39767-39774.) and cannabichromenic acid synthase (Morimoto et al., 1998, *Phytochemistry* 49: 1525-1529).

In further embodiments, the engineered host cells contain up-regulated or down-regulated endogenous or heterologous genes to optimize, for example, the precursor pools for cannabinoid biosynthesis. Additional, further heterologous gene products may be expressed to give "accessory" functions within the cell. For example, overexpressed catalase may be expressed in order to neutralize hydrogen peroxide formed in the oxido-cyclization step to important acidic cannabinoids such as CBDA, $\Delta^9$-THCA and CBCA. "Accessory" genes and their expressed products may be provided through integration into the yeast genome through techniques well known in the art, or may be expressed from plasmids (also known as yeast expression vectors), yeast artificial chromosomes (YACs) or yeast transposons.

In some embodiments, host cells, e.g., yeast strains, transformed or genomically integrated with plasmids or vectors containing each of the above genes are transformed together with another expression system for the conversion of CBGA or a CBGA analog to a second acidic cannabinoid, as further explained below. In some such embodiments, the expression system is on the same vector or on a separate vector, or is integrated into the host cell genome.

The cannabinoid-producing engineered cells of the invention may be made by transforming a host cell, either through genomic integration or using episomal plasmids (also referred to as expression vectors, or simply vectors) with at least one nucleotide sequence encoding enzymes involved in the engineered metabolic pathways. As used herein the term "nucleotide sequence", "nucleic acid sequence" and "genetic construct" are used interchangeably and mean a polymer of RNA or DNA, single- or double-stranded, optionally containing synthetic, non-natural or altered nucleotide bases. A nucleotide sequence may comprise one or more segments of cDNA, genomic DNA, synthetic DNA, or RNA. In some embodiments, the nucleotide sequence is codon-optimized to reflect the typical codon usage of the host cell without altering the polypeptide encoded by the nucleotide sequence. In certain embodiments, the term "codon optimization" or "codon-optimized" refers to modifying the codon content of a nucleic acid sequence without modifying the sequence of the polypeptide encoded by the nucleic acid to enhance expression in a particular host cell. In certain embodiments, the term is meant to encompass modifying the codon content of a nucleic acid sequence as a means to control the level of expression of a polypeptide (e.g., either increase or decrease the level of expression). Accordingly, described are nucleic sequences encoding the enzymes involved in the engineered metabolic pathways. In some embodiments, a metabolically engineered cell may express one or more polypeptide having an enzymatic activity necessary to perform the steps described below. In some embodiments, the nucleotide sequences are synthesized and codon-optimized for expression in yeast according to methods described in U.S. Pat. No. 7,561,972.

For example a particular cell may comprises one, two, three, four, five or more than five nucleic acid sequences, each one encoding the polypeptide(s) necessary to produce a cannabinoid compound, or cannabinoid compound intermediate described herein. Alternatively, a single nucleic acid molecule can encode one, or more than one, polypeptide. For example, a single nucleic acid molecule can contain nucleic acid sequences that encode two, three, four or even five different polypeptides. Nucleic acid sequences useful for the invention described herein may be obtained from a variety of sources such as, for example, amplification of cDNA sequences, DNA libraries, de novo synthesis, excision of genomic segment. The sequences obtained from such sources may then be modified using standard molecular biology and/or recombinant DNA technology to produce nucleic sequences having desired modifications. Exemplary methods for modification of nucleic acid sequences include, for example, site directed mutagenesis, PCR mutagenesis, deletion, insertion, substitution, swapping portions of the sequence using restriction enzymes, optionally in combination with ligation, homologous recombination, site specific recombination or various combination thereof. In other embodiments, the nucleic acid sequences may be a synthetic nucleic acid sequence. Synthetic polynucleotide sequences may be produced using a variety of methods described in U.S. Pat. No. 7,323,320, as well as U.S. Pat. Appl. Pub. Nos. 2006/0160138 and 2007/0269870. Methods of transformation of yeast cells are well known in the art.

Fermentation Conditions

Cannabinoid production according to the methods provided herein generally includes the culturing of host cells (e.g., yeast or filamentous fungi) that have been engineered to contain the expression systems described above. In some embodiments, the carbon sources for yeast growth are sugars such as glucose, dextrose, xylose, or other sustainable feedstock sugars such as those derived from cellulosic sources, for example. In other embodiments, the carbon sources used may be methanol, glycerol, ethanol or acetate. In some embodiments, feedstock compositions are refined by experimentation to provide for optimal yeast growth and final cannabinoid production levels, as measured using analytical techniques such as HPLC. In such embodiments, methods include utilization of glucose/ethanol or glucose/acetate mixtures wherein the molar ratio of glucose to the 2-carbon source (ethanol or acetate) is between the ranges of 50/50, 60/40, 80/20, or 90/10. Feeding is optimized to both induce glucose-regulated promoters and to maximize the production of acetyl-CoA and malonyl-CoA precursors in the production strain. In some embodiments, a long-chain hydrocarbon component (e.g., decane, dodecane, oleic acid, methyl oleate, or isopropyl myristate) may be added to the culture (e.g., in amounts ranging from about 1% (w/v) to about 20% (w/v), such as 1-10% (w/v).

In some embodiments, malonyl-CoA levels can be increased by feeding malonate (sodium salt) and expressing malonyl-CoA synthase (e.g., MatB/C from *Rhizobium trifolii*, or homolog from a related organism such as *Streptomyces* sp. See, *Biochem. J.* (1999) 344: 159-166). In some embodiments, malonyl-CoA levels can be increased by overexpression of acetyl-CoA carboxylase and associated pathways in biotin biosynthesis and biotin ligation, as well as overexpression of pathways that generate acetyl-CoA, precursor to malonyl-CoA.

In additional aspects of the invention, olivetolic acid or its analogs may be obtained by chemical synthesis, or may be biosynthesized in recombinant production systems. In some embodiments, olivetolic acid and its analogs are produced at high levels in the same yeast cell strain as contains the metabolic pathways for cannabinoid production. High-level production systems for monocyclic polyketide aromatics in yeast are known in the field. See, e.g., U.S. Pat. No. 9,637,763. In other embodiments, media from yeast strains that are producing high levels of olivetolic acid or its analogs can be concentrated and used as a highly compatible feedstock in the MPF procedure for cannabinoid manufacture.

Fermentation methods may be adapted to a particular yeast strain due to differences in their carbon utilization pathway or mode of expression control. For example, a *Saccharomyces* yeast fermentation may require a single glucose feed, complex nitrogen source (e.g., casein hydrolysates), and multiple vitamin supplementation. This is in contrast to the methylotrophic yeast *Pichia pastoris* which may require glycerol, methanol, and trace mineral feeds, but only simple ammonium (nitrogen) salts, for optimal growth and expression. See, e.g., Elliott et al. J. Protein Chem. (1990) 9:95 104, U.S. Pat. No. 5,324,639 and Fieschko et al. Biotechnol. Bioeng. (1987) 29:1113 1121. Culture media may contain components such as yeast extract, peptone, and the like. The microorganisms can be cultured in conventional fermentation modes, which include, but are not limited to, batch, fed-batch, and continuous flow.

In some embodiments, the rate of glucose addition to the fermenter is controlled such that the rate of glucose addition is approximately equal to the rate of glucose consumption by the yeast; under such conditions, the amount of glucose or ethanol does not accumulate appreciably. The rate of glucose addition in such instances can depend on factors including, but not limited to, the particular yeast strain, the fermentation temperature, and the physical dimensions of the fermentation apparatus.

For the MPF procedure, in batch mode, the precursors olivetolic acid (or an olivetolic acid analog such as another 2-alkyl-4,6-dihydroxybenzoic acid), prenol, isoprenol or geraniol may be present in concentrations of between 0.1 and 50 grams/L (e.g., between 1 and 10 g/L). In fed-batch mode, the precursors may be fed slowly into the fermentation over between 2 and 20 hours, such that a final addition of between 1 and 100 grams/L (e.g., between 1 and 10 grams/L, or between 10 and 100 grams/L) of each requisite precursor occurs.

Similarly, carboxylic acid starting materials (including substituted carboxylic acids, e.g., halogenated carboxylic acids, deuterated carboxylic acids, tritiated carboxylic acids, and hydroxylated carboxylic acids) such as substituted hexanoic acids, substituted butanoic acids, substituted pentanoic acids, and the like may be present in concentrations of between 0.1 and 50 grams/L (e.g., between 1 and 10 g/L). In fed-batch mode, the carboxylic acid may be fed slowly into the fermentation over between 2 and 72 hours (e.g., between 15 and 60 hours), such that a final addition of between 1 and 100 grams/L (e.g., between 1 and 10 grams/L, or between 10 and 100 grams/L) of the carboxylic acid occurs.

Culture conditions such as expression time, temperature, and pH can be controlled so as to afford target cannabinoid intermediates (e.g., olivetolic acid analogs) and/or target cannabinoid products (e.g., CBGA analogs, CBG analogs) in high yield. Host cells are generally cultured in the presence of starting materials, such as hexanoic acid, prenol, isoprenol, or the like, for periods of time ranging from a few hours to a day or longer (e.g., 24 hours, 30 hours, 36 hours, or 48 hours) at temperatures ranging from about 20° C. to about 40° C. depending on the particular host cells employed. For example, *S. cerevisiae* may be cultured at 25-32° C. for 24-40 hours (e.g., at 30° C. for 30 hours). The pH of culture medium can be maintained at a particular level via the addition of acids, bases, and/or buffering agents. In certain embodiments, culturing yeast at a pH of 6 or higher can reduce the production of unwanted side products such as olivetol. In some embodiments, the pH of the yeast culture ranges from about 6 to about 8. In some embodiments, the pH of the yeast culture is about 6.5. In some embodiments, the pH of the yeast culture is about 7. In some embodiments, the pH of the yeast culture is about 8.

In some embodiments, a recombinant yeast cell is genetically modified such that it produces, when cultured in vivo in a suitable precursor-containing media as described above, the cannabinoid product of interest or an intermediate at a level of at least about 0.1 g/L, at least about 0.25 g/L, at least about 0.5 g/L, at least about 0.75 g/L, at least about 1 g/L, at least about 1.5 g/L, at least about 2 g/L, at least about 2.5 g/L, at least about 3 g/L, at least about 3.5 g/L, at least about 4 g/L, at least about 4.5 g/L, at least about 5 g/L, at least about 5.5 g/L, at least about 6 g/L, at least about 7 g/L, at least about 8 g/L, at least about 9 g/L, or at least 10 g/L. In some embodiments, a recombinant yeast cell is genetically modified such that it produces, when cultured in vivo in a suitable medium, the cannabinoid product of interest or an intermediate at a level of at least about 20 g/L, at least about 30 g/L, at least about 50 g/L, or at least about 80 g/L.

Cannabinoid production may be carried out in any vessel that permits cell growth and/or incubation. For example, a reaction mixture may be a bioreactor, a cell culture flask or plate, a multiwell plate (e.g., a 96, 384, 1056 well microtiter plates, etc.), a culture flask, a fermenter, or other vessel for cell growth or incubation. Biologically produced products of interest may be isolated from the fermentation medium or cell extract using methods known in the art. For example, solids or cell debris may be removed by centrifugation or filtration. Products of interest may be isolated, for example, by distillation, liquid-liquid extraction, membrane evaporation, adsorption, or other methods.

Conversion of 2-alkyl-4,6-dihydroxybenzoic Acids Acid to Cannabinoid Products Also provided herein are methods for producing cannabinoid products. In some embodiments, the methods include expressing a cannabinoid starting material in a yeast cell, wherein the yeast cell is genetically modified to express the cannabinoid starting material, isolating the yeast cell, and converting the cannabinoid starting material to the cannabinoid product in the isolated yeast cell. The cannabinoid starting material can be an acidic cannabinoid, a neutral cannabinoid, or a cannabinoid precursor such as olivetolic acid or another 2-alkyl-4,6-dihydroxybenzoic acid. Converting the cannabinoid starting material can be conducted using the procedures described herein (e.g., chemical or enzymatic geranylation, thermal or enzymatic decarboxylation, etc.) or can be modified according to the identity of the particular cannabinoid starting material or the particular cannabinoid product. The cannabinoid starting material can be expressed, for example, using any of the expression systems described above. Isolating the yeast cells can optionally include: collecting yeast cells from culture media by centrifugation, filtration, or other means; washing yeast cells to remove culture media or other components; removing at least a portion of liquid (e.g., culture media) from the cells; and/or drying the cells (e.g., by lyophilization or other means). Isolated yeast cells can be directly subjected to reaction conditions for forming the cannabinoid products. For example, yeast cells can be combined directly with solvents and other reagents as described below.

In some embodiments, an acidic species, e.g., a compound according to Formula V or a cannabinoid derivative thereof, is the cannabinoid product. In some embodiments, the method further includes converting the acidic species to a decarboxylated cannabinoid product, e.g., a compound of Formula Va or a cannabinoid derivative thereof. The final cannabinoid product can therefore be a neutral cannabinoid or an acidic cannabinoid. In some embodiments, conversion of an intermediate compound, e.g., a halogenated CBGA, to another cannabinoid is carried out via physical or chemical processes such as heating, auto-oxidation or UV light treatment. For example, the methods can include the decarboxylation of an acidic cannabinoid, either within the engineered yeast cells or following their full or partial purification through the action of heat or through the action of a wild-type or mutant decarboxylase enzyme contacting the cannabinoid acid in vivo or in vitro. Decarboxylation of the acidic cannabinoids provides corresponding neutral cannabinoids. As a non-limiting example, decarboxylation of a halogenated CBGA, wherein $R^1$ is haloalkyl, provides the corresponding halogenated CBG.

Additional chemical transformations may be performed on the cannabinoids formed to make fully non-natural analogs such as esters, ethers and halogenated derivatives, either for use as pro-drugs, or more active or bioavailable drug substances. In some embodiments, this chemistry may be performed on whole yeast cells that harbor the biosynthetic cannabinoid substrates in order to avoid unnecessary purification steps prior to formation of the desired final product.

In some embodiments, a first cannabinoid product, which is a compound of Formula V or Formula Va, is converted to a second cannabinoid product through the action of a wild type or mutant cannabinoid synthase or a wild type or mutant cannabinoid acid synthase, either within the same engineered host cell or through co-culturing with two or more recombinant host cell strains, e.g., yeast strains. For example, the expression system can encode *C. sativa* THCA synthase, *C. sativa* CBDA synthase, and/or *C. sativa* CBCA synthase. In some embodiments, the synthase is a homolog from hops, e.g., a CBDA synthase homolog from hops. A CBGA analog can be converted enzymatically to the corresponding CBDA, THCA and CBCA analogs with the enzymes CBDA synthase, THCA synthase and CBCA synthase respectively; the enzymatic conversion can be conducted in vivo or ex vivo.

In some embodiments, an acidic cannabinoid, e.g., a halogenated CBGA or a halogenated CBDA, may be decarboxylated to form a neutral cannabinoid compound, e.g., a halogenated CBG or a halogenated CBD, using a decarboxylase, e.g., *Aspergillus nidulans* orsB decarboxylase. Alternatively, an acidic cannabinoid can be decarboxylated by maintaining the acidic cannabinoid at an elevated temperature (e.g., around 40° C., 50° C., or 100° C.) for periods of time ranging from a few minutes to several hours.

IV. PHARMACEUTICAL COMPOSITIONS

Also provided herein are pharmaceutical compositions containing one or more cannabinoid derivatives as described above, or one or more pharmaceutically acceptable salts thereof, and one or more pharmaceutically acceptable excipients.

The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

The pharmaceutical compositions can be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butanediol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Aqueous suspensions contain the active materials in admixture with excipients suitable for the manufacture of aqueous suspensions. Such excipients include, but are not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the active ingredient in a vegetable oil, for example, *arachis* oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules (suitable for preparation of an aqueous suspension by the addition of water) can contain the active ingredient in admixture with a dispersing agent, wetting agent, suspending agent, or combinations thereof. Additional excipients can also be present.

The pharmaceutical compositions can also be in the form of oil-in-water emulsions. The oily phase can be a vegetable oil, for example olive oil or *arachis* oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Pharmaceutical compositions containing compounds can also be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semi-permeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Compositions for pulmonary administration also include, but are not limited to, dry powder compositions containing a cannabinoid derivative as described herein. The compositions for pulmonary administration can be inhaled from any suitable dry powder inhaler device known to a person skilled in the art. In certain instances, the compositions may be conveniently delivered in the form of an aerosol spray from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound(s) and a suitable powder base, for example, lactose or starch.

The cannabinoid derivatives provided herein can also be administered topically as a solution, ointment, cream, gel, suspension, eye-drops, and the like. Still further, transdermal delivery of the cannabinoid derivatives can be accomplished by means of iontophoretic patches and the like. The cannabinoid derivatives can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

V. METHODS OF TREATING CANNIBINOID RECEPTOR-MEDIATED DISEASE

Also provided herein are methods for treating diseases, conditions, and/or disorders, including those mediated by cannabinoid receptor activity. The methods include administering an effective amount of a cannabinoid derivative as described above to a subject in need thereof. The methods can be used to treat a number of conditions including, but not limited to, pain; skin conditions; muscular conditions including, but not limited to, muscular dystrophy; metabolic syndromes such as type 2 diabetes, dyslipidemia, and obesity; eating disorders; gastrointestinal disorders; allergy; asthma; chronic obstructive pulmonary disorder; glaucoma; cardiovascular diseases or disorders such as hypertension, congestive heart failure, cardiac hypertrophy, peripheral artery disease, atherosclerosis, stroke, myocardial infarction, and cardiotoxicity associated with chemotherapy; fatty liver disease (steatohepatitis) and non-alcoholic fatty liver disease; kidney disease; diseases or disorders characterized by an addiction component such as smoking addiction or withdrawal, alcohol addiction or withdrawal, and drug addiction or withdrawal; bone diseases or disorders such as osteoporosis, Paget's disease of bone, and bone cancer; cancers including but not limited to breast cancer; inflammatory diseases or autoimmune diseases such as rheumatoid arthritis, inflammatory bowel disease, and psoriasis; Tourette's syndrome; psychiatric diseases or disorders such as depression, anxiety, mania, schizophrenia; sleep disorders (e.g., insomnia); fatigue; disorders or diseases associated with memory impairment and/or loss of cognitive function such as Parkinson's disease, Alzheimer's disease, and dementia; multiple sclerosis; epilepsy; spinal injury; and infections such as bacterial, fungal, and viral infections.

The compounds can be administered at any suitable dose in the methods. In general, the compounds are administered at a dose ranging from about 0.1 milligrams to about 1000 milligrams per kilogram of a subject's body weight (i.e., about 0.1-1000 mg/kg). The dose of a compound can be, for example, about 0.1-1000 mg/kg, or about 1-500 mg/kg, or about 25-250 mg/kg, or about 50-100 mg/kg. The dose can be about 1, 2, 3, 4, 5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 1000 mg/kg.

The dosages can be varied depending upon the requirements of the patient, the severity of the disorder being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the condition or disorder.

Administration can be conducted for a period of time which will vary depending upon the nature of the particular disorder, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the disorder. The dosage can either be increased in the event the patient does not respond significantly to a particular dosage level, or the dose can be decreased if an alleviation of the symptoms of the disorder is observed, or if the disorder has been ablated, or if unacceptable side effects are seen with a particular dosage.

A therapeutically effective amount of a cannabinoid derivative can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the disorder goes into remission or generally improves, the dosage may be maintained or kept at lower than maximum amount. If the condition or disorder relapses, the first dosage regimen can be resumed until an improvement is seen, and the second dosing regimen can be implemented again. This cycle can be repeated multiple times as necessary.

Additional active agents or therapies can be co-administered or otherwise combined with the cannabinoid derivative (s). Additional active agents and therapies suitable for use in the methods include, but are not limited to, compounds used in the treatment of type-2 diabetes and obesity, such as insulin and insulin analogues, dipeptidyl peptidase-4 (DPP-4) inhibitors, glucagon-like peptide-1 analogues, hypoglycemic agents, such as alpha-glucosidase inhibitors, biguanides, sulfonyl ureas, thiazolidinediones, weight loss therapies, such as appetite suppressing agents, serotonin reuptake inhibitors, noradrenaline reuptake inhibitors, $\beta_3$-adrenoceptor agonists, and lipase inhibitors. Compounds used in the treatment of cardiovascular disease and dysfunction can also be used in the methods, including, but not limited to, diuretics, angiotensin-converting enzyme (ACE) inhibitors, angiotensin II antagonists, beta-blockers, calcium antagonists, such as nifedipine, HMG-CoA-reductase inhibitors, such as statins, digoxin, aldosterone antagonists, and organic nitrates. Other lipid modulating agents including, but not limited to, fibrates and bile acid-binding resins can be used in the methods. The cannabinoid derivative(s) can be used with compounds used to assist smoking cessation including, but not limited to, norepinephrine-dopamine reuptake inhibitors such as bupropion.

Compounds used in the treatment of bone diseases and disorders can be used in the methods in combination with the cannabinoid derivative(s). Such compounds include, but are not limited to, anti-resorptive agents such as bisphosphonates, anabolic agents such as parathyroid hormone, RANKL inhibitors such as denosumab; and estrogen replacement and selective estrogen receptor modulators such as raloxifene. Agents used in the treatment of cancer can also be used in combination with the cannabinoid derivative(s). Examples of anti-cancer agents include, but are not limited to, chemotherapeutic agents (e.g., carboplatin, paclitaxel, pemetrexed, or the like), tyrosine kinase inhibitors (e.g., erlotinib, crizotinib, osimertinib, or the like), and immunotherapeutic agents (e.g., pembrolizumab, nivolumab, durvalumab, atezolizumab, or the like).

Compounds used in the treatment of a disease or disorder with an inflammatory or autoimmune component can be used in combination with the cannabinoid derivative(s). Such compounds include non-steroidal anti-inflammatory drugs (NSAIDs); disease-modifying anti-rheumatic drugs such as immunosuppressants; anti-TNF agents, such as infliximab, etanercept, and adalimumab; and anti B-cell therapies, such as rituximab.

Compounds used in the treatment of psychiatric diseases and disorders can be used in the methods in combination with the cannabinoid derivative(s). Such compounds include as GABAA modulators, such as benzodiazepines; $5HT_{1A}$ receptor agonists, such as buspirone; beta blockers; antipsychotics, such as dopamine receptor blockers and other drugs which modulate monoamine receptors, transporters or metabolism, such as tricyclic antidepressants, selective serotonin reuptake inhibitors, and monoamine oxidase inhibitors; lithium; and anti-epileptic drugs, such as those which block sodium channels, those which block T-type calcium channels, or those which block GABA transaminase or reuptake, including phenytoin, carbamazepine, valproate and vigabatrin. Compounds used in the treatment of a disease or disorder characterized by impairment of memory and/or loss of cognitive function can also be used in the methods, including, but not limited to such dopamine agonists and anticholinesterases.

Examples of antibiotics that can be used with the cannabinoid derivative(s) in the treatment of bacterial infections include, but are not limited to: quinolones (e.g., moxifloxacin, gemifloxacin, ciprofloxacin, oflaxacin, trovafloxacin, sitafloxacin, and the like), β-lactams (e.g., penicillins such as amoxicillin, amoxacilin-clavulanate, piperacillin-tazobactam, penicillin G, and the like; and cephalosporins such as ceftriaxone and the like), macrolides (e.g., erythromycin, azithromycin, clarithromycin, and the like), aminoglycosides (e.g., amikacin, gentamicin, kanamycin, neomycin, netilmicin, tobramycin, and the like), monobactams (e.g., aztreonam and the like). carbapenems (e.g., doripenem, imipenem, meropinem, ertapenem, and the like), thiazolides (e.g., tizoxanidine, nitazoxanidine, RM 4807, RM 4809, and the like), tetracyclines (e.g., tetracycline, minocycline, doxycycline, eravacycline, and the like), lincosamides (e.g., lincomycin, clindamycin, and the like), sulfonamides (e.g., trimethoprim, sulfamethoxazole, and the like), and nitroimidazoles (e.g., metronidazole, satranidazole, and the like). Examples of antiviral agents that can be used with the cannabinoid derivative(s) in the treatment of viral infections include, but are not limited to: viral uncoating inhibitors (e.g., amantadine, rimantadine, and the like), neuraminidase inhibitors (e.g., oseltamivir, zanamivir, laninamivir, and peramivir), reverse transcriptase inhibitors (e.g., tenofovir, stavudine, zidovudine, zalcitabine, emtricitabine, lamivudine, and the like), and protease inhibitors (e.g., ritonavir, indinavir, boceprivir, and the like), and polynucleotide synthesis inhibitors (e.g., sofosbuvir, dasabuvir, and the like).

VI. EXAMPLES

Example 1. Production of 2,4-dihydroxy-6-perdeuteropentylbenzoic Acid and 5-perdeuteropentylbenzene-1,3-diol in *S. cerevisiae*

The *S. cerevisiae* ADH2 promoter was chemically synthesized and fused to a synthetic gene for a mutated *C. sativa* acyl-activating enzyme-1 (CsAAE1 ΔTM) in which the transmembrane domain coding sequences (amino acids 245 to 267) were deleted. An *S. cerevisiae* ADH2 terminator sequence was also fused to the gene sequence immediately subsequent to the synthetic stop codons. The expression cassette was cloned into a yeast expression vector containing the URA3 selectable marker. Similarly, synthetic genes for the acyl-activating enzymes CsAAE3 (from *C. sativa*) and revS (a middle chain fatty acyl-CoA ligase from *Streptomyces* sp. SN-593) were cloned into separate URA3 vectors. Each URA3-based vector was transformed into competent *Saccharomyces cerevisiae* InvSc1 (MATa alpha his3D1 leu2 trp1-289 ura3-52) cells (Invitrogen) that were previously transformed with selectable marker LEU2-based vectors containing the *C. sativa* olivetolic acid synthase/tetraketide synthase (OAS/TKS) gene fused, via the *S. cerevisiae* p150 internal ribosome entry site (IRES) and a human ubiquitin gene, to a number of individually mutated *C. sativa* olivetolic acid cyclase genes, and to a synthetic gene encoding the *Arabidopsis thaliana* cyclase enzyme AtHS1.

Transformed cells were plated on minimal agar plates (6.7 g/L yeast nitrogen base without amino acids or ammonium sulfate (DIFCO), 20 g/L glucose, 20 g/L agar) containing amino acids for selection based on uracil and leucine prototrophy. Transformants were picked and grown for 24 hours in uracil- and leucine-deficient minimal medium. Plasmid DNA was isolated from the transformants and analyzed by restriction digestion analysis to confirm identity.

A successful transformant for each strain was used to inoculate 2 mL of uracil- and leucine-deficient minimal medium that was grown overnight at 30° C. in an orbital shaker. A 500-μL aliquot of this culture was used to inoculate 50 mL of the same media and the culture was grown at 30° C. in a shaker for 24 h. The culture was similarly inoculated into 300 mL of the same media and, after overnight growth, was transferred into an oxygen-, feed-, and agitation-controlled 7-liter fermenter (Eppendorf) containing 1.2 L 2×YEP medium (Wobbe, in *Current Protocols in Molecular Biology*, Supplement 34:13.0.1-13.13.9 (Wiley, 1996)) (20 g/L yeast extract, 40 g/L peptone).

After approximately 16 hours post inoculation, following consumption of all residual glucose, 0.2 grams of perdeuterated hexanoic acid ($D_{11}$-HA) was added directly into the fermentor, and the culture was fed with 2×YEPD that contained 14.3% glucose, 3.5% sodium acetate and 0.8 grams $D_{11}$-HA through to an elapsed fermentation time of 72 hours.

Cells were collected by centrifugation of 500-μL aliquots of the culture taken after 24, 48, and 72 hours of growth and lysed by boiling in 50 μL of 2×SDS gel loading buffer for about 2 minutes. The cell lysates were analyzed by loading onto 4-20% SDS-PAGE gels. Bands corresponding to the expected sizes of the encoded enzymes were observed.

For further quantitation and analog verification, cells were separated from the media by centrifugation, the media was acidified with glacial acetic acid, and the deuterated products were extracted using ethyl acetate. The products were further purified by column chromatography, or using Sep-Pak C18 cartridges with acetonitrile/formic acid elution, and subjected to NMR and mass spectroscopy analysis.

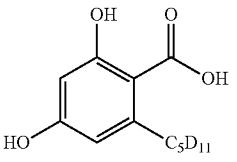

2,4-Dihydroxy-6-perdeuteropentylbenzoic acid (1). LC-MS/ESI: Calcd. [$C_{12}H_8D_{11}O_4$] 235.17; Found [M+H] 236.23, [M–H] 234.05, [M–H—$CO_2$] 190.15. $^1$H-NMR ($MeOH-D_4$, 300 MHz): δ 6.13 (1H, d, J=2.4 Hz), 6.18 (1H, d, J=2.4 Hz).

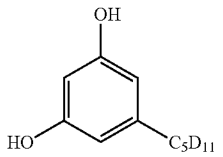

5-Perdeuteropentylbenzene-1,3-diol (2). LC-MS/ESI: Calcd. [$C_{11}H_5D_{11}O_2$]191.18; Found [M+H] 192.35.

High levels of the analogs were found to be biosynthesized using the various acyl-activating enzymes: revS (>40 mg/L); CsAAE3 (~20-30 mg/L); CsAAE1 ATM (3-4 mg/L). Product distribution of olivetolic acid to olivetol analog varied with the actual length of the mutated cyclase used, with the AtHS1 cyclase giving essentially all olivetol analog (5-perdeuteropentylbenzene-1,3-diol).

Example 2. Production of 2,4-dihydroxy-6-(5-fluoropentyl)-benzoic acid, 2,4-dihydroxy-6-(4-fluorobutyl)-benzoic acid, 5-(5-fluoropentyl)-benzene-1,3-diol and 5-(4-fluorobutyl)-benzene-1,3-diol in *S. cerevisiae*

Strains expressing the acyl-activating enzymes revS and CsAAE3, as described in Example 1, were grown in 4 mL of selective media at 30° C. for 24 h and then inoculated into 1×YPD, giving a total of 40 mL of cell culture volume. After 30 h of growth at 30° C., either 6-fluorohexanoic acid or 5-fluoropentanoic acid were added to the cultures to give a total concentration of 2 mM, and the cultures were grown at 30° C. for a further 48 h. Analog production was monitored by HPLC and purification was accomplished as above. Yields of 2,4-dihydroxy-6-(4-fluorobutyl)-benzoic acid were around 5 mg/L, whereas yields of 2,4-dihydroxy-6-(5-fluoropentyl)-benzoic acid were around 60 mg/L.

2,4-dihydroxy-6-(4-fluorobutyl)-benzoic acid. LC-MS/ESI. Calcd. [$C_{11}H_{13}FO_4$]228.08; Found [M–H] 226.95, [M–H—$CO_2$] 183.05.

2,4-dihydroxy-6-(5-fluoropentyl)-benzoic acid. LC-MS/ESI. Caled. [$C_{12}H_{15}FO_4$]242.10; Found [M–H] 240.95, [M–H—$CO_2$] 197.05, [2M–H] 482.80.

Example 3. Production of 2,4-dihydroxy-6-(5-fluoropentyl)-benzoic acid and 5-(5-fluoropentyl)-benzene-1,3-diol in *S. cerevisiae*

Strains expressing the acyl-activating enzymes revS and CsAAE3, as described in Example 1, are grown in 4 mL of selective media at 30° C. for 24 h and then inoculated into 1×YPD, giving a total of 40 mL of cell culture volume. After 30 h of growth at 30° C., 6-fluorohexanoic acid is added to the cultures to a total concentration of 2 mM, and the cultures are grown at 30° C. for a further 48 h. Analog production is monitored by HPLC and purification is accomplished as above.

Example 4. Production of 2,4-dihydroxy-6-(3-fluoropropyl)-benzoic acid and 5-(3-fluoropropyl)-benzene-1,3-diol in *S. cerevisiae*

Strains expressing revS and CsAAE3, as described in Example 1, were grown in 4 mL of selective media at 30° C. for 24 h and then inoculated into 1×YPD, giving a total of 40 mL of cell culture. After 30 h of growth at 30° C., 4-fluorobutanoic acid was added to the cultures to a total concentration of 2 mM, and the cultures were grown at 30° C. for a further 48 h. Analog production was monitored by HPLC and purification was accomplished as above. Unlike the perdeutero-analog production, the 3-fluoropropyl divarinic acid analog was only observed with strains expressing revS. Strains expressing CsAAE3 did not produce the analog at levels greater than the limit of detection by HPLC. As above, a total shift in the ratio of the acid analog to the decarboxylated fluoro-divarinol analog was observed using a truncated (95-amino acid) *C. sativa* cyclase or the AtHS1 cyclase.

Example 5. Production of 6-(4-chlorobutyl)-2,4-dihydroxybenzoic acid and 5-(4-chlorobutyl)-benzene-1,3-diol in *S. cerevisiae*

A strain expressing revS, as described in Example 1, was grown directly from a selective culture plate in 50 mL of selective media at 30° C. for 24 h and then inoculated into 2×YEPD, giving a total of 500 mL of cell culture volume. After 30 h of growth at 30° C., 5-chloropentanoic acid was added to the culture to a total concentration of 2 mM, and the culture was grown at 30° C. for a further 48 h. Analog production was monitored by the emergence of a reverse-phase IPLC peak in the predicted region, and purification was accomplished as above. The yield of 6-(4-chlorobutyl)-2,4-dihydroxybenzoic acid in the culture was ~30 mg/L.

6-(4-Chlorobutyl)-2,4-dihydroxybenzoic acid. LC-MS/ESI. Calcd. [$C_{11}H_{13}ClO_4$]244.05; Observed [M–H] 242.95.

In all the above examples, where desired, media that contained varying amounts of the acid analogs and olivetol/divarinol analogs could be converted quantitatively to the decarboxylated analogs by centrifugation to remove yeast cells, and heating the remaining analog-containing media at 100° C. for 1 hour.

Example 6. Use of an Organic Phase Overlay to Reduce Toxicity of Starting Materials and Products Perdeuterohexanoic acid, 6-fluorohexanoic acid, 4-fluorobutanoic acid, 5-chloropentanoic acid, hexanoic acid, and butanoic acid were fed individually to the yeast strains described above in Examples 1-3. Culturing of the cells proceeded as described in Example 3, except that at 30 h, 10% by volume of oleyl alcohol was added to the culture along with the aliphatic acid or aliphatic acid analog. This procedure led to increased levels of the desired products.

Example 7. Production of CBGA Analogs Directly in *S. cerevisiae*

The above deutero-, fluoro- and chloro-aliphatic acid analogs, along with hexanoic acid and butanoic acid, are fed individually to yeast strains grown as described above in Examples 1-3, except that the strains are previously modified by integrative transformation of genes involved in the up-regulation of the yeast mevalonate pathway such that they produce high levels of geranyl-diphosphate. The strains also harbor integrated genes that individually express various prenyltransferases for conversion of olivetolic acid analogs to CBGA analogs. The resulting CBGA analogs are isolated from centrifuged yeast cells by solvent extraction using methanol, ethanol or ethyl acetate, and are characterized by mass spectrometry and NMR analysis. 6-(4-Chlorobutyl)-3-(3,7-dimethyl-octa-2,6-dienyl)-2,4-dihydroxybenzoic acid was prepared using this procedure. LC-MS/ESI: Calcd. [$C_{21}H_{29}ClO_4$ ] 380.18; Found [M+H] 380.95 (Cl), [M−H] 378.85 (Cl).

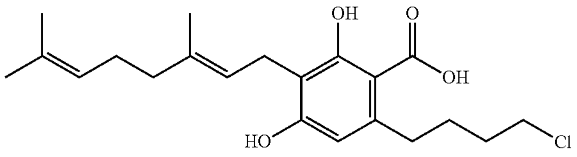 [SMILES: CC(C)=CCC/C(C)=C/Cc1c(O)cc(CCCCCl)c(C(=O)O)c1O]

3-(3,7-Dimethyl-octa-2,6-dienyl)-6-(5-fluoropentyl)-2,4-dihydroxy-benzoic acid (5-fluoro-cannabigeriolic acid) was also prepared using this procedure. LC-MS/ESI: Calcd. [$C_{22}H_{31}FO_4$] 278.22; Found [M+H] 379.05, [M−H] 376.90.

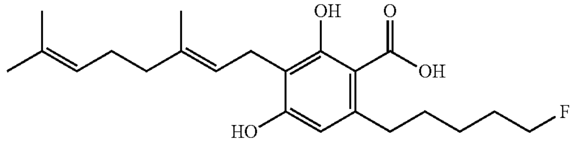 [SMILES: CC(C)=CCC/C(C)=C/Cc1c(O)cc(CCCCCF)c(C(=O)O)c1O]

Example 8. Chemical Transformation of Olivetol/Olivetolic Acid Analogs to CBC/CBCA Analogs CBCA and CBC analogs were prepared as follows: to a 0.5 mL dichloroethane solution of 35 mg (0.2 mmol) of perdeuteropentyl-olivetolic acid or perdeuteropentyl-olivetol was added 0.085 mL (approximately 2.5 equiv) of E/Z-citral followed by addition of 0.005 mL (25 mol %) of N,N-dimethylethylene diamine to initiate the reaction at 23° C. The reaction was monitored by quantitative RP-HPLC and after 18 h, no substrate remained. The reaction mixture was purified directly by a single injection on a Gilson preparative C18 RP-HPLC automated system using a steep linear gradient of water/MeOH/0.1% formic acid (2.5 mL/min). Fractions were monitored by UV (at 230 nm) and the appropriate fractions were combined, concentrated in vacuo, and re-concentrated in MeOH to remove residual water, to afford products in molar yields ranging from 65% to 73%. CBCA and CBC analogs were characterized by mass spectrometry and NMR analysis.

2-Methyl-2-(4-methyl-pent-3-enyl)-7-perdeuteropentyl-2H-chromen-5-ol (perdeuteropentyl-CBC). LC-MS/ESI: Calcd. [$C_{21}H_{19}D_{11}O_2$] 325.29; Found: [M+H]326.25.

5-Hydroxy-2-methyl-2-(4-methyl-pent-3-enyl)-7-perdeuteropentyl-2H-chromene-6-carboxylic acid (perdeuteropentyl-CBCA). LC-MS/ESI: Calcd. [$C_{22}H_{19}D_{11}O_4$] 369.28; Found: [M−H] 367.90, [M−H—$CO_2$] 324.00.

Fluorinated and chlorinated CBC/CBCA analogs are prepared as described above for the perdeuterated analogs.

Example 9. Preparation and Use of N-Acetylcysteinamide and Pantetheine Thioesters To a 0° C. stirred solution of 5.5 mmol of a carboxylic acid, containing 5 mmol of succinic acid, and 5 mmol of N-acetylcysteamine (or pantetheine) dissolved in 4 ml of dichloromethane (DCM), was added 1 mL of a cold solution of DCM containing 5.25 mmol of dicyclohexylcarbodiimde (DCC). The solution was allowed to warm to 23° C. and was stirred for 18 h. After cooling to 0° C., the resulting insoluble N,N'-dicyclohexylurea was removed by filtration and washed with cold DCM. The solvent was removed, the residue redissolved in DCM, re-filtered if necessary, and then extracted with iN HCl, followed by 5% NaHCO3 in saturated aqueous NaCl. The organic layer was dried over $NaSO_4$, and concentrated to afford the thioesters in high yield. The products were further purified by recrystallization, distillation, or chromatography. Particular examples include thioesters prepared from hexanoic acid, butanoic acid, pentanoic acid, heptanoic acid, octanoic acid, and fluorine- or deuterium-substituted alkyl and alkenyl acids such as 4-fluorobutanoic acid, 5-fluoropentanoic acid, 6-fluorohexanoic acid and perdeuterohexanoic acid.

The thioesters are fed up to a level of 2 mM into cultures such as those described in Examples 1 and 2, after 30 hours and, following growth for a further 46 hours, samples are taken for HPLC analysis. Yields of each acid product are measured at greater than 40 mg/L.

Example 10. Chemical Transformation of Olivetolic Acid Analogs to CBGA Analogs

To a suspension of 20 mg of deutero-, fluoro- or chloro-olivetolic acid analog in 0.25 mL of toluene is added 2.6 mg of p-toluenesulphonic acid and 18 µL of geraniol. The suspension is heated to 60° C. and monitored by reversed-phase HPLC (Kinetex 5 µm-XB, 50×4.6 mm, 100 A, linear gradient of 20% 50 mM ammonium formate/acetonitrile to 100% acetonitrile over 6 min. at 2.5 mL/min.). The corresponding CBGA analogs reach maximal yield after approximately 50 minutes, and are identified and characterized by mass spectrometry and NMR.

Example 11. Production of 5-fluorocannabichromene and 5-chlorocannabichromene 2,4-Dihydroxy-6-(5-fluoropentyl)-benzoic acid was prepared according to Example 2, decarboxylated, and converted to 5-fluorocannabichromene. A 37.5 mg sample of 2,4-dihydroxy-6-(5-fluoropentyl)-benzoic acid was taken up in 1 mL of 95% ethanol and heated at 80° C. for 18 hours to fully decarboxylate, providing 5-(5-fluoropentyl)-benzene-1,3-diol LC-MS/ESI: Calcd. [$C_{11}H_{15}FO_2$] 198.11; Found [M+H] 199.25, [M−H] 197.05. The resulting solution was concentrated (in vacuo) to dryness, and subjected to reaction conditions similar to those outlines in Example 8. 11.1 mg of 7-(5-fluoropentyl)-2-methyl-2-(4-methyl-pent-3-enyl)-2H-chromen-5-ol (5-fluorocannabichromene) was obtained. LC-MS/ESI: Calcd. [$C_{21}H_{29}FO_2$] 332.22; Found [M+H] 333.10, [M−H] 330.95, [2M−H] 662.85 $^1$H-NMR ($CDCl_3$, 300 MHz): δ 6.61 (d, 1, J=8 Hz, J=1.5 Hz); 6.24 (d, 1, J=1 Hz), 6.11 (d, 1, J=1 Hz), 5.50 (d, 1, J=12 Hz), 5.09 (dt, 1, J=6 Hz), 4.64 (bs s, 1), 4.51 (t, 1, J=6 Hz), 4.31 (t, 1, J=6 Hz), 2.10 (m, 4), 1.8-1.6 (m, 12), 1.67 (s, 3), 1.59 (s, 3), 1.45 (m, 2), 1.38 (s, 3).

In a similar fashion, 5-chlorocannabichromene was prepared from 2,4-dihydroxy-6-(4-chlorobutyl)-benzoic acid (see Example 5). LC-MS/ESI: Calcd. [$C_{20}H_{27}ClO_2$] 334.17; Found [M+H] 335.00 (Cl), [M−H] 332.90 (Cl); $^1$H-NMR ($CDCl_3$, 300 MHz): δ 6.62 (d, 1, J=8 Hz); 6.24 (d, 1, J=1 Hz), 6.12 (d, 1, J=1 Hz), 5.50 (d, 1, J=8 Hz), 5.09 (dt, 1, J=6 Hz), 3.53 (t, 3, J=6 Hz), 2.11 (m, 4), 1.8-1.5 (m, 4), 1.85 (s, 3), 1.57 (s, 3), 1.38 (s, 3).

Example 12. CB2 Receptor Agonist Activity of 5-fluorocannabichromene

The activity of 5-fluorocannabichromene (5F-CBC) was studied in AtT20 cells stably expressing HA-tagged human CB1 and CB2 receptors, as described by Udoh, et al. ("Cannabichromene is a cannabinoid CB2 receptor agonist." *British Journal of Pharmacology,* 2019, doi: 10.1111/bph.14815). The observed $EC_{50}$ value for 5F-CBC at CB2 was 2.1 μM.

VII. EXEMPLARY EMBODIMENTS

Exemplary embodiments provided in accordance with the presently disclosed subject matter include, but are not limited to, the claims and the following embodiments:

1. A compound according to Formula I:

(I)

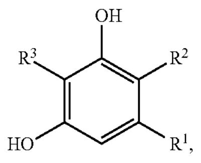

or a salt or cannabinoid derivative thereof, wherein:

$R^1$ is selected from the group consisting of $C_1$-$C_{20}$ haloalkyl, $C_1$-$C_{20}$ hydroxyalkyl, deuterated $C_1$-$C_{20}$ alkyl, tritiated $C_1$-$C_{20}$ alkyl, and $C_2$-$C_{20}$ alkenyl, $R^2$ is selected from the group consisting of $COOR^{2a}$ and H, $R^{2a}$ is selected from the group consisting of H and $C_1$-$C_6$ alkyl, and $R^3$ is selected from the group consisting of a prenyl moiety and H.

2. The compound of embodiment 1, or a salt or cannabinoid derivative thereof, wherein $R^1$ is selected from the group consisting of $C_1$-$C_{10}$ haloalkyl, $C_1$-$C_{10}$ hydroxyalkyl, deuterated $C_1$-$C_{10}$ alkyl, tritiated $C_1$-$C_{10}$ alkyl, and $C_2$-$C_{10}$ alkenyl.

3. The compound of embodiment 1, or a salt or cannabinoid derivative thereof, wherein $R^1$ is selected from the group consisting of $C_1$-$C_{10}$ haloalkyl, $C_1$-$C_{10}$ hydroxyalkyl, deuterated $C_1$-$C_{10}$ alkyl, and tritiated $C_1$-$C_{10}$ alkyl.

4. The compound of embodiment 1, or a salt or cannabinoid derivative thereof, wherein $R^1$ is $C_1$-$C_{10}$ haloalkyl.

5. The compound of embodiment 4, or a salt or cannabinoid derivative thereof, wherein $R^1$ is selected from the group consisting of fluoropentyl, fluoroethyl, fluoropropyl, fluorobutyl, fluorohexyl, fluorooctyl, and fluorononyl.

6. The compound of embodiment 4, or a salt or cannabinoid derivative thereof, wherein $R^1$ is selected from the group consisting of 5-fluoropropyl, 4-fluorobutyl, and 3-fluoropentyl.

7. The compound of embodiment 4, or a salt or cannabinoid derivative thereof, wherein $R^1$ is $C_1$-$C_{10}$ bromoalkyl or $C_1$-$C_{10}$ chloroalkyl.

8. The compound of embodiment 1, or a salt or cannabinoid derivative thereof, wherein $R^1$ is $C_1$-$C_{10}$ hydroxyalkyl.

9. The compound of embodiment 1, or a salt or cannabinoid derivative thereof, wherein $R^1$ is deuterated $C_1$-$C_{10}$ alkyl or tritiated $C_1$-$C_{10}$ alkyl.

10. The compound of any one of embodiments 1-9, or a salt or cannabinoid derivative thereof, wherein $R^2$ is selected from the group consisting of COOH and H.

11. The compound of any one of embodiments 1-10, or a salt or cannabinoid derivative thereof, wherein $R^2$ is COOH.

12. The compound of any one of embodiments 1-10, or a salt or cannabinoid derivative thereof, wherein $R^2$ is H.

13. The compound of any one of embodiments 1-12, or a salt or cannabinoid derivative thereof, wherein $R^3$ is H.

14. The compound of any one of embodiments 1-12, or a salt or cannabinoid derivative thereof, wherein $R^3$ is a prenyl moiety.

15. The compound of any one of embodiments 1-12 and 14, or a salt or cannabinoid derivative thereof, wherein the prenyl moiety is 3,7-dimethylocta-2,6-dien-1-yl.

16. The compound of embodiment 1, or a salt or cannabinoid derivative thereof, wherein the compound has a structure according to Formula Ia:

(Ia)

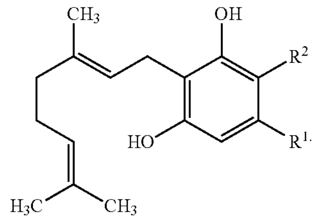

17. A cannabinoid derivative of a compound of any one of embodiments 1-16, or a salt thereof.

18. The cannabinoid derivative of embodiment 17, or a pharmaceutically acceptable salt thereof, which is selected from the group consisting of a halogenated cannabidiolic acid, a halogenated cannabidiol, a halogenated $\Delta^9$-tetrahydrocannabinolic acid, a halogenated $\Delta^8$-tetrahydrocannabinolic acid, a halogenated cannabichromenic acid, a halogenated cannabichromene, a halogenated cannabinol, a halogenated cannabinodiol, a halogenated cannabinolic acid, a cannabivarin, a halogenated cannabivarinic acid, a halogenated $\Delta^9$-tetrahydrocannabivarin, a halogenated $\Delta^8$-tetrahydrocannabivarin, a halogenated $\Delta^9$-tetrahydrocannabivarinic acid, a halogenated $\Delta^8$-tetrahydrocannabivarinic acid, a halogenated cannabigerovarin, a halogenated cannabigerovarinic acid, a halogenated cannabichromevarin, a halogenated cannabichromevarinic acid, a halogenated cannabidivarin, a halogenated cannabidivarinic acid, a halogenated cannabitriol, and a halogenated cannabicyclol.

19. A pharmaceutical composition comprising a cannabinoid derivative of embodiment 17 or embodiment 18 and a pharmaceutically acceptable excipient.

20. A method for treating a disease or condition mediated by cannabinoid receptor activity, the method comprising administering to an effective amount of a cannabinoid derivative of embodiment 17 or embodiment 18, or a pharmaceutically acceptable salt thereof, or an effective amount of a composition according to embodiment 19, to a subject in need thereof.

21. A method of producing a compound according to Formula IV:

(IV)

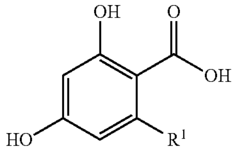

or a salt thereof, wherein $R^1$ is selected from the group consisting of $C_1$-$C_{20}$ haloalkyl, $C_1$-$C_{20}$ hydroxyalkyl, deuterated $C_1$-$C_{20}$ alkyl, tritiated $C_1$-$C_{20}$ alkyl, and $C_2$-$C_{20}$ alkenyl;

the method comprising culturing a modified recombinant host cell in a medium comprising a thioester according to Formula II;

(II)

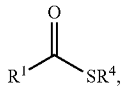

wherein $R^4$ is selected from the group consisting of a coenzyme A (CoA) moiety, a pantetheine moiety, and a cysteamine moiety, wherein the modified recombinant host cell comprises i. a first polynucleotide that encodes a synthase that converts the thioester according to Formula II and malonyl CoA to a tetraketide according to Formula III:

(III)

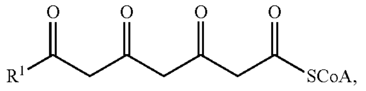

and ii. a second polynucleotide that encodes a 2-alkyl-4,6-dihydroxybenzoic acid cyclase that converts the tetraketide according to Formula III to the compound of Formula IV, and wherein the modified recombinant host cell is cultured under conditions in which products encoded by the first and second polynucleotides are expressed and the compound according to Formula IV is produced.

22. The method of embodiment 21, wherein $R^1$ is selected from the group consisting of $C_1$-$C_{10}$ haloalkyl, $C_1$-$C_{10}$ hydroxyalkyl, deuterated $C_1$-$C_{10}$ alkyl, tritiated $C_1$-$C_{10}$ alkyl, and $C_2$-$C_{10}$ alkenyl.

23. The method of embodiment 21 or embodiment 22, wherein the synthase is an olivetolic acid synthase.

24. The method of any one of embodiments 21-23, wherein the 2-alkyl-4,6-dihydroxybenzoic acid cyclase is a truncated olivetolic acid cyclase.

25. The method of any one of embodiments 21-24, wherein $R^4$ is a CoA moiety.

26. The method of any one of embodiments 21-25, wherein the host cell further comprises a third polynucleotide that encodes an acyl-CoA synthetase that converts a starting material according to Formula IIa (IIa)

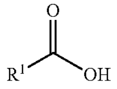

to the thioester according to Formula II, and wherein step a) comprises culturing the host cell under conditions in which the product encoded by the third polynucleotide is expressed and the thioester according to Formula II is produced.

27. The method of embodiment 26, wherein the acyl-CoA synthetase is revS or CsAAE3.

28. The method of any one of embodiments 21-24, wherein $R^4$ in the thioester according to Formula II is a pantetheine moiety or a cysteamine moiety.

29. The method of embodiment any one of embodiments 21-28, further comprising converting the compound of Formula IV to a compound of Formula V:

(V)

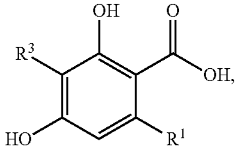

or a salt thereof, wherein $R^3$ is a prenyl moiety.

30. The method of embodiment 29, further comprising decarboxylating the compound of Formula V to provide a compound of Formula Va:

(Va)

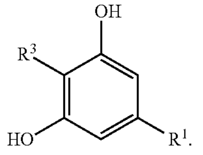

31. The method of embodiment any one of embodiments 21-28, further comprising decarboxylating the compound of Formula IV to provide a compound of Formula IVa:

(IVa)

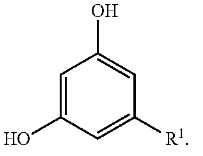

32. The method of embodiment 31, further comprising converting the compound Formula IVa to a compound of Formula Va:

(Va)

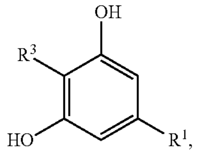

wherein $R^3$ is a prenyl moiety.

33. The method of any one of embodiments 29, 30, and 32, wherein the host cell further comprises a fourth polynucleotide that encodes a prenyltransferase enzyme converts the compound of Formula IV to the compound of Formula V, and wherein converting step b) comprises culturing the host cell under conditions in which the product encoded by the fourth polynucleotide is expressed and the compound according to Formula V is produced.
34. The method of embodiment 32, wherein the host cell further comprises a fourth polynucleotide that encodes a prenyltransferase enzyme converts the compound of Formula IVa to the compound of Formula Va, and wherein converting step b) comprises culturing the host cell under conditions in which the product encoded by the fourth polynucleotide is expressed and the compound according to Formula Va is produced.
35. The method of embodiment 33 or embodiment 34, wherein the prenyltransferase is geranylpyrophosphate: olivetolate geranyltransferase.
36. The method of embodiment 29 or embodiment 30, wherein converting step b) comprises forming a reaction mixture comprising 1) the compound of Formula IV, 2) geraniol, an activated geraniol, or citral, and 3) an organic solvent and maintaining the reaction mixture under conditions sufficient to the compound of Formula V.
37. The method of embodiment 32, wherein converting step b) comprises forming a reaction mixture comprising 1) the compound of Formula IVa, 2) geraniol, an activated geraniol, or citral and 3) an organic solvent and maintaining the reaction mixture under conditions sufficient to the compound of Formula Va.
38. A compound prepared according to any one of embodiments 29, 30, and 32-37, wherein the compound is a cannabidiolic acid analog, a cannabidiol analog, a $\Delta^9$-tetrahydrocannabinolic acid analog, a $\Delta^8$-tetrahydrocannabinolic acid analog, a cannabichromenic acid analog, a cannabichromene analog, a cannabinol analog, a cannabinodiol analog, a cannabinolic acid analog, a cannabivarin analog, a cannabivarinic acid analog, a $\Delta^9$-tetrahydrocannabivarin analog, a $\Delta^8$-tetrahydrocannabivarin analog, a $\Delta^9$-tetrahydrocannabivarinic acid analog, a $\Delta^8$-tetrahydrocannabivarinic acid analog, a cannabigerovarin analog, a cannabigerovarinic acid analog, a cannabichromevarin analog, a cannabichromevarinic acid analog, a cannabidivarin analog, a cannabidivarinic acid analog, a cannabitriol analog, or a cannabicyclol analog.

The invention illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. Thus, for example, some embodiments may encompass a host cell "comprising" a number of components, other embodiments would encompass a host cell "consisting essentially of" the same components, and still other embodiments would encompass a host cell "consisting of" the same components. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art. All patents, patent applications, and literature references cited in the present specification are hereby incorporated by reference in their entirety.

ILLUSTRATIVE SEQUENCES

Illustrative RevS polypeptide sequence GenBank BAK64635.1

SEQ ID NO: 1

```
MELALPAELAPTLPEALRLRSEQQPDTVAYVFLRDGETPEETLTYGRLDRAARARAA

ALEAAGLAGGTAVLLYPSGLEFVAALLGCMYAGTAGAPVQVPTRRRGMERARRIA

DDAGAKTILTTTAVKREVEEHFADLLTGLTVIDTESLPDVPDDAPAVRLPGPDDVAL

LQYTSGSTGDPKGVEVTHANFRANVAETVELWPVRSDGTVVNWLPLFHDMGLMFG

VVMPLFTGVPAYLMAPQSFIRRPARWLEAISRFRGTHAAAPSFAYELCVRSVADTGL

PAGLDLSSWRVAVNGAEPVRWTAVADFTEAYAPAGFRPQAMCPGYGLAENTLKLS

GSPEDRPPTLLRADAAALQDGRVVPLTGPGTDGVRLVGSGVTVPSSRVAVVDPGTG

TEQPAGRVGEIWINGPCVARGYHGRPAESAESFGARIAGQEARGTWLRTGDLGFLH

DGEVFVAGRLKDVVIHQGRNFYPQDIELSAEVSDRALHPNCAAAFALDDGRTERLV

LLVEADGRALRNGGADALRARVHDAVWDRQRLRIDEIVLLRRGALPKTSSGKVQRR

LARSRYLDGEFGPAPAREA
```

Illustrative *Cannabis sativa* CSAAE3 polypeptide sequence; GenBank AFD33347.1

SEQ ID NO: 2

```
MEKSGYGRDGIYRSLRPPLHLPNNNNLSMVSFLFRNSSSYPQKPALIDSETNQILSFSH

FKSTVIKVSHGFLNLGIKKNDVVLIYAPNSIHFPVCFLGIIASGAIATTSNPLYTVSELS

KQVKDSNPKLIIITVPQLLEKVKGFNLPTILIGPDSEQESSSDKVMTFNDLVNLGGSSGS

EFPIVDDFKQSDTAALLYSSGTTGMSKGVVLTHKNFIASSLMVTMEQDLVGEMDNV

FLCFLPMFHVFGLAIITYAQLQRGNTVISMARFDLEKMLKDVEKYKVTHLWVVPPVI

LALSKNSMVKKFNLSSIKYIGSGAAPLGKDLMEECSKVVPYGIVAQGYGMTETCGIV

SMEDIRGGKRNSGSAGMLASGVEAQIVSVDTLKPLPPNQLGEIWVKGPNMMQGYFN

NPQATKLTIDKKGWVHTGDLGYFDEDGHLYVVDRIKELIKYKGFQVAPAELEGLLV

SHPEILDAVVIPFPDAEAGEVPVAYVVRSPNSSLTENDVKKFIAGQVASFKRLRKVTFI

NSVPKSASGKILRRELIQKVRSNM
```

Illustrative *Cannabis sativa* CSAAE1 polypeptide sequence; GenBank AFD33345.1 A transmembrane domain is underlined

SEQ ID NO: 3

```
MGKNYKSLDSVVASDFIALGITSEVAETLHGRLAEIVCNYGAATPQTWINIANHILSP

DLPFSLHQMLFYGCYKDFGPAPPAWIPDPEKVKSTNLGALLEKRGKEFLGVKYKDPI

SSFSHFQEFSVRNPEVYWRTVLMDEMKISFSKDPECILRRDDINNPGGSEWLPGGYLN

SAKNCLNVNSNKKLNDTMIVWRDEGNDDLPLNKLTLDQLRKRVWLVGYALEEMG

LEKGCAIAIDMPMHVDAVVIYLAIVLAGYVVVSIADSFSAPEISTRLRLSKAKAIFTQD

HIIRGKKRIPLYSRVVEAKSPMAIVIPCSGSNIGAELRDGDISWDYFLERAKEFKNCEF

TAREQPVDAYTNILFSSGTTGEPKAIPWTQATPLKAAADGWSHLDIRKGDVIVWPTN

LGWMMGPWLVYASLLNGASIALYNGSPLVSGFAKFVQDAKVTMLGVVPSIVRSWK

STNCVSGYDWSTIRCFSSSGEASNVDEYLWLMGRANYKPVIEMCGGTEIGGAFSAGS

FLQAQSLSSFSSQCMGCTLYILDKNGYPMPKNKPGIGELALGPVMFGASKTLLNGNH

HDVYFKGMPTLNGEVLRRHGDIFELTSNGYYHAHGRADDTMNIGGIKISSIEIERVCN

EVDDRVFETTAIGVPPLGGGPEQLVIFFVLKDSNDTTIDLNQLRLSFNLGLQKKLNPLF

KVTRVVPLSSLPRTATNKIMRRVLRQQFSHFE
```

-continued

Illustrative olivetolic acid synthase polypeptide sequence; UniProtKB/Swiss-Prot: B1Q2B6.1

SEQ ID NO: 4

MNHLRAEGPASVLAIGTANPENILLQDEFPDYYFRVTKSEHMTQLKEKFRKICDKSM

IRKRNCFLNEEHLKQNPRLVEHEMQTLDARQDMLVVEVPKLGKDACAKAIKEWGQ

PKSKITHLIFTSASTTDMPGADYHCAKLLGLSPSVKRVMMYQLGCYGGGTVLRIAKD

IAENNKGARVLAVCCDIMACLFRGPSESDLELLVGQAIFGDGAAAVIVGAEPDESVG

ERPIFELVSTGQTILPNSEGTIGGHIREAGLIFDLHKDVPMLISNNIEKCLIEAFTPIGI

SDWNSIFWITHPGGKAILDKVEEKLHLKSDKFVDSRHVLSEHGNMSSSTVLFVMDELRK

RSLEEGKSTTGDGFEWGVLFGFGPGLTVERVVVRSVPIKY

Illustrative olivetolic acid cyclase polypeptide sequence; UniProtKB/Swiss-Prot: I6WU39.1

SEQ ID NO: 5

MAVKHLIVLKFKDEITEAQKEEFFKTYVNLVNIIPAMKDVYWGKDVTQKNKEEGYT

HIVEVTFESVETIQDYIIHPAHVGFGDVYRSFWEKLLIFDYTPRK

Olivetolic acid cyclase polypeptide sequence lacking the N-terminal methionine and C-terminal lysine relative to SEQ ID NO: 5

SEQ ID NO: 6

AVKHLIVLKFKDEITEAQKEEFFKTYVNLVNIIPAMKDVYWGKDVTQKNKEEGYTHI

VEVTFESVETIQDYIIHPAHVGFGDVYRSFWEKLLIFDYTPR

Truncated version of cyclase, 95 aa, lacking the N-terminal methionine and five amino acid sequence YTPRK at the C-terminal end relative to SEQ ID NO: 5

SEQ ID NO: 7

AVKHLIVLKFKDEITEAQKEEFFKTYVNLVNIIPAMKDVYWGKDVTQKNKEEGYTHI

VEVTFESVETIQDYIIHPAHVGFGDVYRSFWEKLLIFD

Amino acid sequence of 415-amino acid C-terminal domain of *Ralstonia solanacearum* acyl-CoA synthase

SEQ ID NO: 8

MAFNERVVDWQQVAGAQPDASPERMSADDPFMIIYTSGTTGKPKGTVHTHGSFPM

KIAHDSAIHFNVSPKDVFCWPADMGWVAGTLVMSCALLRGATLVCYDGAPDFPDW

SRMSRLIERHRVTHFGSAPTLIRGLASNEAIATQGDVSSVKLLITAGEGIDPEHFLWFQ

KAFGGGHRPVINYTGGTEVSGALLSSVVIKPISPAGFNTASPGVATDVVDAEGHSVT

GEVGELAIRKPFIGMTRSFWQDDERYLDSYWRTIPGIWVHGDLAMRREDGMWFMM

GRSDDTIKLAGKRLGPAEIEDVLLELPEIAEAAAIGVEDPVKGQKLVVFVVASKASTA

SADALASVIGKHVDLRLGRPFRPSVVHVVAQLPKTRSSKIIVIRRVIRSVYTGKPAGDL

SSLDNPLALDEIRSAAAVS

Amino acid sequence of cyclase domain from the benH gene product of the benastatin gene cluster of *Streptomyces* spp.

SEQ ID NO: 9

AGRTDNSVVIDAPVQLVWDMTNDVSQWAVLFEEYAESEVLAVDGDTVRFRLTTQP

DEDGKQWSWVSERTRDLENRTVTARRLDNGLFEYMNIRWEYTEGPDGVRMRWIQE

FSMKPSAPVDDSGAEDHLNRQTVKEMARIKKLIEEA

---

What is claimed is:

1. A pharmaceutical composition comprising a compound according to Formula I:

(I)

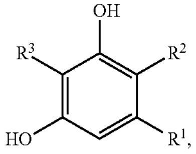

or a salt or cannabinoid derivative thereof, wherein:

$R^1$ is selected from the group consisting of $C_1$-$C_{20}$ haloalkyl, $C_1$-$C_{20}$ hydroxyalkyl, $C_2$-$C_{20}$ alkenyl, deuterated $C_1$-$C_{20}$ alkyl, and tritiated $C_1$-$C_{20}$ alkyl, $R^2$ is selected from the group consisting of $COOR^{2a}$ and H, $R^{2a}$ is selected from the group consisting of H and $C_1$-$C_6$ alkyl, and $R^3$ is a prenyl moiety and the prenyl moiety is 3,7-dimethylocta-2,6-dien-1-yl;

wherein the cannabinoid derivative is selected from the group consisting of:

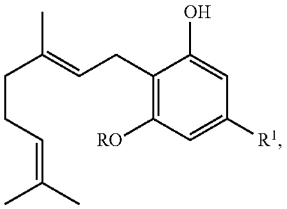

-continued

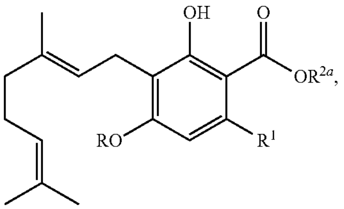

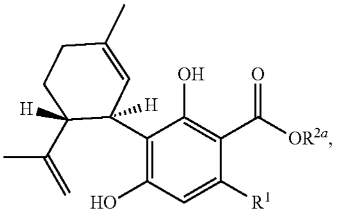

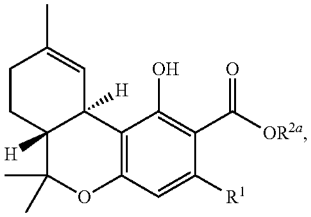

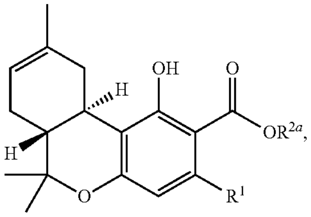

-continued

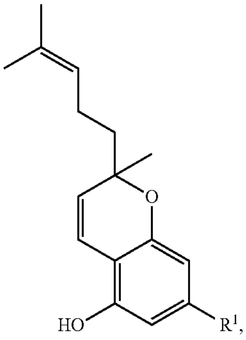

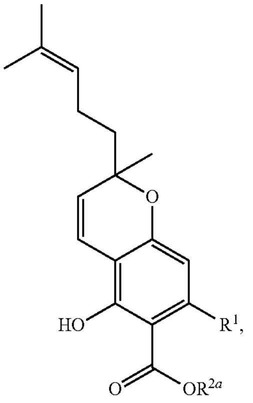

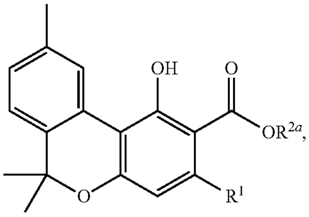

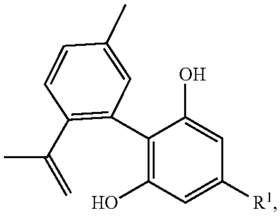

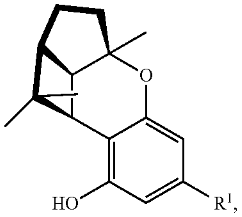

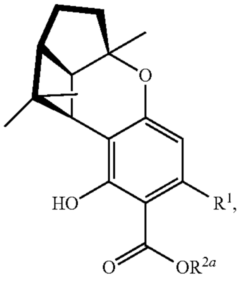

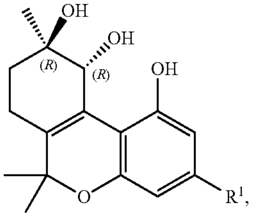

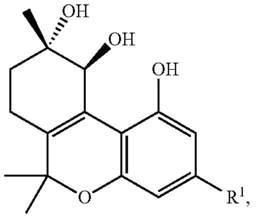

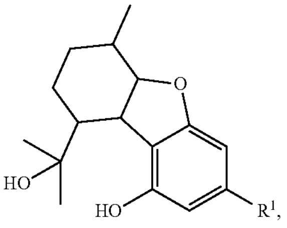

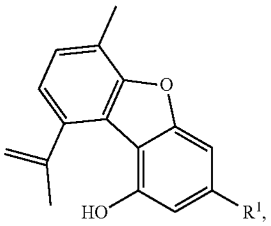

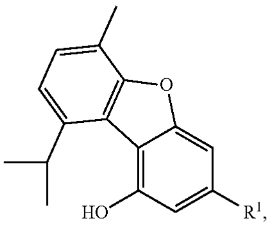

-continued

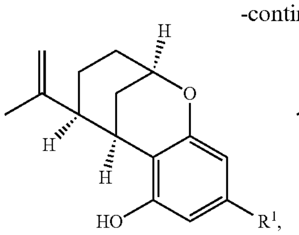

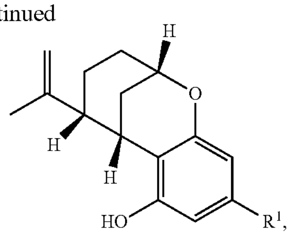

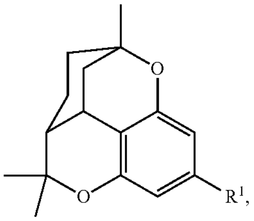

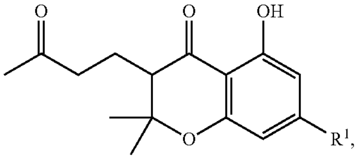

and

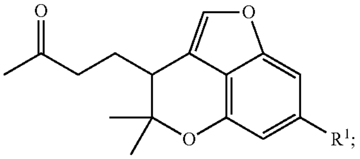

wherein R is H or $CH_3$; or
wherein the cannabinoid derivative is

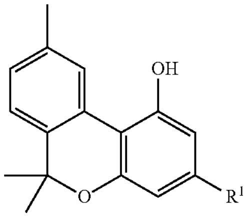

and $R^1$ is $C_1$-$C_{20}$ haloalkyl or $C_2$-$C_{20}$ alkenyl; and a pharmaceutically acceptable excipient.

2. The pharmaceutical composition of claim 1, where in the compound or a salt or cannabinoid derivative thereof, $R^1$ $C_2$-$C_{10}$ alkenyl.

3. The pharmaceutical composition of claim 1, where in the compound or a salt or cannabinoid derivative thereof, $R^1$ is $C_1$-$C_{10}$ haloalkyl.

4. The pharmaceutical composition of claim 3 where in the compound or a salt or cannabinoid derivative thereof, $R^1$ is selected from the group consisting of fluoropentyl, fluoroethyl, fluoropropyl, fluorobutyl, fluorohexyl, fluorooctyl, and fluorononyl.

5. The pharmaceutical composition of claim 3, where in the compound or a salt or cannabinoid derivative thereof, $R^1$ is selected from the group consisting of 3-fluoropropyl, 4-fluorobutyl, 5-fluoropentyl, and 3-fluoropentyl.

6. The pharmaceutical composition of claim 3, where in the compound or a salt or cannabinoid derivative thereof, $R^1$ is $C_1$-$C_{10}$ chloroalkyl.

7. The pharmaceutical composition of claim 1, where in the compound or a salt or cannabinoid derivative thereof, $R^1$ is $C_1$-$C_{10}$ hydroxyalkyl when the cannabinoid derivative is not

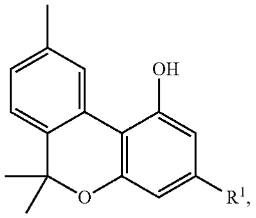

8. The pharmaceutical composition of claim 1, where in the compound or a salt or cannabinoid derivative thereof, $R^2$ is selected from the group consisting of COOH and H.

9. The pharmaceutical composition of claim 1, wherein the compound according to Formula (I) is according to Formula Ia:

(Ia)

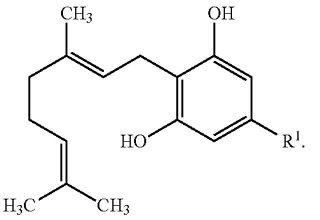

or a salt or cannabinoid derivative thereof.

10. The pharmaceutical composition of claim 1, wherein the compound of Formula (I) is a cannabinoid derivative thereof, or a salt thereof.

11. The pharmaceutical composition of claim 1, wherein the cannabinoid derivative or salt thereof is selected from the group consisting of:

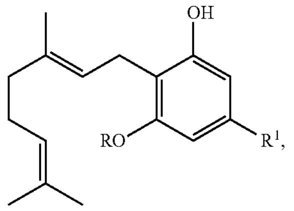

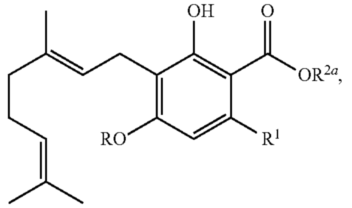

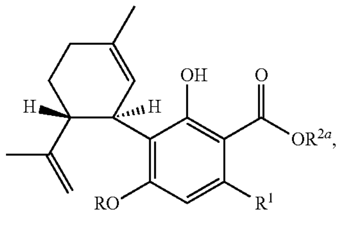

-continued

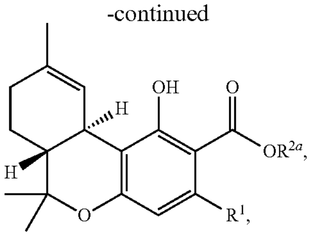

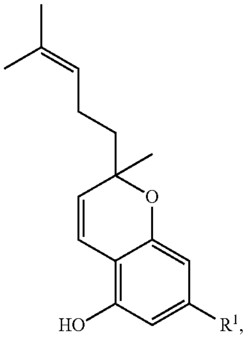

and

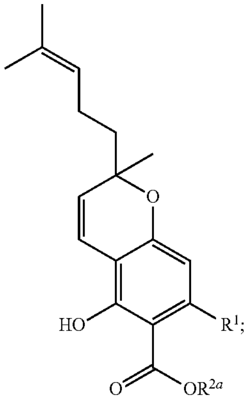

or wherein the cannabinoid derivative is

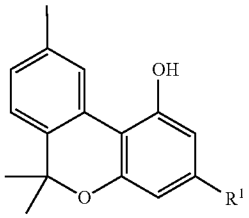

and $R^1$ is $C_1$-$C_{20}$ haloalkyl or $C_2$-$C_{20}$ alkenyl; and wherein R is H.

12. The pharmaceutical composition of claim 1, wherein the cannabinoid derivative or salt thereof is selected from the group consisting of:

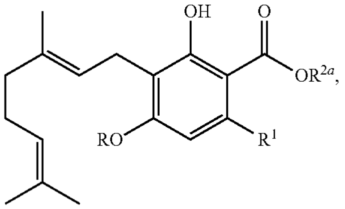

-continued

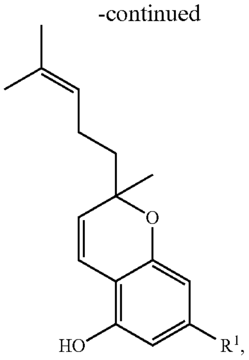

and

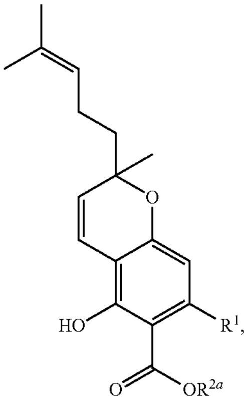

wherein R is H or $CH_3$;
or wherein the cannabinoid derivative is

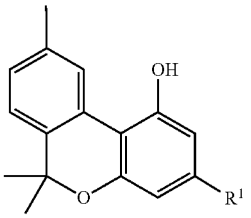

and $R^1$ is $C_1$-$C_{20}$ haloalkyl or $C_2$-$C_{20}$ alkenyl.

13. The pharmaceutical composition of claim 1, the salt is a pharmaceutically acceptable salt thereof.

14. The pharmaceutical composition of claim 3, where in the compound or a salt or cannabinoid derivative thereof, $R^1$ is $C_1$-$C_{10}$ bromoalkyl.

15. The pharmaceutical composition of claim 1, wherein the compound of Formula (I) is selected from the group consisting of:

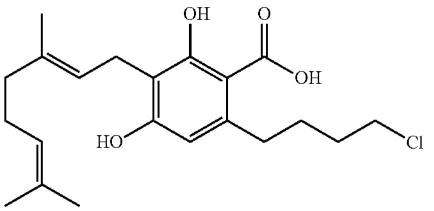

and

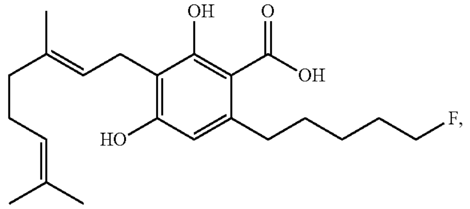

and the cannabinoid derivative is selected from the group consisting of

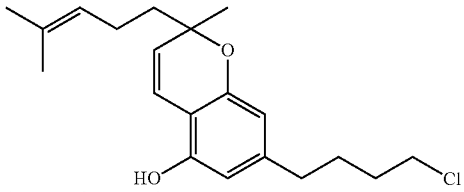

and

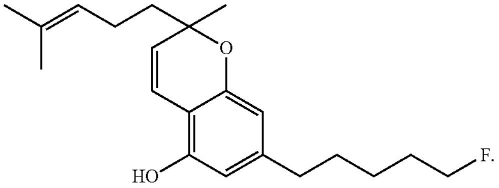

16. A method for treating a disease or condition mediated by cannabinoid receptor activity, the method comprising administering an effective amount of the pharmaceutical composition of claim 1, comprising a) a cannabinoid derivative, or a pharmaceutically acceptable salt thereof.

* * * * *